United States Patent
Craw et al.

(10) Patent No.: US 8,024,421 B2
(45) Date of Patent: Sep. 20, 2011

(54) DEVICE DATA SHEETS AND DATA DICTIONARIES FOR A DYNAMIC MEDICAL OBJECT INFORMATION BASE

(75) Inventors: Chad E. Craw, Fulton, NY (US); James J. DelloStritto, Jordan, NY (US); Song Y. Chung, Canton, GA (US); Ronald J. Blaszak, Syracuse, NY (US); Frank LoMascolo, Auburn, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 152 days.

(21) Appl. No.: 11/905,829

(22) Filed: Oct. 4, 2007

(65) Prior Publication Data
US 2008/0133699 A1    Jun. 5, 2008

Related U.S. Application Data

(60) Provisional application No. 60/848,993, filed on Oct. 4, 2006.

(51) Int. Cl.
*G06F 15/173* (2006.01)
(52) U.S. Cl. ........................................ 709/217; 709/225
(58) Field of Classification Search .................. 709/217, 709/225
See application file for complete search history.

(56) References Cited

U.S. PATENT DOCUMENTS

| | | |
|---|---|---|
| 5,261,080 A | 11/1993 | Khoyi et al. |
| 5,307,262 A | 4/1994 | Ertel |
| 5,446,880 A | 8/1995 | Balgeman et al. |
| 5,517,622 A | 5/1996 | Ivanoff et al. |
| 5,664,126 A | 9/1997 | Hirakawa |
| 5,708,828 A | 1/1998 | Coleman |
| 5,710,908 A | 1/1998 | Man |
| 5,721,895 A | 2/1998 | Velissaropoulos et al. |
| 5,724,580 A | 3/1998 | Levin |
| 5,734,907 A | 3/1998 | Jarossay et al. |
| 5,857,195 A | 1/1999 | Hayashi |
| 5,892,925 A | 4/1999 | Aditya et al. |

(Continued)

FOREIGN PATENT DOCUMENTS

EP   0640913 A3   3/1995

(Continued)

OTHER PUBLICATIONS

International Search Report & Written Opinion for PCT/US2006/011373, dated Feb. 6, 2008.

(Continued)

*Primary Examiner* — Wing Chan
*Assistant Examiner* — Kostas Katsikis
(74) *Attorney, Agent, or Firm* — Merchant & Gould

(57) ABSTRACT

Methods and systems are provided for communicating between network devices. A data dictionary may be derived from a device data sheet. The data dictionary may include one or more data definitions specific to the network device and a global unique identifier for the network device. The data dictionary and data are received from the network device. Data definitions from the data dictionary are used to extract and process information from the data. The data dictionary may include a hierarchal classification scheme for data including a first level, a second level and a third level, wherein the first level defines a type of data, wherein the second level defines a type of action, and wherein the third level defines an object of the action.

23 Claims, 44 Drawing Sheets

U.S. PATENT DOCUMENTS

| | | |
|---|---|---|
| 5,999,979 A | 12/1999 | Vellanki |
| 6,026,392 A | 2/2000 | Kouchi et al. |
| 6,050,940 A | 4/2000 | Braun |
| 6,130,917 A | 10/2000 | Monroe |
| 6,190,313 B1 | 2/2001 | Hinkle |
| 6,226,620 B1* | 5/2001 | Oon ................... 705/2 |
| 6,249,668 B1 | 6/2001 | Abe |
| 6,250,309 B1 | 6/2001 | Krichen et al. |
| 6,275,869 B1 | 8/2001 | Sieffert et al. |
| 6,330,572 B1 | 12/2001 | Sitka |
| 6,332,163 B1 | 12/2001 | Bowman-Amuah |
| 6,400,286 B1 | 6/2002 | Cooper |
| 6,496,851 B1 | 12/2002 | Morris |
| 6,584,445 B2 | 6/2003 | Papageorge |
| 6,616,606 B1 | 9/2003 | Peterson |
| 6,625,617 B2 | 9/2003 | Yarnall et al. |
| 6,633,833 B2 | 10/2003 | Sharma et al. |
| 6,644,322 B2 | 11/2003 | Webb |
| 6,651,104 B1 | 11/2003 | Moon |
| 6,665,725 B1 | 12/2003 | Dietz |
| 6,669,631 B2 | 12/2003 | Norris et al. |
| 6,697,103 B1 | 2/2004 | Fernandez et al. |
| 6,721,286 B1 | 4/2004 | Williams et al. |
| 6,766,361 B1 | 7/2004 | Venigalla |
| 6,779,004 B1 | 8/2004 | Zintel |
| 6,792,431 B2 | 9/2004 | Tamboli et al. |
| 6,801,331 B1 | 10/2004 | Motoyama |
| 6,820,135 B1 | 11/2004 | Dingman |
| 6,839,717 B1 | 1/2005 | Motoyama et al. |
| 6,848,108 B1 | 1/2005 | Caron |
| 6,915,312 B2 | 7/2005 | Bodnar et al. |
| 6,940,807 B1 | 9/2005 | Rezvani et al. |
| 6,942,616 B2 | 9/2005 | Kerr, II |
| 6,951,539 B2 | 10/2005 | Bardy |
| 6,978,422 B1* | 12/2005 | Bushe et al. ................... 715/734 |
| 6,993,536 B2 | 1/2006 | Yamanaka |
| 7,016,963 B1 | 3/2006 | Judd et al. |
| 7,054,924 B1 | 5/2006 | Harvey et al. |
| 7,065,579 B2 | 6/2006 | Traversat |
| 7,124,299 B2* | 10/2006 | Dick et al. ................ 713/178 |
| 7,136,927 B2 | 11/2006 | Traversat |
| 7,181,508 B1* | 2/2007 | Sretenovic ............. 709/220 |
| 7,200,671 B1 | 4/2007 | Lev-Ami |
| 7,321,861 B1* | 1/2008 | Oon ...................... 705/3 |
| 7,340,500 B2 | 3/2008 | Traversat |
| 7,360,154 B2 | 4/2008 | Gale |
| 7,389,474 B2 | 6/2008 | Rettig |
| 7,392,255 B1 | 6/2008 | Sholtis |
| 7,408,932 B2 | 8/2008 | Kounavis |
| 7,653,227 B2* | 1/2010 | Krishnan et al. ........... 382/128 |
| 7,725,606 B2 | 5/2010 | Lev-Ami |
| 7,783,637 B2 | 8/2010 | Bitsch |
| 7,788,648 B2 | 8/2010 | Bossom |
| 2001/0011222 A1 | 8/2001 | McLauchlin |
| 2001/0023315 A1* | 9/2001 | Flach et al. ................ 600/300 |
| 2001/0044809 A1 | 11/2001 | Parasnis et al. |
| 2001/0052012 A1 | 12/2001 | Rinne |
| 2002/0010797 A1 | 1/2002 | Moulton |
| 2002/0013518 A1 | 1/2002 | West |
| 2002/0023172 A1 | 2/2002 | Gendron |
| 2002/0037035 A1 | 3/2002 | Singh |
| 2002/0072933 A1 | 6/2002 | Vonk et al. |
| 2002/0099854 A1 | 7/2002 | Jorgensen |
| 2002/0128862 A1* | 9/2002 | Lau et al. ................... 705/2 |
| 2002/0143824 A1 | 10/2002 | Lee et al. |
| 2002/0184384 A1 | 12/2002 | Simmon et al. |
| 2003/0004403 A1 | 1/2003 | Drinan |
| 2003/0037043 A1* | 2/2003 | Chang et al. ................ 707/3 |
| 2003/0074248 A1 | 4/2003 | Braud et al. |
| 2003/0093459 A1 | 5/2003 | Dowling |
| 2003/0177035 A1* | 9/2003 | Oka et al. ................... 705/2 |
| 2003/0212982 A1 | 11/2003 | Brooks et al. |
| 2003/0233250 A1 | 12/2003 | Joffe et al. |
| 2004/0030763 A1 | 2/2004 | Manter |
| 2004/0044545 A1 | 3/2004 | Weismann et al. |
| 2004/0088374 A1 | 5/2004 | Webb et al. |
| 2004/0143677 A1 | 7/2004 | Novak |
| 2004/0172442 A1 | 9/2004 | Ripley |
| 2004/0176983 A1 | 9/2004 | Birkett et al. |
| 2004/0215830 A1 | 10/2004 | Shenfield |
| 2005/0038326 A1 | 2/2005 | Mathur |
| 2005/0054921 A1 | 3/2005 | Katsman et al. |
| 2005/0071316 A1 | 3/2005 | Caron |
| 2005/0071324 A1* | 3/2005 | Bitsch et al. ................ 707/3 |
| 2005/0071486 A1 | 3/2005 | Vu et al. |
| 2005/0091358 A1 | 4/2005 | Mehra et al. |
| 2005/0125778 A1 | 6/2005 | Fleegal |
| 2005/0154855 A1 | 7/2005 | Harris et al. |
| 2005/0165947 A1 | 7/2005 | Auriemma |
| 2005/0198364 A1 | 9/2005 | Val |
| 2005/0204022 A1* | 9/2005 | Johnston et al. ............ 709/220 |
| 2005/0273772 A1 | 12/2005 | Matsakis |
| 2006/0017563 A1 | 1/2006 | Rosenfeld et al. |
| 2006/0069605 A1* | 3/2006 | Hatoun ...................... 705/9 |
| 2006/0101109 A1 | 5/2006 | Nishio |
| 2006/0111936 A1 | 5/2006 | Mahesh et al. |
| 2006/0129435 A1 | 6/2006 | Smitherman |
| 2006/0168513 A1* | 7/2006 | Coulson et al. ............. 715/513 |
| 2007/0061393 A1 | 3/2007 | Moore |
| 2007/0073872 A1 | 3/2007 | Wille |
| 2007/0094548 A1 | 4/2007 | Lev-Ami |
| 2007/0156726 A1 | 7/2007 | Levy |
| 2007/0208865 A1 | 9/2007 | Morris |
| 2008/0052384 A1* | 2/2008 | Marl et al. ................ 709/223 |
| 2008/0082683 A1 | 4/2008 | DelloStritto et al. |
| 2008/0134133 A1 | 6/2008 | DelloStritto |
| 2008/0140770 A1 | 6/2008 | DelloStritto et al. |
| 2009/0037514 A1 | 2/2009 | Lankford |
| 2010/0005448 A1 | 1/2010 | DelloStritto et al. |

FOREIGN PATENT DOCUMENTS

| | | |
|---|---|---|
| EP | 1407714 A1 | 4/2004 |
| WO | WO 03067842 A2 * | 8/2003 |
| WO | WO2005/043386 A1 | 5/2005 |
| WO | WO2005/067210 A1 | 7/2005 |
| WO | WO 2006/105139 | 10/2006 |
| WO | WO2008/045276 A2 | 4/2008 |

OTHER PUBLICATIONS

Baird et al: "Communicating Data from Wireless Sensor Networks Using the HL7v3 Standard"; IEEE Computer Society; Proceedings of the International Workshop on Wearable and Implantable Body Sensor Networks; 183-186; Apr. 3, 2006; 4 pages.

Dolin et al: "HL7 Clinical Document Architecture, Release 2"; Journal of The American Medical Informatics Association, Hanley and Belfus, PA, US; vol. 13, No. 1; Jan. 1, 2006; 10 pages.

Helfenbein et al: "Philips Medical Systems Support for Open ECG and Standardization Efforts"; Computers in Cardiology 2004; 31:393-396; Chicago, IL; Sep. 19, 2004; 4 pages.

Norgall, Thomas: "ECG Data Interchange Formats and Protocols—Status and Outlook"; 2nd Open ECG Workshop 2004; Berlin, Germany; Apr. 1, 2004; accessed at: http://www.openecg.net/WS2_proceedings/Session05/S5.2_PA.pdf; retrieved on Jul. 11, 2008; 2 pages.

Ruiz et al: "An Open Standard Platform for Interoperability of Medical Devices"; Studies in Health Technology and Informatics, 1005-1009, IOS Press, Amsterdam, NL; Jan. 1, 2000; 6 pages.

WIPO Publication (WO 2008/045276 A3) of International Search Report for International Application No. PCT/US2007/021296, mailed Nov. 18, 2008 (9 pages).

Yao et al: "Applying The ISO/IEEE 11073 Standards to Wearable Home Health Monitoring Systems"; Journal of Clinical Monitoring and Computing vol. 19 No. 6: 427-436; Dec. 1, 2005; 10 pages.

* cited by examiner

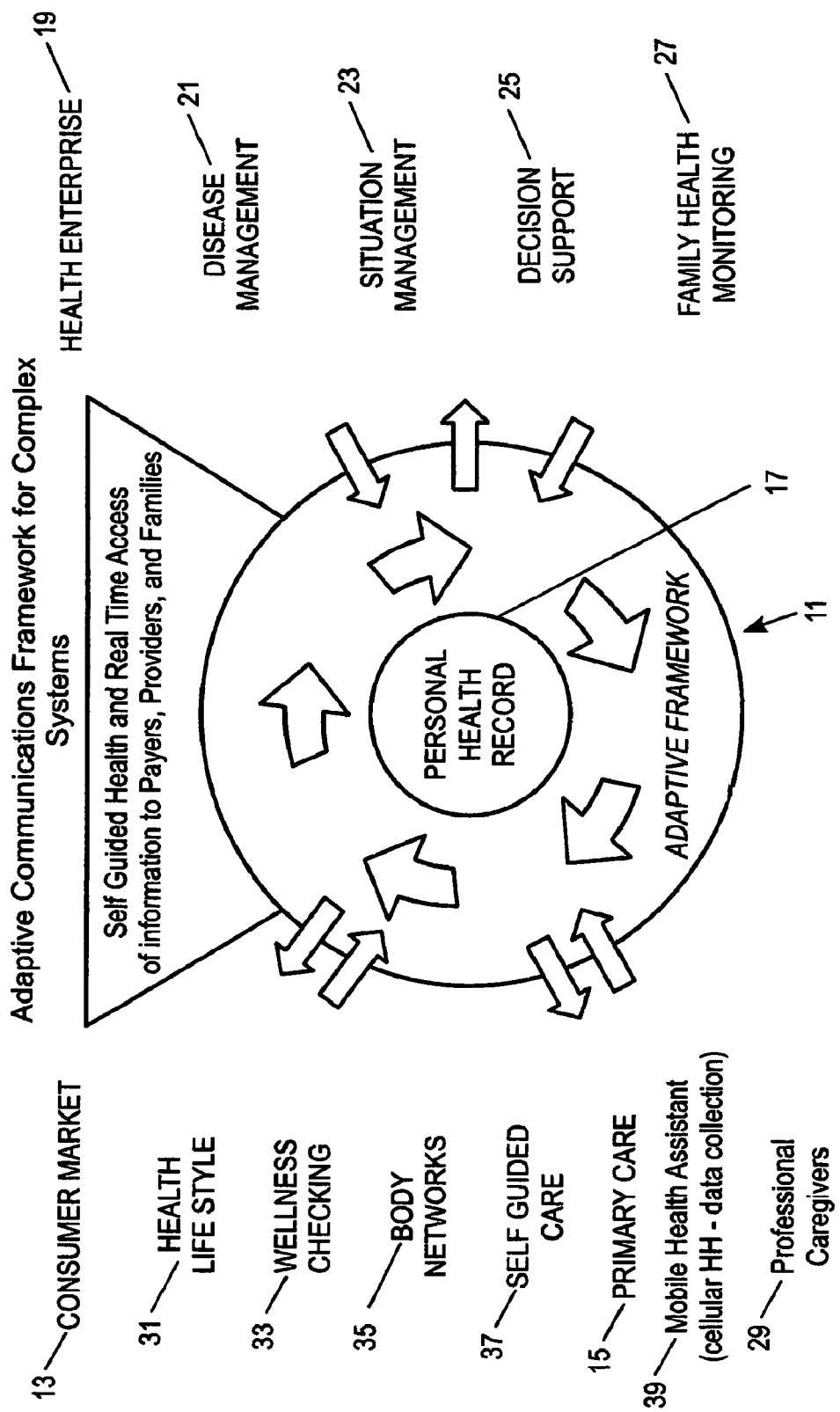
FIG. 1A - PRIOR ART -

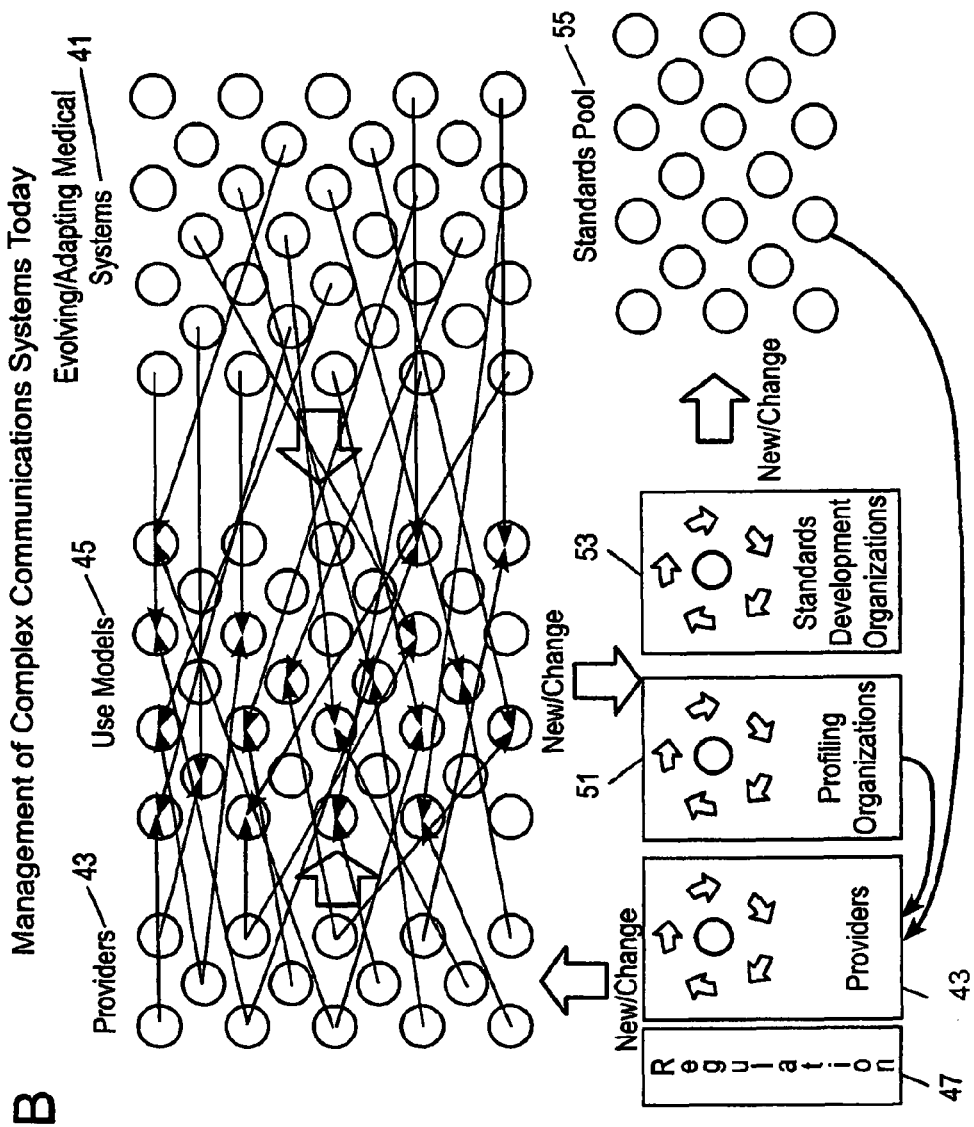

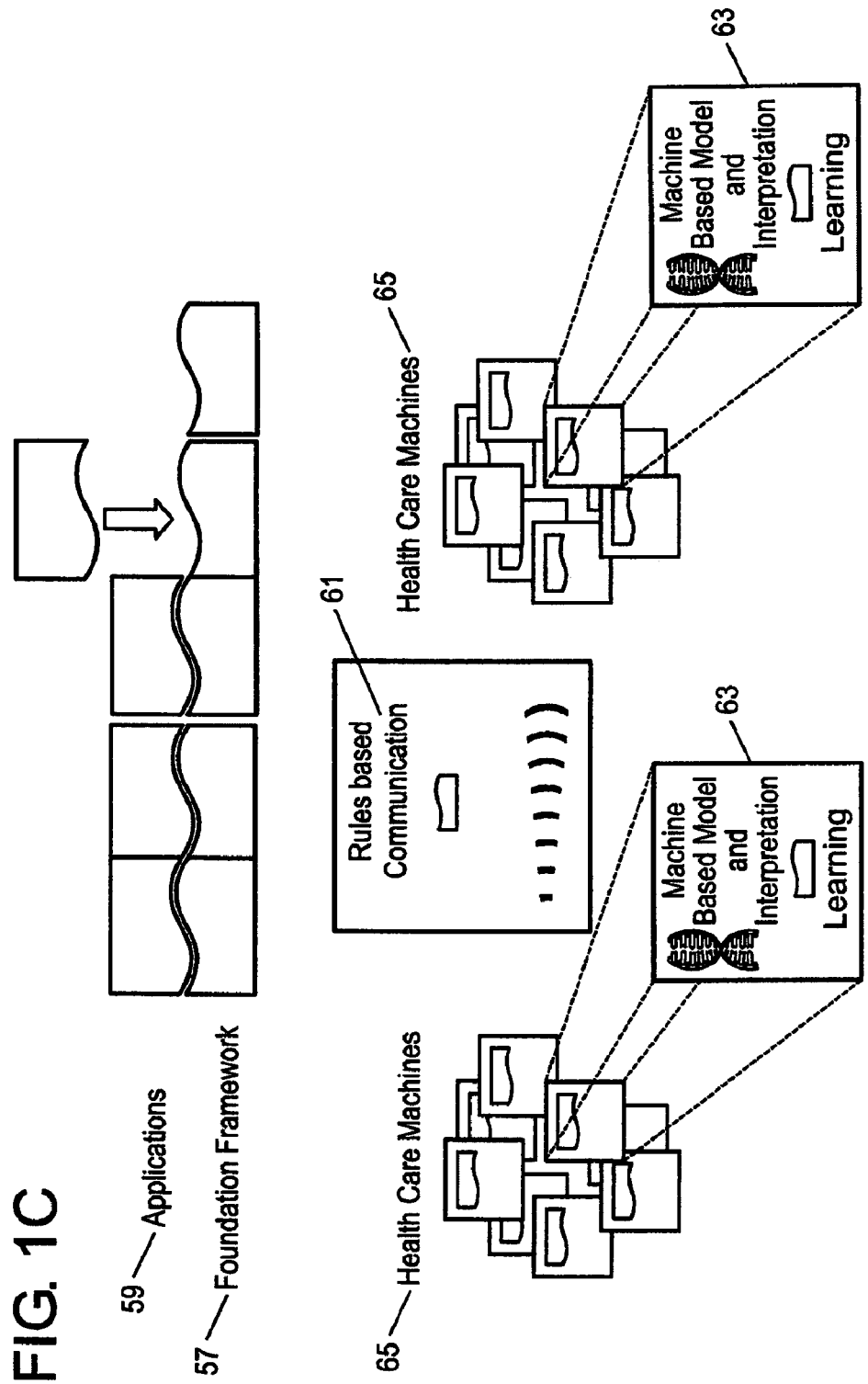

1303 — Level 1 Family
1305 — Level 2 Genus
1307 — Level 3 Species

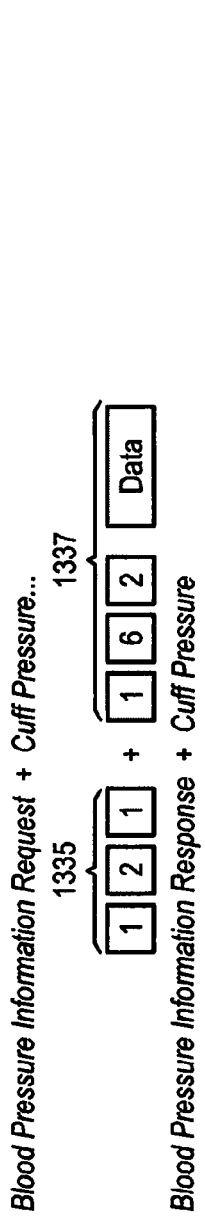

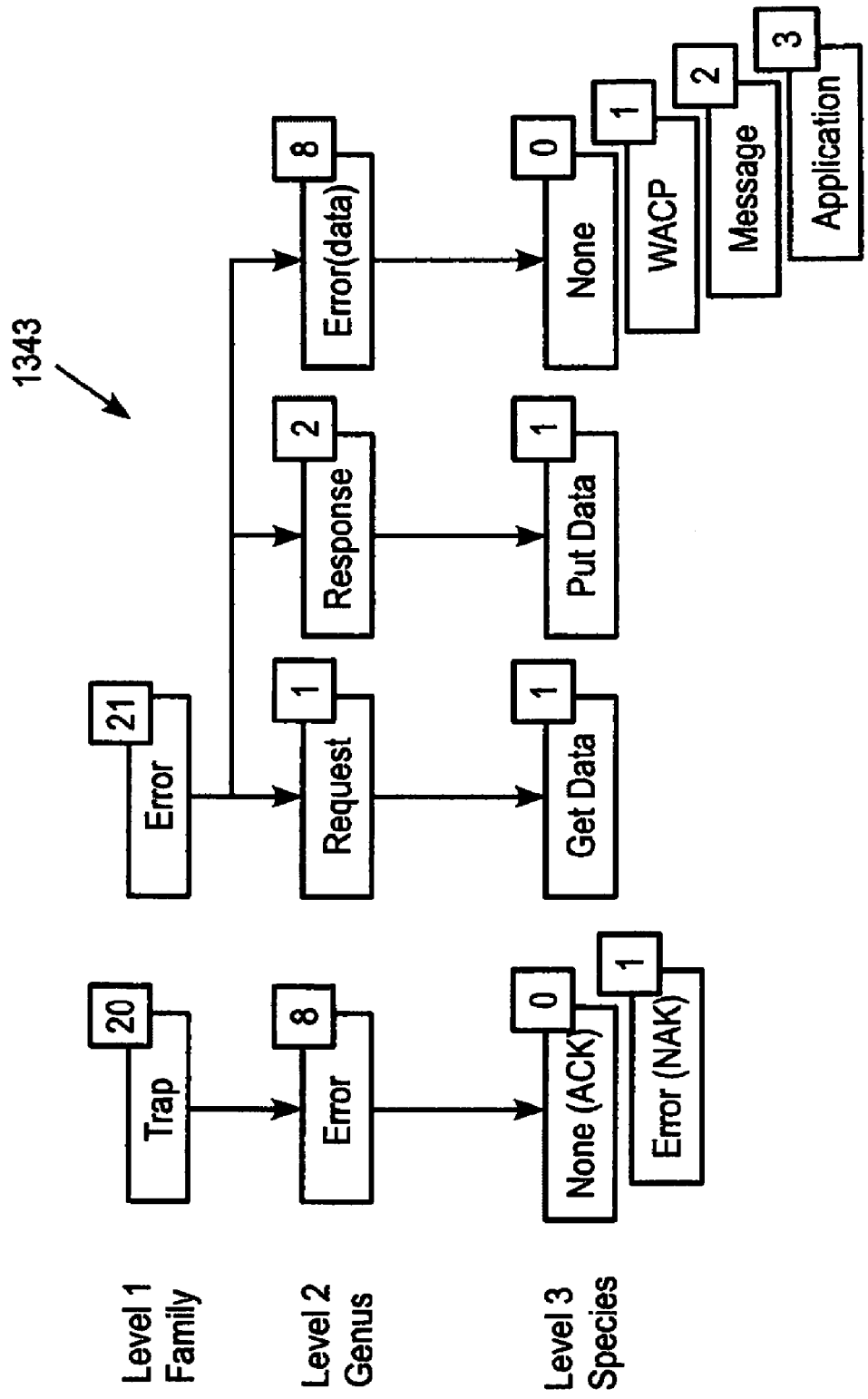

Blood Pressure Command Execute + parameter ("Start_BP")

POSITIVE RESPONSE - (Yes)

Trap (acknowledge or Yes) Message includes an exception or zero for no error.

NEGATIVE RESPONSE - (No!)

Trap (no-acknowledge or no). Message includes an error code.

Blood Pressure Information Report + Cuff Pressure...

POSITIVE RESPONSE - (Yes)

Trap (acknowledge or Yes) Message includes an error code likely to be zero.

NEGATIVE RESPONSE - (No!)

Trap (no-acknowledge or no). Message includes an error code.

Blood Pressure Information Report + Cuff Pressure...

FIG. 6B

Family Numeric - Genus Data - Species N  — 1395

| x | 6 | 1 | = Systolic Numeric - Species 1
| x | 6 | 2 | = Diastolic Numeric - Species 2
| x | 6 | 3 | = Heart Rate Numeric - Species 3
| x | 6 | 4 | = Mean Arterial Pressure - Species 4
| x | 6 | 5 | = Temperature - Species 5
| x | 6 | 6 | = SpO$_2$ - Species 6
| x | 6 | 7 | = Weight - Species 7

Family Numeric - Genus Configuration - Species N  — 1393

| x | 7 | 1 | = Systolic Numeric - Species 1
| x | 7 | 2 | = Diastolic Numeric - Species 2
| x | 7 | 3 | = Heart Rate Numeric - Species 3
| x | 7 | 4 | = Mean Arterial Pressure - Species 4
| x | 7 | 5 | = Temperature - Species 5
| x | 7 | 6 | = SpO$_2$ - Species 6
| x | 7 | 7 | = Weight - Species 7

= diagnostic results for a Non invasive blood Pressure (NIBP)

```xml
<?xml version="1.0" encoding="ISO-8859-1" ?>
<FAMILY name="FmNIBP">
<!-- ================================================= -->
<!-- CnDATA                                             -->
<!-- ================================================= -->
-<DEFINITION class="CNIBPDStd" abrv="CNIBPDSTD" version="100" family="FmNIBP" genus="GnDATA" species="SpSTANDARD">
  -<MEMBERS>
    <!-- Version 001 -->
    <MEMBER type="Int16" name="Systolic" minversion="100" maxversion="CURRENT_VERSION" scale="0.01" units="mm/Hg" AKA="10024"
      comment="Systolic BP {in 0.01 mmHg units}"/>
    <MEMBER type="Int16" name="Diastolic" minversion="100" maxversion="CURRENT_VERSION" scale="0.01" units="mm/Hg" AKA="10025"
      comment="Diastolic BP {in 0.01 mmHg units}"/>
    <MEMBER type="Int16" name="MAP" minversion="100" maxversion="CURRENT_VERSION" scale="0.01" units="mm/Hg" AKA="10026"
      comment="Mean Arterial Pressure {in 0.01 mmHg units}"/>
    <MEMBER type="uint16" name="HR" minversion="100" maxversion="CURRENT_VERSION" units="BPM" AKA="10050"
      comment="NIBP Heart Rate {in BPM (Beats/Minute) units}"/>
  </MEMBERS>
  -<SPECIES_TABLE>
    <SPECIES name="SpSTANDARD" defaultvalue="0"/>
  </SPECIES_TABLE>
</DEFINITION>
<!-- ================================================= -->
<!-- Messages                                           -->
<!-- ================================================= -->
-<MESSAGES>
  <MESSAGE family="FmNIBP" genus="GnREQUEST" species="SpGET_DATA" defaultvalue="128" version="100"/>
  <MESSAGE family="FmNIBP" genus="GnREQUEST" species="SpGET_CONFIG" version="100"/>
  <MESSAGE family="FmNIBP" genus="GnRESPONSE" species="SpPUT_DATA" version="100"/>
  <MESSAGE family="FmNIBP" genus="GnRESPONSE" species="SpPUT_CONFIG" version="100"/>
  <MESSAGE family="FmNIBP" genus="GnCOMMAND" species="SpWRITE" version="100"/>
  <MESSAGE family="FmNIBP" genus="GnSTATUS" species="SpREPORT" version="100"/>
  <MESSAGE family="FmNIBP" genus="GnSTREAM" species="SpSTREAM" version="100"/>
  <MESSAGE family="FmNIBP" genus="GnCOMMAND" species="SpEXECUTE" version="100"/>
</MESSAGES>
</FAMILY>
```

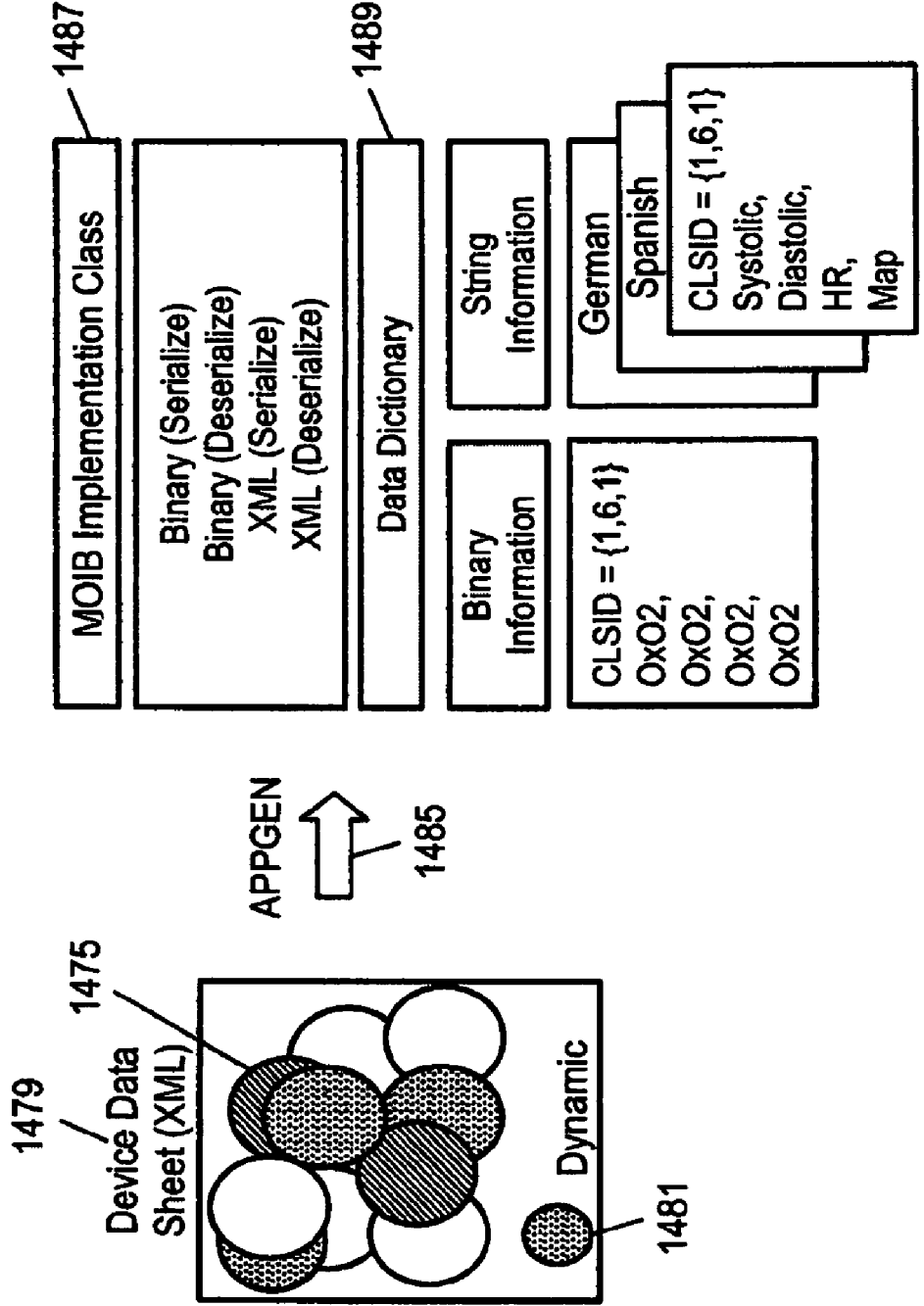

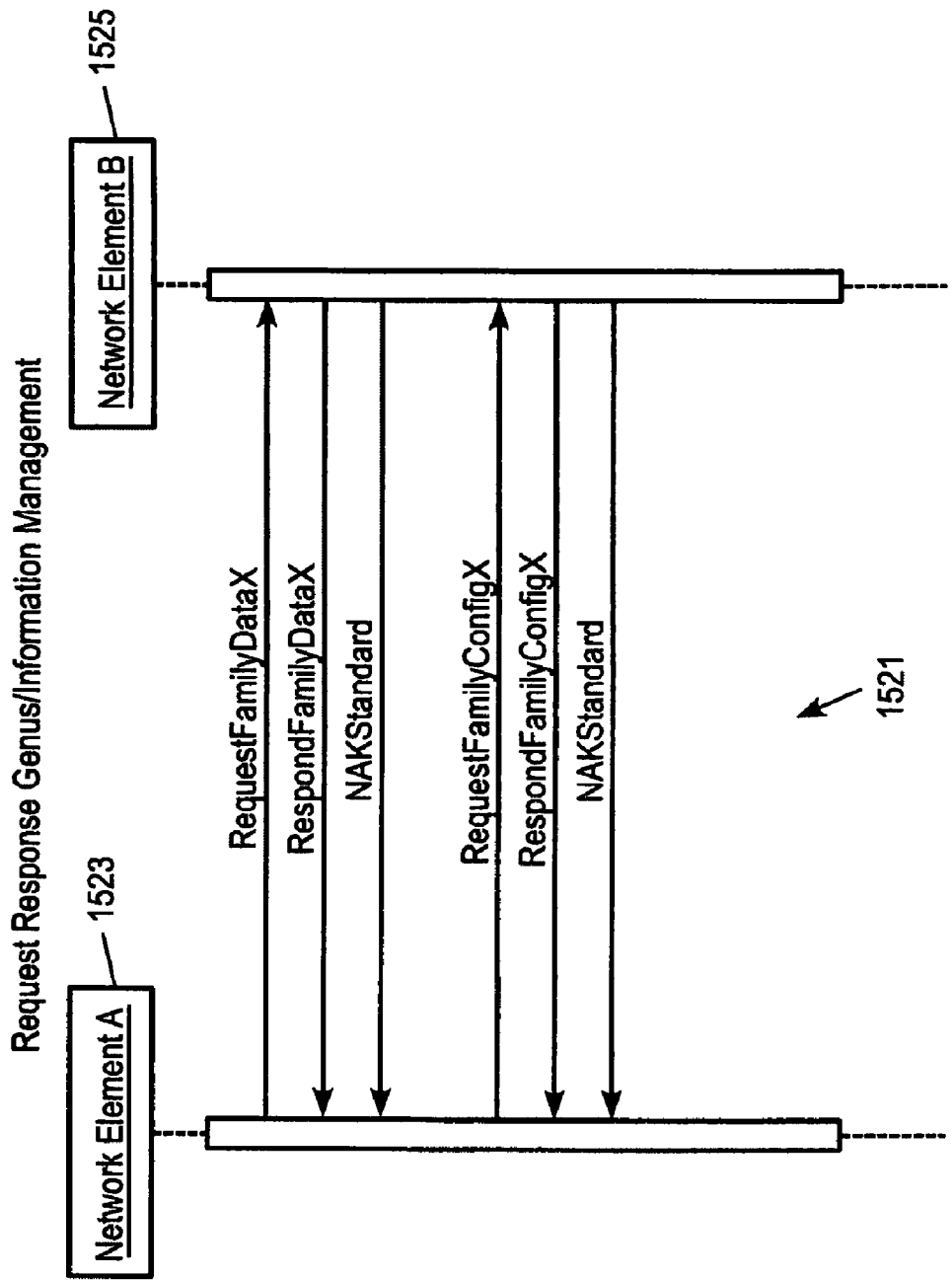

FIG. 9C

| | | | DICTIONARY TABLE - NIBP | | | | | |
|---|---|---|---|---|---|---|---|---|
| 1 | 6 | 1 | 0x02y | 0x02y | 0x02y | 0x02y | 0x01y | |
| 1 | 6 | 1 | Name | AKA | V 1.0 | | | |
| 1 | 6 | 1 | Item 1 | 1.0 - Cur | Name | Units | Scale | AKA |
| 1 | 6 | 1 | Item 2 | 1.0 - Cur | Name | Units | Scale | AKA |
| 1 | 6 | 1 | Item 3 | 1.0 - Cur | Name | Units | Scale | AKA |
| 1 | 6 | 1 | Item 4 | 1.0 - Cur | Name | Units | Scale | AKA |

| | | | DICTIONARY TABLE - NIBP | | | | | |
|---|---|---|---|---|---|---|---|---|
| 1 | 6 | 1 | 0x02y | 0x02y | 0x02y | 0x02y | 0x01y | |
| 1 | 6 | 1 | Name | AKA | V 2.0 | | | |
| 1 | 6 | 1 | Item 1 | 1.0 - Cur | Name | Units | Scale | AKA |
| 1 | 6 | 1 | Item 2 | 1.0 - Cur | Name | Units | Scale | AKA |
| 1 | 6 | 1 | Item 3 | 1.0 - Cur | Name | Units | Scale | AKA |
| 1 | 6 | 1 | Item 4 | 1.0 - Cur | Name | Units | Scale | AKA |
| 1 | 6 | 1 | Item 5 | 2.0 - Cur | Name | Units | Scale | AKA |

| | | | DICTIONARY TABLE - NIBP | | | | | |
|---|---|---|---|---|---|---|---|---|
| 1 | 6 | 1 | 0x02y | 0x02y | 0x02y | 0x02y | 0x01y | |
| 1 | 6 | 1 | Name | AKA | V 3.0 | | | |
| 1 | 6 | 1 | Item 1 | 1.0 - Cur | Name | Units | Scale | AKA |
| 1 | 6 | 1 | Item 2 | 1.0 - Cur | Name | Units | Scale | AKA |
| 1 | 6 | 1 | Item 3 | 1.0 - Cur | Name | Units | Scale | AKA |
| 1 | 6 | 1 | Item 4 | 1.0 - 3.0 | Name | Units | Scale | AKA |
| 1 | 6 | 1 | Item 5 | 2.0 - Cur | Name | Units | Scale | AKA |

1573 ↙   1575

DEVICE DATA SHEETS AND DATA DICTIONARIES FOR A DYNAMIC MEDICAL OBJECT INFORMATION BASE

CROSS-REFERENCE TO RELATED APPLICATIONS

The present application claims priority to U.S. Provisional Patent Application Ser. No. 60/848,993, filed Oct. 4, 2006 and titled "Dynamic Medical Object Information Base", which is hereby incorporated by reference in its entirety. The present application incorporates by reference in their entireties U.S. Provisional Patent Application Ser. No. 60/667,203, filed Mar. 30, 2005, U.S. Provisional Patent Application Ser. No. 60/787,147, filed Mar. 28, 2006, and PCT Application US2006/011373, filed Mar. 30, 2006.

FIELD OF THE INVENTION

This invention relates generally to methods, apparatus and systems for the communication of information among a plurality of network elements, and specifically to a dynamic medical object information base for interoperability of devices and systems.

BACKGROUND OF THE INVENTION

Varied computing environments may exist with vastly different requirements for acquisition, communication and storage of data depending on particular requirements of specific situations. In particular, some computing environments may require acquisition and communication of large volumes and varieties of data definitions. Furthermore, the requirements of many computing environments may change and evolve over time. An illustrative example of a computing environment that requires the acquisition and communication of large volumes and varieties of data definitions with requirements that change and evolve over time may be a health care computing environment. Other examples in other fields also require the acquisition and communication of large volumes and varieties of data definitions with requirements that change and evolve over time.

For example, a health care computing environment may include a variety of medical monitoring and analysis devices that process physiological data and communicate the physiological data via a network. The physiological data may include subsets of physiological data depending upon the application. For example, subsets of physiological data may include heart rate, respiration rate, blood pressure, and many other subsets of physiological data. The medical devices may include one or more types of software, and the medical devices and software may be configured to operate upon a particular subset of physiological data. The particular subset of physiological data may be unique to a group of one or more medical devices. There may also be an overlap between particular subsets of physiological data that are processed by each group of one or more medical devices.

The design of each medical device, or any other machine performing health assessment, is dependent upon the particular subset or subsets of physiological data that the medical device or other machine processes and communicates. The design of the software residing on the medical devices is also dependent upon the subset or subsets of physiological data or clinical outcomes that the medical device processes and communicates.

Electronic medical systems encompass devices and other clinical knowledge bases. Therefore, they must be capable of taking on the traits of highly adaptive, interpretive, and complex systems continually evolving. As medical knowledge deepens there are changes in how medicine and medical practice are defined. This includes physiology captured by devices as well as clinical analysis. It is important that a method for defining and communicating medical information is extensible and flexible. This is true of any other evolving or adapting environment.

As a result of the complexity found in medical electronic systems and other complex systems, a substantial effort may be required to design, implement and maintain software that acquires and communicates physiological and/or other types of similar data. Over time the effort to design, implement and maintain this software is both cost and labor intensive. Additional substantial effort may be required when the software is developed to execute on a plurality of interoperating devices, with the plurality of devices operating upon unique and/or particular subsets of data. The software may then be required to operate on multiple subsets of data characterized by distinct data types and associated data definitions. Substantial effort may also be required where the data, including the data types and associated data definitions, may be subject to change and evolve over time. Substantial effort may also be required where the data, including the data types and associated data definitions differentiate from one device to the next due to targeted clinical use or level of user.

Software reliability may be critical in a variety of fields, but is particularly critical to providing adequate health care. Therefore, substantial efforts are required where software operates upon data within a health care environment. Lack of reliable software interoperability within a health care environment may interfere with providing adequate health care and may harm or even kill health care patients.

Needs exist for improved communications protocols for acquisition and communication of data between network elements. Needs also exist for methods for interoperability of devices and systems.

SUMMARY OF THE INVENTION

Embodiments of the present invention solve some of the problems and/or overcome many of the drawbacks and disadvantages of the prior art by providing methods, apparatus and systems for interoperability of devices and communication systems.

Certain embodiments of the invention accomplish this by providing methods including initiating a communication link with a network device, receiving standard device data from the network device comprising a global unique identifier, and requesting a self-describing data dictionary from the network device, wherein the self-describing data dictionary comprises one or more data definitions.

Embodiments of the present invention may include receiving the self-describing data dictionary from the network device in response to the request by matching the global unique identifier with a cached version of the self-describing data dictionary and accessing the cached version of the self-describing data dictionary and/or a corresponding member of a self-describing data dictionary database on a storage device or the Internet and accessing the self-describing data dictionary. The self-describing data dictionary may be used to further communicate with the network device. The self-describing data dictionary may be used to interpret data from the network device. The self-describing data dictionary may also include a string table corresponding to the data definitions wherein the self-describing data dictionary further includes a link table corresponding to the data definitions and string table.

Embodiments of the present invention may include a computer-readable medium carrying one or more sequences of instructions for controlling communications between one or more network devices, which instructions, when executed by one or more processors, cause the one or more processors to carry out the steps of: receiving a data dictionary corresponding to a network device wherein the data dictionary is derived from a device data sheet, and wherein the data dictionary comprises one or more data definitions specific to the network device and a global unique identifier for the network device, receiving data from the network device, accessing the one or more data definitions from the data dictionary, extracting information from the data according to the data dictionary, and processing the information.

Embodiments of the present invention may include applying attributes from the data dictionary to the extracted information. The one or more data definitions may be standard definitions regulated by a standard setting organization accessed from storage in a collection of definitions.

In embodiments of the present invention the device data sheet may be XML compiled to source by an application generator. Embodiments of the present invention may include serializing and deserializing byte streams of information wherein the serialization provides a built-in protocol bridge between binary and XL network devices and/or serializing and deserializing XML wherein the serialization provides a built-in protocol bridge between binary and XML network devices.

The data dictionary may be created from a device data sheet converted to binary form.

Embodiments of the present invention may be a tangible medium containing instructions for communicating with a network device, the instructions executing a method including providing a communication protocol on a host computer for exchanging a series of messages between the host computer and a network device, initiating communication with the network device, receiving an acknowledgement from the network device, requesting a self-describing data dictionary comprising one or more data definitions, receiving the self-describing data dictionary, updating the communication protocol on the host computer with the self-describing data dictionary, receiving data from the network device through the communication protocol on the host computer, and processing the data according to the one or more data definitions.

The data dictionary may be stored on at a location selected from the group consisting of the network device, the Internet, a storage media, and combinations thereof. The data dictionary may include a global unique identifier unique to the data received from the network device and based upon a device data sheet used to create the self-describing data dictionary. The series of messages between the host computer and a network device may be classified with a hierarchal classification scheme. The hierarchal classification scheme may include a first level, a second level and a third level wherein the first level defines a type of data, wherein the second level defines a type of action, and wherein the third level defines an object of the action. The one or more data dictionaries may include information specific to the data. The self-describing data dictionary may further include a link table correlating to the one or more data definitions wherein the self-describing data dictionary further comprises a string table correlating to the link table. The data may be displayed to a user after processing via linking the data to strings for display using a scale, units, a link table and an alias. One or more data dictionaries may be reserved standardized data types or may be dynamically defined. The dynamically defined data dictionaries may include version information. The communication protocol may be backward compatible with previous versions of the dynamically defined data dictionaries. The data may be numeric or waveform. The one or more data dictionaries may be binary or XML. The one or more data dictionaries may be compiled by an application generator.

Embodiments of the present invention may include a method of communicating between network devices embedded within a tangible medium and executed by one or more processors including providing one or more cached data dictionaries with a hierarchal classification scheme for data comprising a first level, a second level and a third level, wherein the first level defines a type of data, wherein the second level defines a type of action, and wherein the third level defines an object of the action, sending a communication request to a network device, receiving a response from the network device comprising identification information, and processing the response according to the one or more cached data dictionaries.

Embodiments of the present invention may further include sending a request for one or more additional data dictionaries to the network device and receiving the one or more additional data dictionaries, adding information from the one or more additional data dictionaries into the one or more data dictionaries, receiving data from the network device and processing the data via the hierarchal classification scheme, and/or accessing standard data definitions based upon the identification information if the network device does not support self-description and the hierarchal classification scheme.

Users may generate a device data sheet that may be input into an application generator. Embodiments of the present invention may include a method stored in a tangible medium and executed by one or more processors including accepting information on whether one or more data definitions are needed in a software project, accepting information on whether one or more string tables are needed in a software project, accepting information on whether one or more link tables are needed in a software project, creating one or more files selected from the group consisting of data definitions, string tables, link tables and combinations thereof, collecting the one or more created files, compiling the one or more created files with an application generator, and outputting resultant source code from the compiling.

Embodiments of the present invention may further include incorporating the resultant source code into a software development product, creating new data definitions if one or more additional data definitions are needed, and/or reusing existing data definitions if one or more additional data definitions are needed. The one or more data definitions, one or more string tables and one or more link tables may be XML files. The one or more string tables may be software development project specific. The one or more link tables may be software development product specific. The one or more data definitions may further include a header wherein the header further comprises values for data type, action and object of action. The one or more data definitions may further include an XML text section. The one or more string tables may further include a symbolic link translation table and a string block and the string block may be null-terminated.

Embodiments of the present invention may include a method stored in a tangible medium and executed by one or more processors for generating a data dictionary from a device data sheet including creating one or more data definitions for a specific project, collecting the one or more data definitions in an XML formatted device data sheet, compiling the one or more data definitions in the XML formatted device data sheet with an application generator, outputting source code.

Embodiments of the present invention may further include creating a string table and compiling the string table with the device data sheet and/or creating a link table and compiling the link table with the string table and the device data sheet.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings:

FIG. 1A shows an adaptive communications framework for complex systems.

FIG. 1B shows management of complex communications systems.

FIG. 1C shows an overview of the communications protocol of the present invention.

FIGS. 6A-6E show various aspects of framework family taxonomy.

FIGS. 8A-8L show various aspects of serialization of messages using the communication protocol taxonomy.

FIGS. 9A-9G show various aspects of processing serialized messages by architectural structures.

DETAILED DESCRIPTION OF THE INVENTION

Figure 1D:
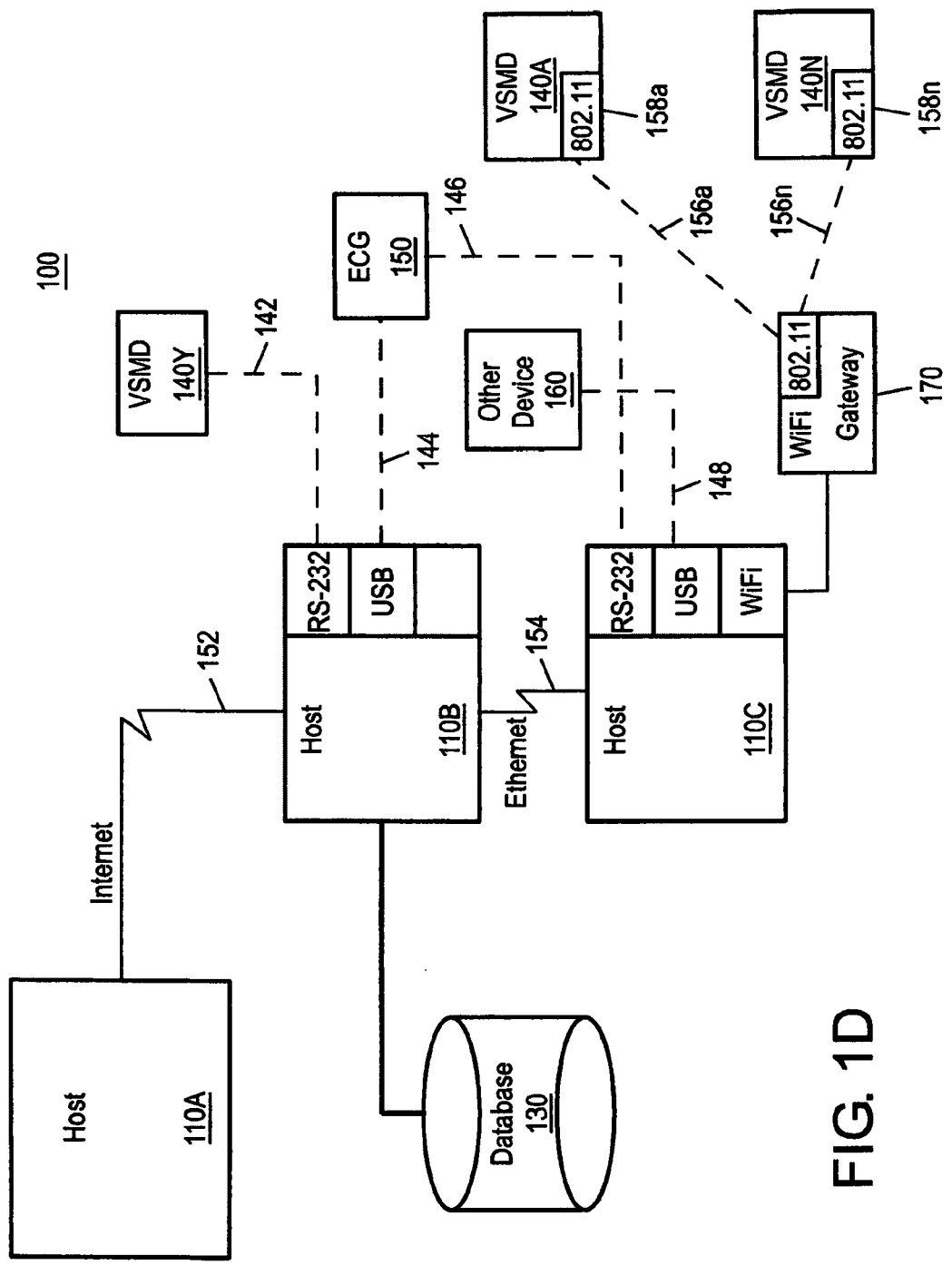
FIG. 1D is a block diagram illustrating various network elements located within health care or medical information system.

Some embodiments of the invention are discussed in detail below. While specific examples of embodiments may be discussed, it should be understood that this is done for illustration purposes only. A person skilled in the relevant art will recognize that other components and configurations may be used without parting from the spirit and scope of the invention.

FIG. 1A represents a new frontier for medical industry. The paradigm shift depicted may be a trend towards a customer or consumer driven model of self-guided healthcare. This new frontier may likely require interoperability and seamless communications. The internet and other technology have provided a mechanism for self-guided healthcare where patients may become more active in their own health management. This has given rise to a new concept, a personal health record (PHR) 17.

The PHR 17 may be an electronic record of health information managed by a patient. Health, lifestyle, and disease management may become an important method to improve quality of life and reduce costly hospital stays, potential harm and/or death. The system 11 of FIG. 1A shows a potential future healthcare environment as evidenced by current trends. A consumer market 13 may include healthy lifestyles 31, wellness checking 33, body networks 35, and self-guided care 37. The consumer market may further include lifestyle management, disease management, and health education/behavior modification programs. The consumer market 13 applications may be home-based or remote. The consumer market 13 applications may be self-initiated or prescribed by a healthcare professional in cases where disease management and monitoring are required. A professional caregiver 15 may act as a healthcare partner or manager of an individual or family PHR. Primary caregivers 29 may provide support for the management of the individual's PHR 17 directly and/or through a mobile health assistant 39.

Interoperability may enable the existence of the PHR 17. The PHR 17 may then provide for service-based systems in a health enterprise 19. Services in the service-based systems may include disease management 21, situation management 23, decision support 25, and family health and activity monitoring 27. Interoperability may facilitate communication and aggregation of the information in a PHR 17, and may further functionality of devices, systems, and consumer products such as cell phones and lifestyle devices such as health and fitness equipment. Interoperability may involve many industries outside of the medical industry. Many of these industries are not currently regulated and may be involved with different technology lifecycles that are incompatible with the technology lifecycles in regulated industries such as the medical device industry.

Interoperability may be required to fully realize the concepts of FIG. 1A. There may be diverse players in this space. To realize the opportunities in this system an adaptive framework approach may be required to allow building of applications without costly standards management. The traditional standards-based approach is time consuming and often lags behind the technology curve. Thus, standards-based approaches may not be successful in this space. More importantly perhaps, costs of the standards-based approaches may be transferred by the healthcare industry to the consumer.

FIG. 1B represents a current approach to interoperability via standards and profile management, which demonstrates that there are numerous opportunities for better interoperable network communications. Today, providers 43 must converge with medical professionals and service providers to define use models 45 for their medical systems 41. Then providers 43 must develop standards and/or regulations 47 in a standards pool 55 for data structure and exchange as well as profiles for workflows using the data so that all manufacturers of products that communicate medical information can interact. Cost and other factors like bureaucracy and competitive barriers may prevent most providers from participating in the development of a standard or profile. This enables the proliferation of proprietary solutions that cannot be leveraged. Standards development may be expensive and may counter innovation by requiring companies to agree upon a single structure for data interoperability. Current standards approaches may also homogenize information into inefficient models that must be continuously revised over time. To evolve existing standards the same players, such as providers 43, profiling organizations 51 and standards development organizations 53, continuously and inefficiently manage change of standards as medicine evolves. Furthermore, medical device manufacturers must adhere to regulations, which may slow time to market. Current standards practice in the medical space may be unable to empower the inevitable change that needs to take place in healthcare. Standards management may be a barrier to realizing system interoperability.

Embodiments of the present invention include a framework solution providing a flexible base technology to allow for independent development of interoperable information without extensive standards management. A framework may be defined as a reusable structure for organizing any solution. A communication protocol as defined herein may provide a core framework for data representation and message communications in a consistent and extensible way regardless of application specifics. The dynamic system of the present invention may provide for information plug and play via an interpretation engine or virtual machine that can learn or perceive new structures of information regardless of the source of the definition. This may allow for players in the system to define models of information that are differentiated while still allowing for interoperability. This may reduce or eliminate the cost burden of manufacturers in traditional standards-based approaches by providing a platform that is independent of specific application needs. All providers in the space defined in FIG. 1A may build interoperable applications without requiring standards management involvement.

The diagram in FIG. 1C represents a concept of a framework 57 in the context of the present invention. Applications 59 may be coupled to the foundation framework 57. The present invention may define two framework attributes. The first attribute may be communications 61. The communications framework may be a specification for the extensible modeling of information and the rules used to communicate the information in an open and interoperable environment. The first framework may provide for a foundation for the second.

Learning 63 may be the second attribute and may include the ability for one network device or machine 65 to communicate its information model to another by providing a decipherable dictionary and an interpreter. The interpreter may use the dictionary to extract information and act on it. Acting on the received information may depend on the goal of the application. It may display, store, combine and/or fuse the data with other data, run algorithms, or forward the data. To act on the data in this way the data dictionary must contain attributes allowing it to perform these functions, and the dictionary also may provide many attributes used to aid in the processing of the data.

The embodiment of this invention may be multifaceted. It may provide a modeling mechanism through which any machine can be modeled into a device data sheet (DDS). The model can be turned into a communicable data dictionary that can be deciphered by any other machines supporting an interpreter of the data dictionary, thereby enabling information interoperability.

The framework technology defined in this invention may enable the proliferation of application technologies as depicted in FIG. 1A without extensive standards management. The present invention may provide a more level playing field for all enablers in a complex system and the realization of improved lower cost healthcare through reduction of costs of the management of standards.

The present invention may provide a system for an intelligent framework based upon a Medical Object Information Base ("MOIB") and a Medical Object Management Protocol ("MOMP"). The following description describes use of a system for interoperability of medical devices on a network and particularly measurements of non-invasive blood pressure ("NIBP"), but it is understood that this example is merely illustrative and other uses and fields of use are contemplated. The present invention may be useful for any system with an evolving or adapting environment.

MOIB may include a dictionary and classification mechanism used to model information sets that represent human physiology or other information models. MOIB may define standard types representing information "primitives" supported by machines. For example, a primitive might be a simple numeric representing a systolic blood pressure reading or a fixed length string representing the model of a machine producing the reading. The field of medicine is a highly adaptive and complex system that is always evolving. As knowledge in the field increases there are shifts and changes in how information is described. Therefore, it is important that a method for defining medical information be extensible and flexible. This is similarly true of any evolving or adapting environment.

MOMP may include common message rules that allow machines to form "sentences" used to communicate information provided by MOIB. MOMP may have a set of standard message constructs forming a foundation of grammatical rules that may be understood by all openly communicating entities in a network to form a meaningful dialogue. An MOMP device may recognize a question and respond intelligently regardless of the subject. This may also be true for other messaging types defined by MOMP. There may be five fundamental message types that each machine in a MOMP/MOIB network may support: Request, Response, Command, Status, and Stream. Other message types may be defined depending on particular uses and needs.

MOIB and MOMP may be embodied in specifications of a computer language used to define information symbols and message rules. Inherent in these two specifications may be a semantic model that defines grammar or rules (MOMP) used to build common sentence structures as well as the machine information models (MOIB) representing the information machines communicate by using MOMP rules. A computer language may be modeled in this way so each device may be capable of intelligent and open communications regardless of the transport or communications pipe used.

MOIB and MOMP may be described as a computer language modeled after human language. Message constructs common to all constituents in a system may enable an open system of communication. As an example, an interaction between two devices may be a request for information. The ability to ask for information and comprehend a request may be the result of using grammatical rules to construct sentences. The end result may be a response with the information requested or a response acknowledging a lack of awareness of the information requested.

Machines in networks using the MOMP framework may be able to communicate openly with other constituent members and exchange intelligent answers even if subjects are not recognized. MOMP may provide rules, analogous to grammar, for all constituents in a network to use during open communication using rules of language engagement.

Symbols may define the information subject of the intended function of the machine. For example, a function of a medical device may be the definition of information specific to human physiology abstracted from the hardware process retrieving the information. Once this physiologic classification is complete the data may be symbolized by using a MOIB framework. As discussed, MOIB may be a specification defining physiology or any information model in an electronic form.

The combination of the MOMP and MOIB frameworks may allow the electronic exchange of data via intelligent dialogue.

Using the medical device example, in an NIBP device the NIBP information may be defined using the MOIB framework MOMP may be applied to define the messages that work with the NIBP information. If a computer were to ask an NIBP device for temperature, then the NIBP device, being trained, may respond signifying it does not support the information sought. If the computer were to ask an NIBP device for NIBP, however, then the NIBP device may respond with the information requested.

The MOIB and MOMP frameworks are implemented within network communication protocols such as interchange and "Rendezvous". An interchange specification may provide an enveloping mechanism for messages and data passed between constituent members in a system. An interchange specification can also track with whom a machine is carrying a dialogue.

Enveloping may be performed in a similar manner to the mechanisms for creating electronic sentences as described herein. The interchange specification may define unique strings called preambles or envelopes. The preamble may be a set of symbols that provides an electronic method for separation of messages for processing. Preambles are useful in instances when many messages are being received. The preamble may provide a mechanism by which a system can easily search for and test the integrity of messages as they are received from transport pipes. It may also provide the ability to separate and queue up messages for processing by applications using the communication protocol.

The preamble may also allow the system to identify domains of information. For example, a communication protocol may contain "WAL" and "WAC" preambles. WAL may be a light weight preamble marked by the "L" in "WAL" that is composed of a simple envelope only intending to carry simple clearly separated messages. "WAC" may be a more complex preamble that contains session-based information allowing large messages to be broken up into pieces. WAC preambles may contain additional information including packet ordering. The system using WAC preambles may be analogous to receiving a series of packages to be reassembled at the application layer. Large files can be transferred by the communication protocol. The "WAC" preamble can be used to provide the information providing a target machine the clues it needs to properly reassemble the package.

Additionally the preamble can be used to define application domains. This may allow a medical application to recognize medical communications as well as other defined domains. This may be beneficial for fire walling messages as well mixing data from multiple applications.

"Rendezvous" may be described as a handshaking protocol. The Rendezvous handshaking protocol may provide a process that first identifies that a device is a device running the communication protocol via a simple string followed by an optional negotiation of encryption keys. This may be followed by an optional exchange of a model of the frameworks used by the device to communicate information, which may be in the form of a data dictionary.

The following are examples of the use of a communication protocol that is structured using MOIB and MOMP frameworks.

FIG. 1D is a block diagram illustrating various network elements located within health care and/or medical information system 100. Embodiments of the present invention may be used with any type of information systems. A health care and/or medical information system 100 is chosen as an exemplary system. Network elements may include host or server computers 110A-110C, vital signs measuring devices (VSMDs) 140A, 140N, 140Y, electrocardiogram (ECG) devices 150 and/or other devices 160. The various network elements may constitute nodes within the health care and/or medical information system 100. The various network elements may perform a variety of different functions within the health care and/or medical information system 100.

The host or server computers 110A-110C may be stationary or non-mobile devices that accommodate a variety of optional hardware. Optional hardware may include hard disk drives, RAM memory cards and/or communication interface hardware to support Ethernet, WIFI, USB, serial communications interfaces, and any other communication interface hardware for communications between the host or server computers 110A-110C and other network elements.

VSMDs 140A, 140N, 140Y may be network elements used by operators to perform various vital sign related physiological measurements of a patient. For example, a VSMD 140A, 140N, 140Y may measure systolic and diastolic pressure, mean arterial pressure, pulse rate, temperature and/or pulse oximetry (SpO2) of adult and/or pediatric patients. A VSMD 140A, 140N, 140Y may communicate with other network devices, including a host or server computer 110A-110C via an RS-232 serial interface, a universal serial bus (USB) interface or WiFi wireless 802.11 communications interfaces.

In an embodiment of the present invention, a VSMD 140A or 140N may be a Welch Allyn Spot LXi VSMD. In this embodiment, the VSMD 140A or 140N may optionally use a wireless adapter 158a or 158n to wirelessly communicate via an 802.11 communications channel 156a or 156n. The communications channel 156a or 156n may connect the VSMD 140A or 140N to a WiFi gateway 170, and the WiFi gateway 170 may then communicate with another network element, for example containing a WiFi communications interface. For example, the VSMD 140A or 140N may communicate with a host or server computer 11C via the WiFi gateway 170. A VSMD 140Y may communicate 142 via an RS-232 serial communications channel to a host or server computer 110B.

Other devices, such as an ECG measurement device 150, may communicate 144 via a USB communications channel to a host or server computer 110B or may communicate 146 via an RS-232 serial communications channel to a host or server computer 110C. As shown in FIG. 1, another device 160 may communicate 148 via a USB communications channel to a host or server computer 110C.

The host or server computer 110B may also communicate with a remotely located host computer 110A via an Internet communications channel 152. The host or server computer 110B may also communicate with another host or server computer 110C via an Ethernet local area network communications channel 154. The host or server computers 110A-110C may be set up and connected in various configurations with various networking connections. The host or server computer 110B may be directly connected to a database 130 that functions as a repository of data. The database 130 may store and process data captured and processed by the health care and/or medical information system 100. Data from the health care and/or medical information system 100 may be defined and structured to represent numerous measurements of human physiology for a population of patients.

Figure 2:
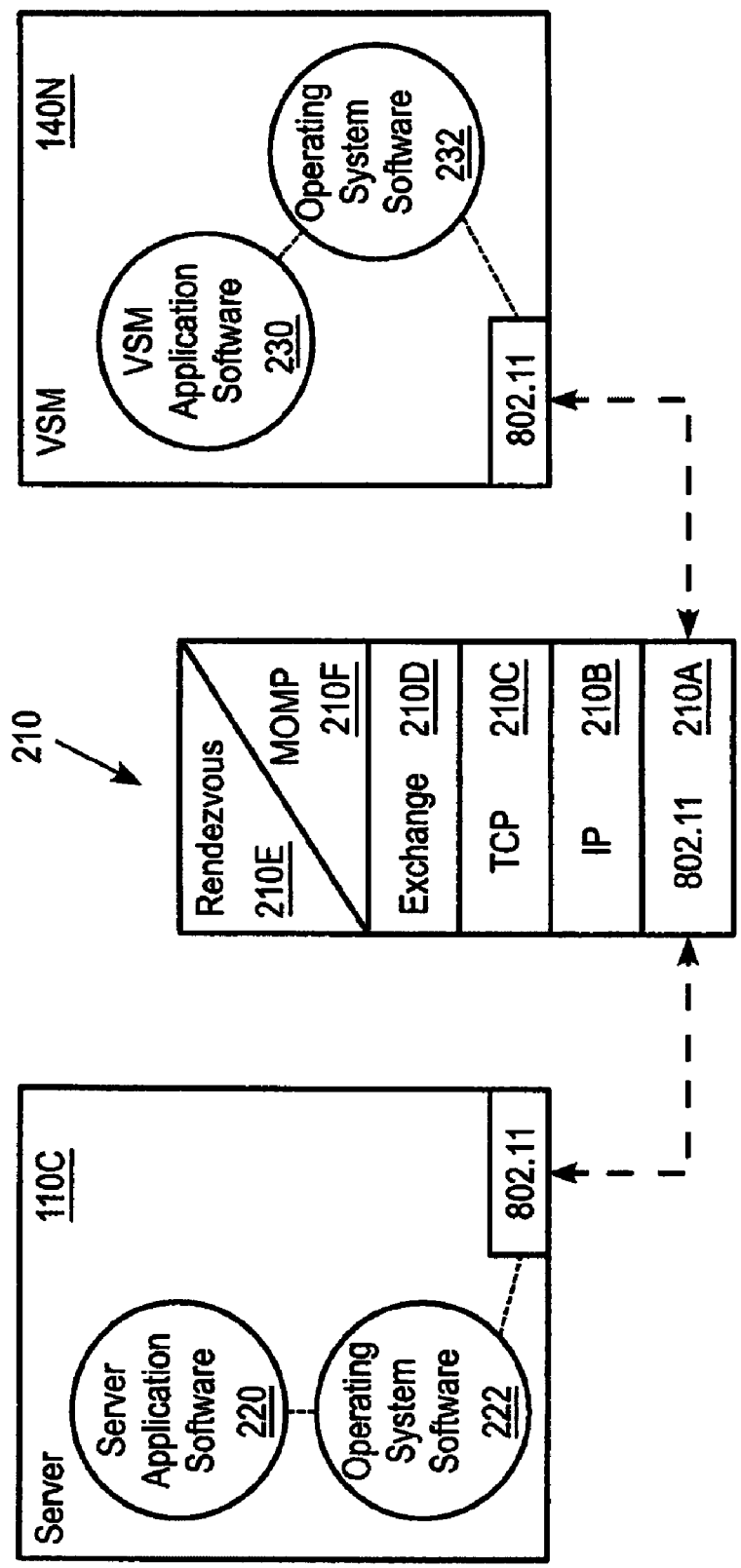
FIG. 2 is a block diagram illustrating a representation of internal software components and a communications protocol interface residing within a vital sign measuring device (VSMD) and a host or server computer as show in FIG. 1D.

FIG. 2 is a block diagram illustrating a representation of internal software components and a communications protocol interface 210 residing within the VSMD 140N and the host or server computer 110C, as shown in FIG. 1D.

A communications protocol interface 210, also referred to herein as a protocol stack, may include a layering or stack of communications protocols 210A-210F. The communications protocol interface 210 may be exercised between the VSMD 140N and the host or server computer 110C. Each communications protocol 210A-210F may be implemented as executing software within the communications protocol interface 210 for each network element. Each communications protocol 210A-210F may assist with the communication of information, including data that is acquired, stored and processed, by each network element of the health care and/or medical information system 100.

Each communications protocol 210A-210F may operate in accordance with a communications protocol interface (CPI) specification (not shown), also referred to herein as a CPI specification or communication interface specification. The CPI specification may be a tangible description of a communications interface. The communications interface is also referred to herein as a communications protocol interface (CPI). The CPI specification may be written, printed, digitally encoded, or other wise tangibly described.

The communications interface 210 may include a series of communication protocols 210A-210F. The lower three protocol layers 210A-210C may be exemplary. Protocol layer 802.11 210A, internet protocol (IP) 210B and transport connection protocol (TCP) 210C may be standard and well-known communications protocols that collectively constitute a lower portion of the protocol stack 210. The lower three protocol layers 210A-210C are also referred to herein as a lower protocol stack. The lower three protocol layers 210A-210C may be employed to support and carry the upper protocol layers 210C-210F. Protocol layers such as Interchange 210D, Rendezvous 210E and medical object management protocol (MOMP) 210F protocol layers are described in accordance with embodiments of the present invention.

Use of the lower protocol stack 210A-210C as described above may not be required, and may be modified in various ways to practice embodiments of the present invention. Other communications protocols, or combinations of communications protocols, can be substituted and/or combined with the communications protocols 210A-210C in various ways to support and carry the upper protocol layers 210D-210F.

The Interchange protocol layer 210D, also referred to herein as the Exchange layer or Interchange layer, may reside on a session layer of the Open Systems Interconnection (OSI) reference model and is preferably employed to carry the Rendezvous protocol layer 210E or the MOMP framework 210F. The OSI reference model is a layered, abstract description for communications and computer network protocol design, developed as part of the Open Systems Interconnection initiative. The OSI model divides the functions of a protocol into a series of layers. Each layer preferably has the property that it only uses the functions of the layer below, and only exports functionality to the layer above. A system that implements protocol behavior consisting of a series of these layers is known as a protocol stack or simply a stack. Protocol stacks can be implemented either in hardware or software, or a mixture of both. Typically, only the lower layers are implemented in hardware, with the higher layers being implemented in software. This OSI model is roughly adhered to in the computing and networking industry. Its main feature is in the interface between layers which dictates the specifications on how one layer interacts with another.

Server application software 220 may be located on the host computer 110C. The server application software may be configured to implement the upper protocol stack 210D-210F. Operating system software 222 may be located on the host computer 110C. The operating system software 222 may be configured to implement the lower protocol stack 210A-210C. Likewise, VSMD application software 230 may be located on the VSMD 140N. The VSMD application software 230 may be configured to implement the upper protocol stack 210D-210F. Operating system software 232 may be located on the VSMD 140N may be configured to implement the lower protocol stack 210A-210C. Other network elements may implement the protocol stack 210 in a same manner as described above.

Figure 3:
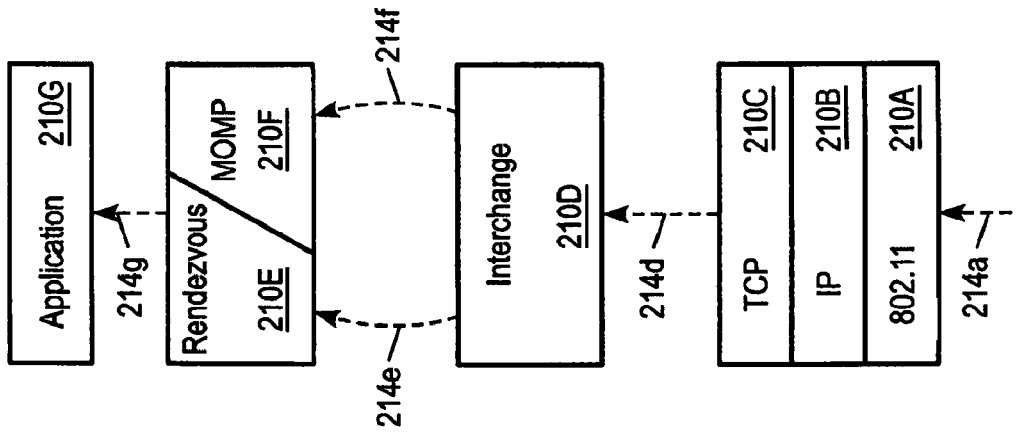
FIG. 3 is a block diagrams illustrating sending information from a network element through the communications interface.

FIG. 3 is a block diagram that illustrates transmitting information from a first network element to a second network element through the communications interface 210. When employing the communications interface 210 to transmit information, an Application layer 210G may initiate a transfer of information 212g, typically in the form of function call parameters, to the layer containing a Rendezvous protocol 210E and the MOMP 210F framework. The Rendezvous protocol 210E or the MOMP 210F framework may receive information depending on the particular circumstances of the information transfer.

In embodiments of the present invention, a function call parameter may include a pointer to a buffer of information to be transmitted via the communications interface 210. The next receiving protocol layer may transfer information to the Interchange layer 210D. Preferably, either the Rendezvous protocol 210E may transfer 212e information to the Interchange layer 210D or the MOMP framework 210F, may transfer information 212f to the Interchange layer 210D.

As just described, the information 212e or 212f may be input into the Interchange layer 210D from either from the Rendezvous protocol 210E or the MOMP framework 210F, respectively. The information input 212e from the Rendezvous protocol 210E may be related to establishment or termination of a connection with the second network element. The information input 212f from the MOMP framework 210E is preferably related to intelligent dialogue, based on rules of language engagement, with the second network element that was previously established by the Rendezvous 210E layer.

The interchange layer 210D may accept the inputted information 212e or 212f and then may output information 212d to the lower protocol stack 210A-210C. The information transfer 212d may be structured as an Interchange envelope that surrounds and includes either the information from the Rendezvous protocol 210E, which can originate from the Rendezvous protocol 210E or the MOMP framework 210F. For example, information transfer 212d to the lower protocol stack 210A-210C may include the information 212e when the information 212e is received and processed by the Interchange layer 212D, or may include the information 212f when the information 212f is received and processed by the Interchange layer 210D.

The lower protocol stack 210A-210C may accept the inputted information 212d and then may output information 212a for communication via a communications channel (not shown) to the second network element. The information 212a may include the information 212d in addition to protocol information added by software implementing the lower protocol stack 210A-210C.

Figure 4:
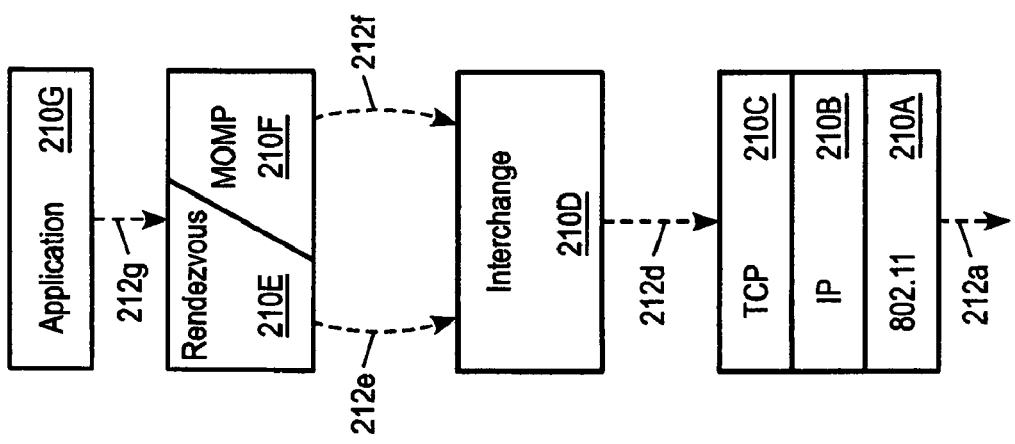
FIG. 4 is a block diagrams illustrating receiving information from a network element through the communications interface.

FIG. 4 is a block diagram that illustrates receiving information at a first network element from a second network element through the communications interface 210. The lower protocol stack 210A-210C may accept inputted information 214a transmitted from the second network element via a communication channel and related hardware (not shown). The lower protocol stack 210A-210C may process the information 214a and may then output information 214d to the Interchange layer 210D.

The Interchange layer 210D may accept and process the information 214d, and may then output or route information 214e to the Rendezvous protocol 210E or information 214f to the MOMP framework 210F. The routing of the information 214e or 214f preferably depends upon whether the information 214d is destined for the Rendezvous protocol 210E or the MOMP framework 210F. The information transfer 214d may be structured as an Interchange envelope that surrounds and includes information addressed to either the Rendezvous protocol 210E or the MOMP framework 210F. The Interchange layer 210D may remove information constituting the Interchange envelope.

The Rendezvous protocol 210E and the MOMP framework 210F within the Rendezvous layer may each input and process information received from the Interchange protocol layer 210D. Either the Rendezvous protocol 210E or the MOMP framework 210F may output or route information to the Application layer 210G.

Framework Taxonomy and Framework Structures Reflecting the Taxonomy

Embodiments of the present invention may include mechanisms to define information and messaging according to taxonomic classifications. A taxonomy may define standard types of MOMP and MOIB framework elements or dynamic types of MOMP and MOIB framework elements that depend on self-description to function.

The framework supports two atomic types of framework elements as defined below. Both types are described within the framework taxonomy for MOMP and MOIB.

Standard Atoms may be those objects in a particular family of the taxonomy, as described below, which are classified as standard information and are fixed in format. For devices that are unable to support self description due to overhead, these types may provide set members of a family that interoperate without a data map.

Other standard atoms may be objects that represent a classification type of information like a numeric or a waveform. They may be controlled in a contractual manner.

Dynamic atoms may be objects in a particular family of the taxonomy, as described below, which use self-description in the form of a transferable data dictionary based on MOMP and MOIB structures and nomenclature to achieve interoperable network communications. A message received by any device or hardware in a networked system may identify the data dictionary with which the message is associated. The receiving device may then select that data dictionary to extract information from the message and further process the information by mapping to link and string tables.

Framework Taxonomy

Taxonomy may be used as a mechanism to define information and messaging. Taxonomy can be defined as description, identification, and classification of a semantic model.

Taxonomy as applied to a classification scheme may be extensible. Taxonomy may logically separate information into families that can evolve. This correlates with semantic modeling because semantics is the study of changes in meaning and form. Changes in meaning and form may describe the behavior of information models in medical space or in any adaptive complex system where terminology is constantly evolving. Semantic class-based modeling utilizing taxonomy can minimize the complexity of data description management by limiting, categorizing, and logically grouping information management (symbols) and operational functions (messages) into families that contain both static and dynamic elements.

Figure 5A:
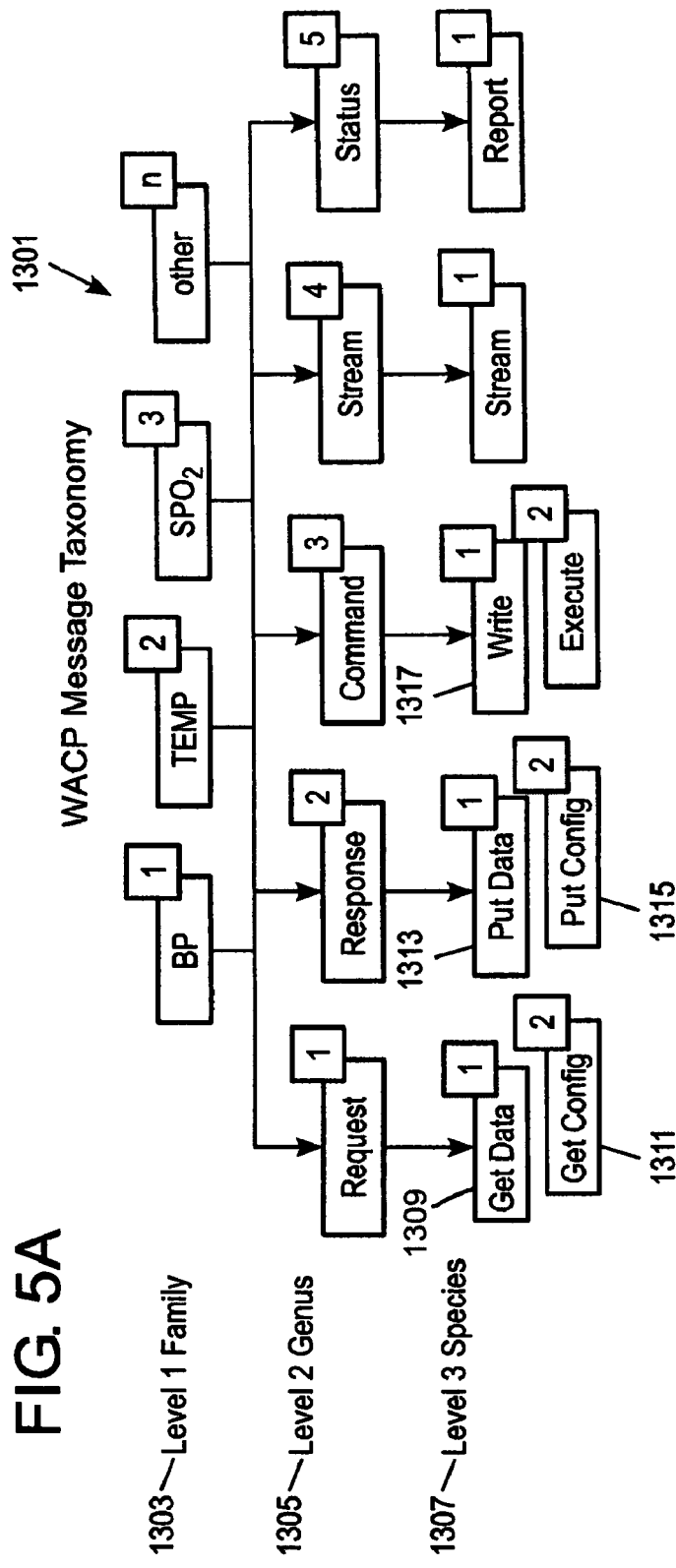
FIGS. 5A-5P show various aspects of standard family taxonomy.

FIG. 5A shows a taxonomic tree 1301 as a visual representation used to model messages in MOIB. The first level 1303 in FIG. 5A may represent a physiologic family of information. The first level, however, could be any family of information provided by a machine ("family"). The second level 1305 may define a semantic identity for a message ("genus"). The third level 1307 may represent a specific action the message represents ("species").

A computer language may use numbers to identify messages. The elements of the tree diagram 1301 in FIG. 5A may be combined in various sequences to provide unique numeric signatures for messages in all atomic families.

Figure 5B:
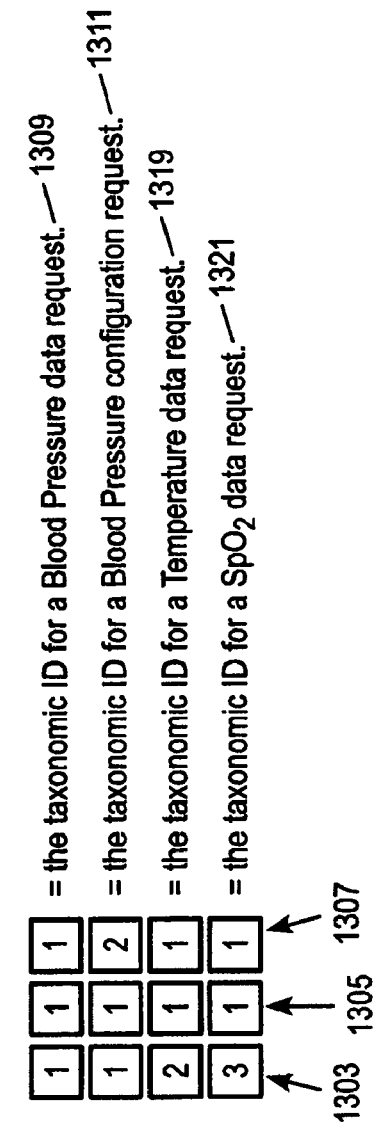

Using the taxonomy example, FIG. 5B shows that unique message IDs can be created that are identifiable by machines engaged in dialogue. Note that in each family the signature for a data request message 1309 may be the set of combined genus 1305 and species 1307 {1,1} regardless of the family 1303. Unique message IDs may be determined from FIG. 5A by first selecting a family message signature 1303, then selecting a genus message signature 1305 and finally selecting from a series of alternate species message signatures 1307. Examples of other genus 1305/species 1307 message signatures may be {1,2} for a configuration request 1311, {2,1} for data responses 1313, {2,2} for configuration responses 1315, and {3,1} for write commands 1317, etc. The genus 1305/species 1307 message signatures may be combined with any family message signature 1303. FIG. 5B illustrates several examples of possible combinations of message signatures and other combinations may be made by mixing and matching family 1303, genus 1305 and species 1307 message signatures. The identification provided in the combination of the message genus with the species may create a foundation for the message rules atomic families comprehend to carry out dialogue in an open communication system. The family identifier may represent any family of information supported in a machine. The signature for the message type, however, may contain the same signature for any information family defined.

Machines may be configured to recognize the message signature regardless of the family. Recognition of a subject from a predicate may allow a machine to ask for a definition when an unrecognized subject is discovered. This ability may add a dynamic aspect to the MOIB and MOMP frameworks. For example, {2,1,1} may represent a taxonomic ID for a temperature data request 1319 and {3,1,1} may represent a taxonomic ID for an SpO2 data request 1321.

Base dialogue rules may be simple constructs each physiologic family is required to support for data management/dialogue across machines. Machines may be trained on message signatures for open dialogue. Classified information atoms may be required to support the basic message management function, i.e., preferably all machines must support the request/response signature, status report message signature, write command, and streaming signatures. This may allow simple management of data and configuration for any device running the communication protocol. The sequence of FIG. 8H is an example of a standard message signature 1521 for communication protocol communications between network devices such as network element A 1523 and network element B 1525.

The message signature may define the predicate or actionable part of the semantic taxonomic model. The symbolic representation of information may also be defined.

Figure 5C:
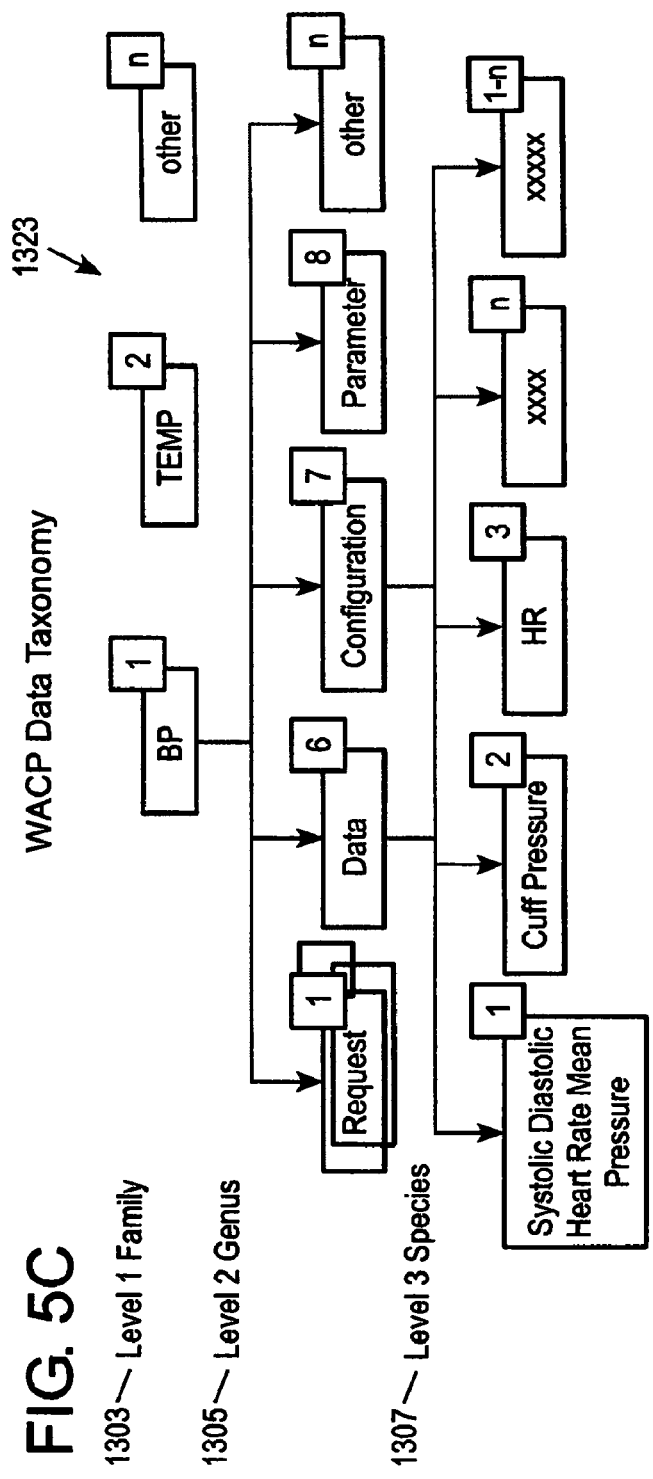

FIG. 5C defines an extension of the blood pressure family to the symbolic representation of information in the taxonomic model 1323. The first or family level 1303 in FIG. 5C may represent a family of information. The second or genus level 1305 may be expanded to define the semantic identity for multiple anticipated and/or unanticipated information types. The third or species level 1307 may represent the specific information represented.

Numbers may identify information. In the example taxonomic tree of FIG. 5C, the model may be expanded to define the information specific to an atomic family. There may potentially be many types of information in an atomic family. Some types of information may be sets of common information representing a grouping of information, while others may be simple types like a numeric. In each level the tree can be expanded as new information is discovered. Combining the numbers from each taxonomic level may provide a unique signature or marker for information representation in an atomic family. All machines may be made of atomic families of information. When combined, atomic families may provide a taxonomic signature of the device like DNA for living organisms.

Information signatures may be defined in atomic families. A machine may use these unique signatures to identify data in dialogue.

Figure 5D:
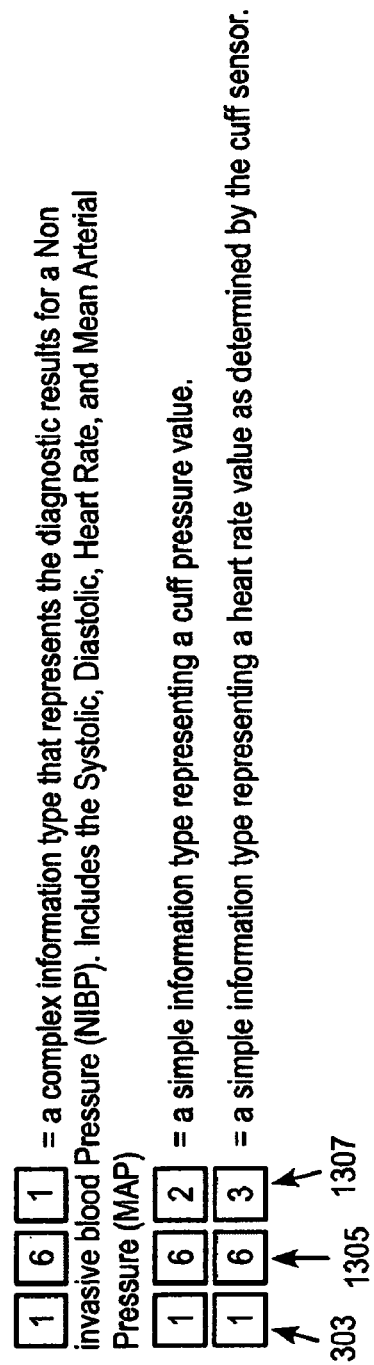

FIG. 5D shows information signatures. The first two values in the signature sequence may represent semantic symbolism for subject. The set {1,6} may represent an information part in the atomic family for blood pressure. Alternatively, the set {1,7} may represent a configuration part in the atomic family for blood pressure. Furthermore, the set {1,8} may represent a parameter part in the atomic family for blood pressure.

Figure 5E:
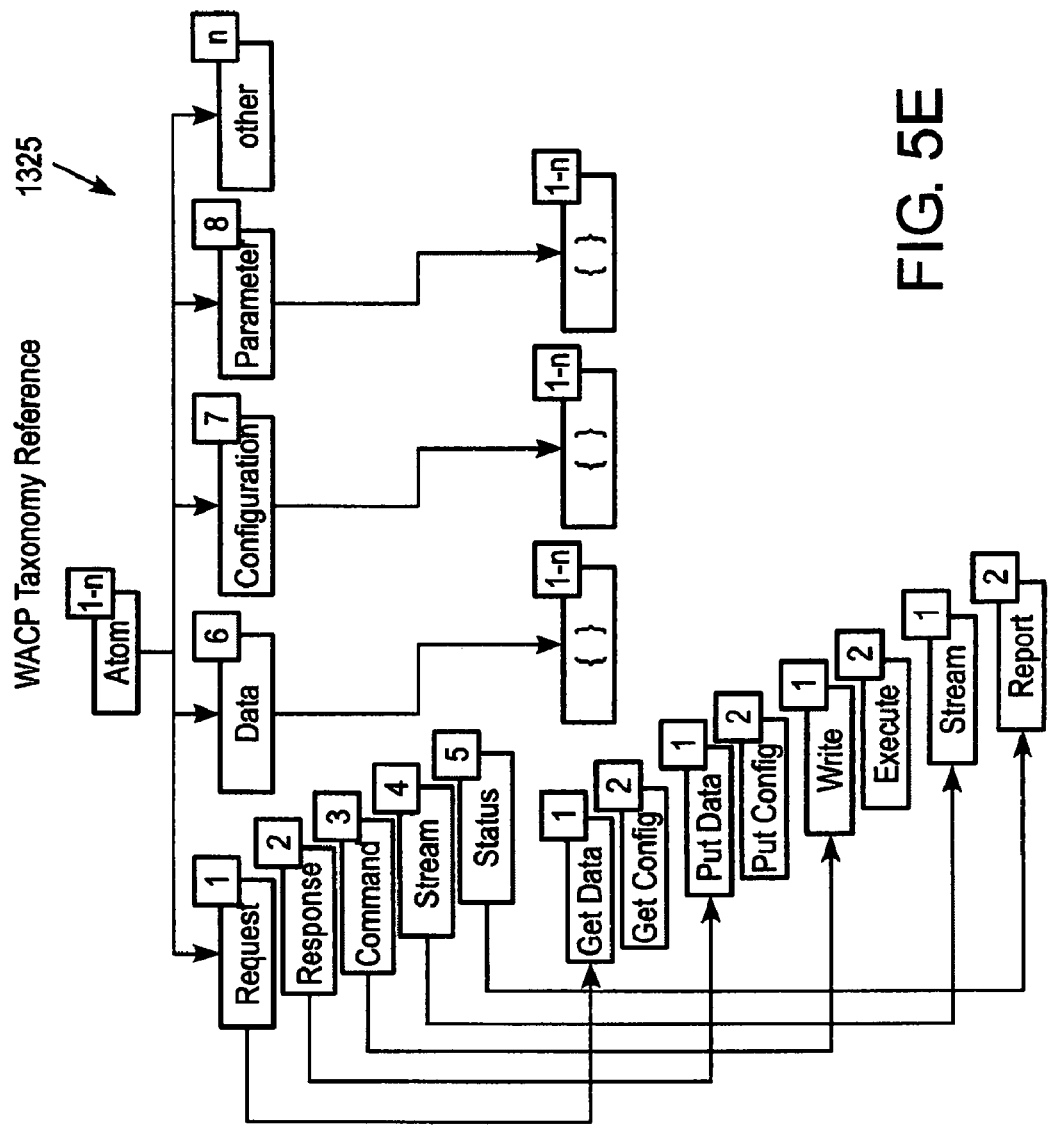

FIG. 5E illustrates a reference foundation for using MOMP and MOIB framework taxonomy in a communication protocol semantic model. All atoms of information may be modeled from this reference.

Each level of the taxonomy may be expanded for new discoveries and subsequent adaptation as information evolves. Hardware architectures may vary from machine to machine and from manufacturer to manufacturer. This may be due to customer requirements and marketing requests as well as the engineering capacity and investments in the physiologic hardware and software. Due to these differences, a single fixed definition of data structure is unlikely to span multiple devices. Hardware may dictate differentiation in the definition of diagnostic physiologic data as well as the configuration of the hardware and software systems that capture the physiologic data. For example, one blood pressure device may employ more complex hardware/software combination, which may produce a higher resolution pressure reading. An algorithm assisting in the calculation of the diagnostic results may provide configuration options that are more complex compared with another manufacturer's algorithms performing the same function.

Interoperability via prescriptive standard data structures or standards is problematic. Applications interacting with evolving devices may require expensive maintenance updates to understand the data structures and capabilities of devices made by various manufacturers. Communicating with multiple devices using different information models may result in increased complexity in the design of applications. Applications that gather physiology, program devices, or perform other interoperable functions may need to be rebuilt when device information models are changed during the course of device lifecycles. As new devices are introduced, consumers of machine data most likely must update applications to recognize new information models.

In contrast to the prescriptive standards paradigm, machines employing a communication protocol as described in the present invention may use numeric signatures to create a sentences consisting of a predicate and subject as in human dialogue. In the NIBP example, the numeric representations for both the message (rules) and the information (symbols) may be separated to create a machine readable sentence. FIG. 5F shows exemplary message structures, which may be used for a blood pressure based machine. These messages may be analogous with the predicate or actionable part of a sentence. The information defined in the NIBP example blood pressure family may be listed as a subject 1329.

Request/response dialogue may apply to both data and configuration requests and response sequences. Combining the predicate and subject may produce a machine readable sentence. A machine readable request sentence for "Give me your cuff pressure" may be a combination of elements 1331 and 1333 shown in FIG. 5G. After asking for the information a return response may result. Using the same method, a predicate with a subject may be combined to create the desired outcome. The expected outcome or response may be "My cuff pressure is N". To build a response it may be necessary to combine sequences 1335 and 1337 as found in FIG. 5H.

The request may carry the signature ID representing the requested information, in this example, the cuff pressure. The response, however, may carry the signature with the attached data, in this example, a value representing the cuff pressure. As mentioned earlier MOIB defines primitive types used to carry information as attached data.

In an open network any interrogating machine can manage any other. Management may mean the ability to solicit another machine for information openly. In the NIBP example, a response may be needed for the situation where the solicited device is not a blood pressure device. A no-acknowledge (NAK) may then be an appropriate response. Using the reference taxonomy, a set of messages and information representing an "I do not have the requested information" response may be defined. This response may be used to handle acknowledgement and no-acknowledgement. A trap family may be defined as an atomic family to deal with these situations. In its simplest form the trap family may have the ability to say "yes" or "no" in response to any message requiring feedback. A trap message may be a common construct used by all machines using the MOMP framework.

The "yes" and "no" message may also be capable of carrying information representing an extended reason why it can not perform a function. The "yes" or "no" message may include a machine based number that represents a reason code for the failure and human displayable text defining the failure. In a machine to machine request for data the device asked for information may return a "no" response carrying information in the form of a text string reading "System Busy" or "Data Unavailable". As a further example, an "Unsupported Family" response may result from an information request regarding an unsupported family. The reason codes may provide explanation beyond simple "yes" or "no" answers.

Recall that the machine may recognize the message signature for request as defined earlier. The machine may or may not support the family ID in the combined signature for the request. In FIG. 5I the machine may recognize the set {1,1} 1339 so it knows it is being asked a question. Looking at the family it mayor may not recognize the family (indicated by the "?" 1341). If the family is not recognized, the machine may resort to communicating a trap message. Information interoperability may break down in this example, however, dialogue based interoperability may not. The device only needs to ask for the definition of the family (?) to comprehend and ultimately act on the data.

FIG. 5J illustrates a taxonomy 1343 for common "yes" and "no" responses supported in a communication protocol-based dialogue.

Figure 5K:
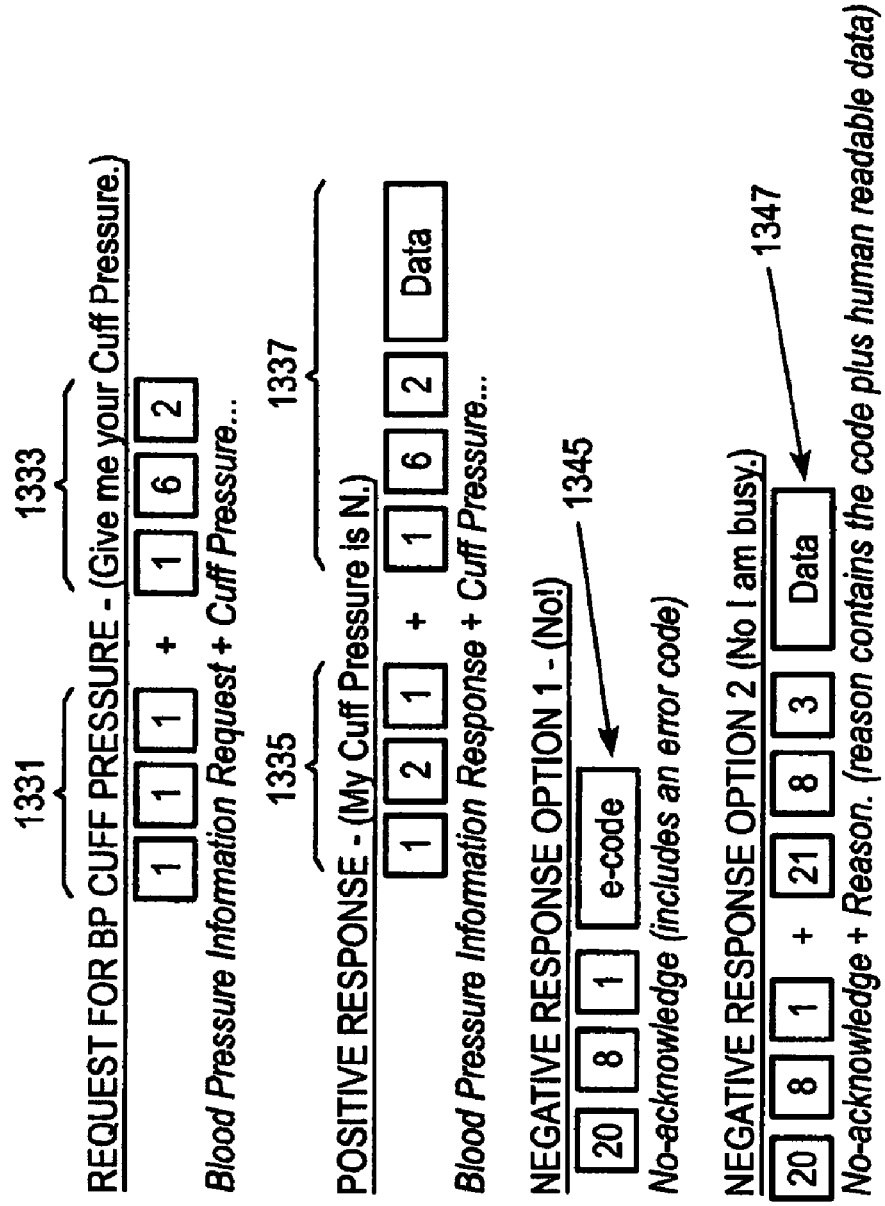
Figure 5L:
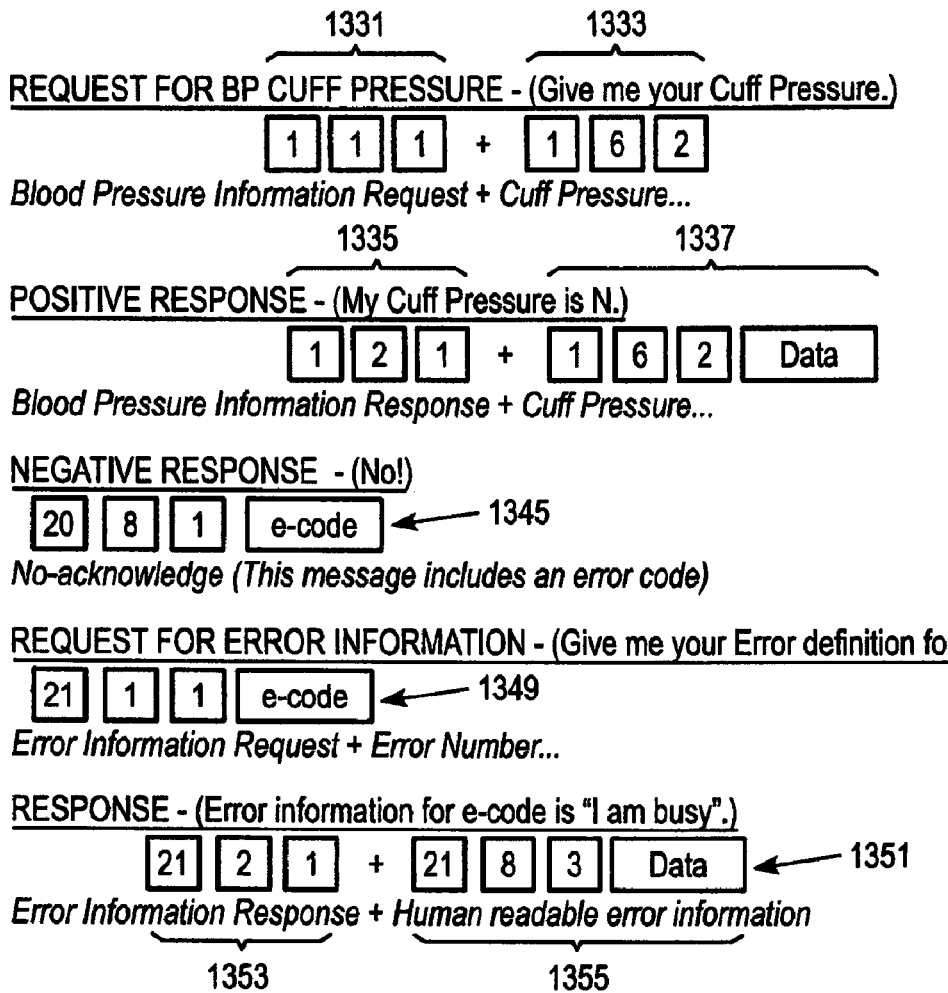

FIG. 5K shows an example of how a dialogue interaction in the communication protocol may be used. The machine to machine interaction in this sequence may be governed by the same rules as language engagement. The request may be the same request defined earlier, i.e., "Give me your cuff pressure". Each sequence in the dialogue may also be defined in human readable terms. The negative response Option 2 1347 may include an error code and error definition defining the specifics of the error. The negative response Option 1 1345 may also include an error code with it, but not the reason. The error family taxonomy may include a request and a response. This request response framework may allow a machine receiving a plain "no" response (Option 1 1345) without an error code to solicit 1349 and receive 1351 the reason from the "no" response. The response 1351 may include the sequences 1353 and 1355. An exemplary sequence is illustrated in FIG. 5L.

The source for accurate error information is generally the machine generating the error. In the past, systems error numbers have been supplied by the device while the machine receiving the error has been expected to map that error to a human readable definition of the error. This requires error code maintenance in network software that hosts multiple devices and versions of those devices. Extensive updates and resolution of error number overlaps (e.g. two devices may use an error code to define different states) may be required in systems that rely solely on error numbers as a means to map to human readable definitions. By leaving the error information in the device and supporting a standard error mechanism to retrieve it, costly updates and extensive error code management from host machines that interact with many devices may be eliminated.

Command stream and status message all behave similarly to the request message described above. Each message may carry information. Commands may send information with the intent to change the state. Status messages may carry information being reported at regular or irregular intervals requiring acknowledgement. A stream may carry continuously reported information, but it does not require acknowledgement like a status message.

Figure 5M:
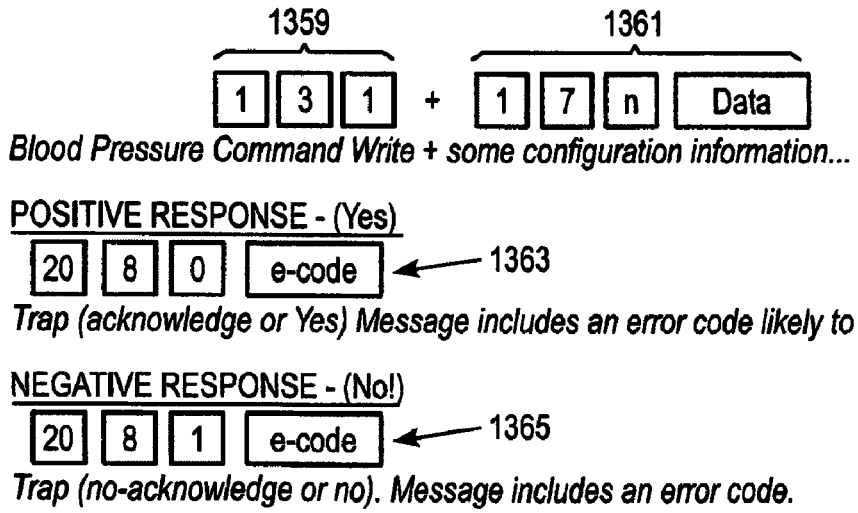

As with request and response messages, the taxonomic framework may be used to build communication regarding device configuration. To write configuration information to a device it may be possible to combine segments 1357, 1359 as in FIG. 5M. A positive response 1361 or a negative response 1363 may result.

The trap taxonomy may be used for all acknowledgement communications. The e-code returned can be retrieved from the device using the same mechanism as defined in the request response example provided earlier.

Command execute may provide a remote procedure call function. Execute messages may allow for a managing machine to invoke procedures on a device. Command execution functions may carry a string based message that represents the function a managing machine wishes to execute on a target machine. A genus-level taxonomic element may be provided to symbolize the execute command. The reference taxonomy may, for example, allocate the value eight for the genus parameter for the execute command.

Figure 5N:
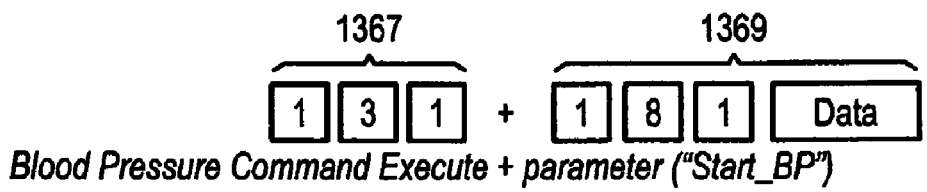
Figure 5N:
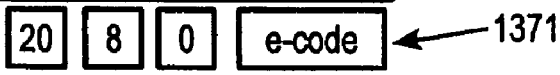
Figure 5N:
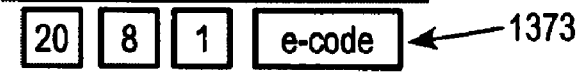

In the NIBP example, a start a blood pressure command may be desired. The sentence combination in the execute signature may be the simple sentence: "Execute the start BP cycle". The genus parameter in the signature may carry the command recognized by the machine as shown in FIG. 5N and made of segments 1367 and 1369. The machine may be required to respond with the outcome of the execution command; a positive response 1371 or a negative response 1373 may result.

Figure 5O:
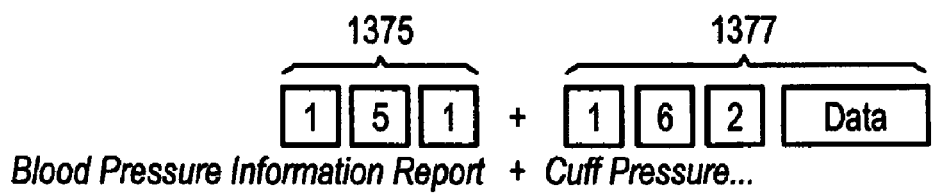
Figure 5O:
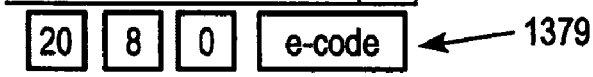
Figure 5O:
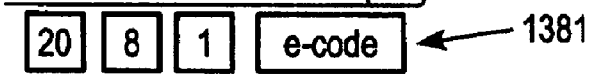

A machine may periodically report a cuff pressure (or any other information) during the NIBP process. This report may be invoked by a machine based process or from human interaction like the push of a send button on the machine with a status message as shown in FIG. 5O and made of segments 1375 and 1377. A positive response 1381 or a negative response 1383 may result.

Figure 5P:
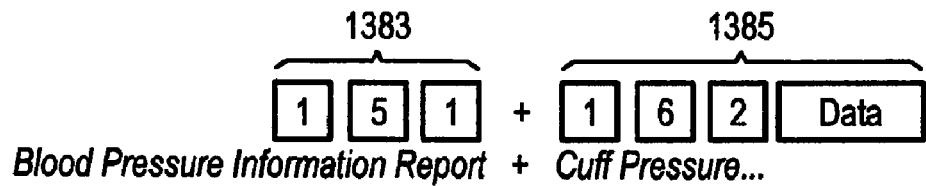

Streamed information may be time critical and continuous and may not require acknowledgment. In FIG. 5P a systolic reading from an invasive blood pressure monitor may stream to a target monitoring machine at some determined frequency made up of segments 1383, 1385.

Therefore, based upon the above examples, framework taxonomy may be applied to semantics to create a flexible rule-based computer language. Using framework taxonomy, numbers may be applied in a hierarchical fashion to provide a flexible and extensible mechanism for defining atoms of information in a machine. Each atom may be extensible at all levels of the taxonomy and may evolve independently over time. This may logically separate atoms of information into manageable sets that can be combined to create new atomic configurations of machine based organisms. This may provide the ability for machines to respond intelligently and understand the actionable part or predicate of all messages defined in the computer language's grammar.

MOIB may support defining standard types of data structures. The foregoing NIBP example is based on classifying data based on relevant physiologic families for purposes of the framework taxonomy. The example for this family has defined information and configuration for the atomic family of NIBP. For a medical manufacturer the definition of diagnostic data focuses mainly on physiology. In diagnostic function, atomic families of physiology, like blood pressure, temperature, height, weight, SpO2, ECG, etc. may be defined. These atoms may have data definitions, configurations, and messages. The MOIB framework for information modeling and identification may not be specific to just diagnostic data modeling at a physiologic level. There may be other taxonomies that are not based on families of types of physiologic data. These other categorical atoms may extend across physiologies representing a shared information model with a common consistent information set. The taxonomic framework/model may be capable of defining any categorical information. Categorical atoms can be mapped across all defined physiologies and may represent an information category like a numeric or wave sample. When examining blood pressure or SpO2, for example, numeric types may be classified with common attributes across the two physiologies.

Figure 6A:
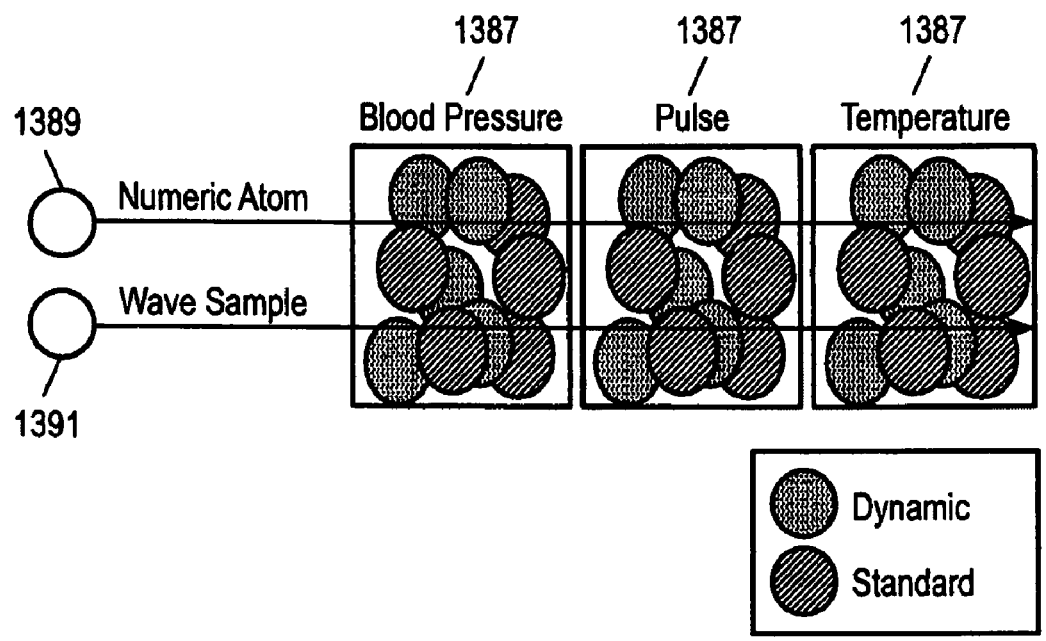

FIG. 6A illustrates the intersections between families of physiologic data structure types and categorical data types in the MOIB taxonomy. Each atomic family of physiologic data structure types may be set out vertically, while the families of categorical data structures may be set out horizontally. Each categorical family may include a cross sectional subset of data from each physiologic family. A categorical family may share information attributes as well as configuration attributes.

Categorical atomic families may be consistent with the framework taxonomic model and may be beneficial for a number of reasons. Management of an individual numeric sharing consistent traits in format may adhere to the classification taxonomy. Separating and defining numeric 1389 or waves 1391 solely within physiologic families of data may create a dispersed definition. This may open up the opportunity for errors introduced in the definition when updates are not executed across all families containing standard categorical types. It may also produce a deficiency in configuration taxonomy.

The classification of numerics solely in the family of NIBP physiologic data structures might take the following form. Notice that the numeric configuration is not clear in the taxonomic model.

Information Taxonomy NIBP
Aggregated data
FmNIBP::GnData::SpStandardReading
Numeric Data
FmNIBP::GnNumeric::SpSystolic
FmNIBP::GnNumeric::SpDiastolic
FmNIBP::GnNumeric::SpHeartRate
FmNIBP::GnNumeric::SpMeanArterialPressure
Configuration
FmNIBP::GnConfguration::SpStandardReadingConfig
FmNIBP::GnConfguration::SpSystolic (systolic "numeric" configuration?)
FmNIBP::GnConfguration::SpDiastolic (Diastolic "numeric" configuration?)
FmNIBP::GnConfguration::SpHeartRate (Heart Rate "numeric" configuration?)
FmNIBP::GnConfguration::SpMeanArterialPressure (MAP "numeric" configuration?)

There may be a taxonomic anomaly in applying a numeric in a vertical family of data structures. The model shown above may illustrate how the configuration of the numeric for each data numeric defined is not clear. There may be ambiguity in determining, for example, whether the SpSystolic species is applicable to a numeric or not. Even if a model were applied whereby the following is defined:
FmNIBP::GnConfguration::SpNumeric
Or
FmNIBP::GnConfguration::SpNumericSystolic There may be no clear method of identifying a numeric species within a family in the taxonomy. In the example directly above there is a clear overloading of species that violate the taxonomic process, thus adding complexity to species processing.

Each numeric data type may require its own configuration attributes, for example, limits. The definition in vertical physiologic families may not be capable of identifying the taxonomy as a configuration type for a specific species of a type of numeric. Any attempt made may tend to violate the taxonomic structure for family genus and species.

In attempting to mitigate issues like this taxonomic families of categorical data structures may be used. A preferred taxonomic model is detailed below. Notice the specificity in both data and configuration and the reuse of species to identify both the data and configuration.
Information Taxonomy Numeric
Data
FmNumeric::GnData::SpSystolic
FmNumeric::GnData::SpDiastolic
FmNumeric::GnData::SpHeartRate
FmNumeric::GnData::SpMeanArterialPressure
FmNumeric::GnData::SpTemperature
FmNumeric::GnData::SpSpO2
FmNumeric::GnData::Weight
Etc . . .
Configuration
FmNumeric::GnConfguration::SpSystolic
FmNumeric::GnConfguration::SpDiastolic
FmNumeric::GnConfguration::SpHeartRate
FmNumeric::GnConfguration::SpMeanArterialPressure
FmNumeric::GnConfguration::SpTemperature
FmNumeric::GnConfguration::SpSpO2
FmNumeric::GnConfguration::Weight
Etc . . .

The taxonomy in this model may clearly define the atomic members in a single family. Using a visual representation, the numeric family identification is shown in FIG. 6B. In both configuration 1393 and data 1395 the species may be the same and the taxonomy clearly defines what is represented in the atomic member. It may be expandable and can be maintained in a single atomic family.

Figure 6C:
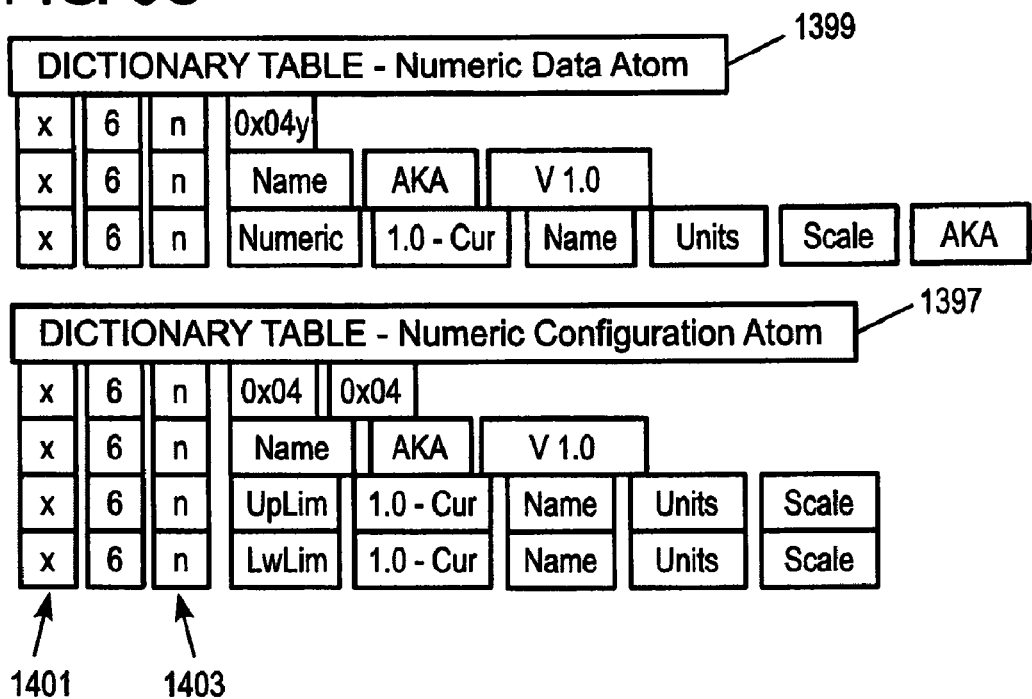

Categorizing information into atomic families that share a common function is advantageous for other reasons. A numeric configuration may carry the configuration limits for the numeric. Each numeric may have the potential to employ an upper and lower limit. Because the configuration for any numeric may be consistent the categorical atom can support a universal user interface that can handle any numeric. Atoms for configuration 1397 and data 1399 in the numeric family are defined in FIG. 6C. The value n 1401 may represent any species in the dictionary defined earlier. E.g. systolic=1, diastolic=2, heart rate=3, etc. The species value may be common to both data and configuration. The set {x,6,1} and {x,7,1} may represent the data and configuration for a systolic reading. The "x" 1403 may be a number representing the assigned numeric value for the "Numeric" atomic family.

Figure 6D:
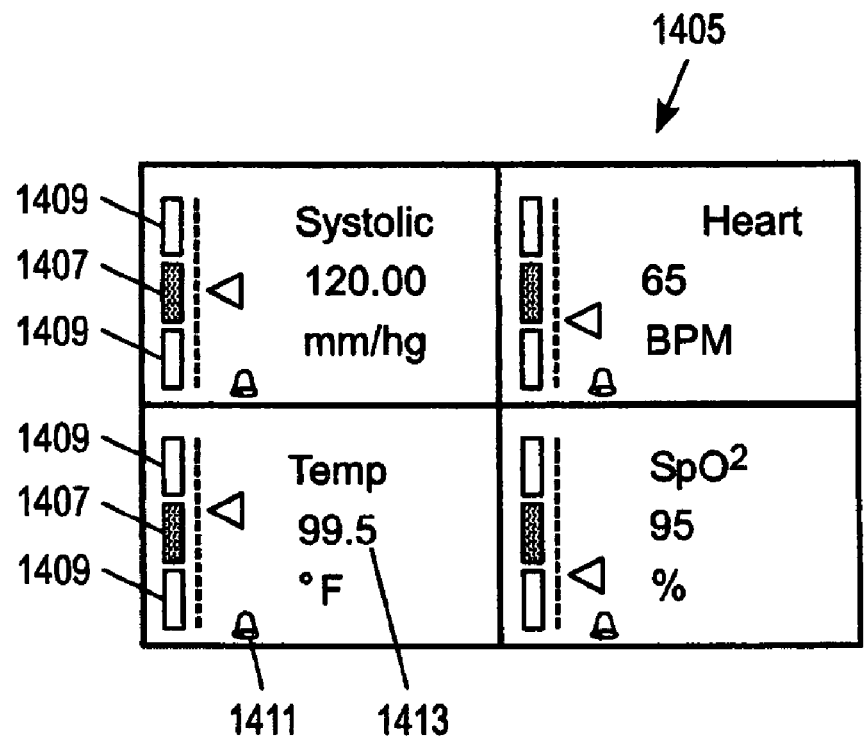

Using the numeric categorical atomic family, a user interface ("UI") can be constructed to support the taxonomic model. An example is shown in FIG. 6D. In FIG. 6D a single atomic framework family can be used to drive a smart user interface 1405. The user interface in this example may use the dictionary and reported configuration to handle any numeric encountered.

For the gage to fully function it may retrieve the device configuration for each numeric and apply it for each numeric. The gage may update as the reading changes. The slider gauges on the left may represent the current limit status. A green color indicator 1407 in the middle may represent a reading within limit and a red color indicator 1409 may represent a reading out of limit. If an out of limit condition is encounter the display may change a bell 1411 and the text 1413 to a red color for an enhanced visual cue.

Figure 6E:
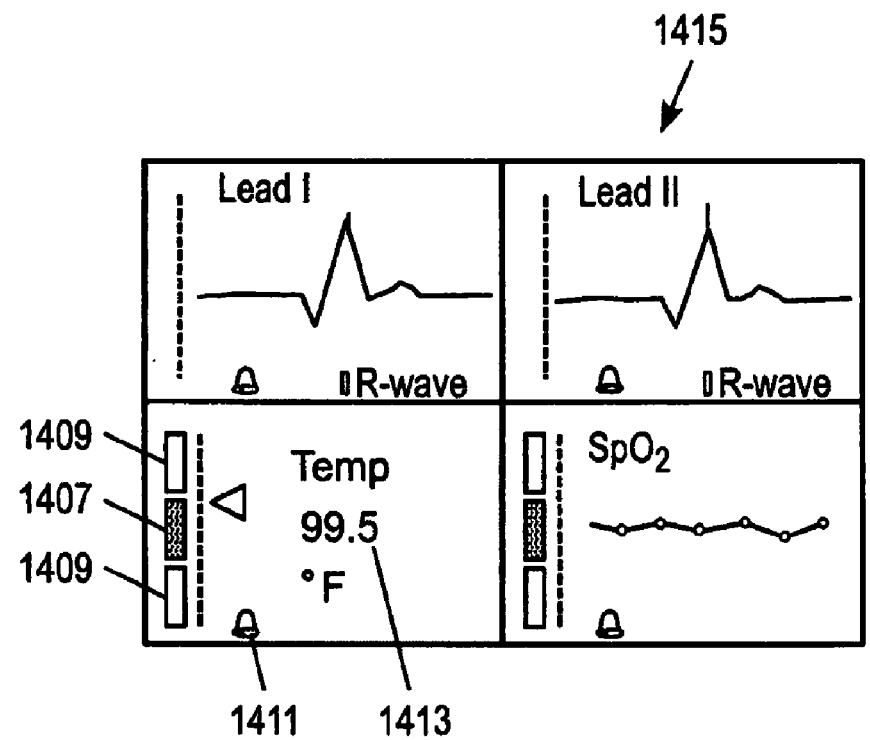

In addition to the numeric category type there may be a wave sample 1415 used to define wave information 1417. In FIG. 6E a similar UI concept is used to create a UI component for wave samples.

Standard framework types may provide a powerful mechanism for monitoring applications. A smart monitoring application may handle any machine discovered by utilizing standard smart UI interfaces linked to standard category atoms.

Dynamic Families and Dictionaries

The Dynamic Medical Object Information Base ("DMOIB") is an intelligence enabling technology that may allow machines to respond intelligently to changing interoperable environments by supporting the ability to comprehend new information models and entire machines.

DMOIB may be an implementation of MOIB providing a machine with the ability to describe a model and representation of information in an adapting evolving network.

DMOIB may utilize the taxonomic model from MOMP and MOIB and transform the taxonomic model into an electronic data dictionary. This data dictionary may be transferred from machine to machine in a simple learning process. Once the data dictionary is received it may be acted upon. In DMOIB action may be display or storage of information. The dictionary may carry the human readable representation of information including the definition, units of measure, scale for precision of numeric readings, as well as an aka ("also known as") for machine based processing algorithms. Providing this technique may allow for powerful self maintaining systems. The technology may provide a mechanism for adapting systems to change and interoperate with any device encountered under any changing condition through the discovery of machine dictionaries and information plug and play.

The data dictionary may be a standard C++ header file or another standard header file for another language that may use preprocessor macros available in the DMOIB implementation to create static byte-arrays of binary encoded data. These byte-arrays may then be managed by DMOIB in data dictionaries consumed by DMOIB implementation to produce fully dynamic data structures. On instantiation, DMOIB implementation may parse a data dictionary to create an internal list of data members. The data definitions may be completely system independent and portable across networks or file systems. The data dictionary definitions for each atom of information may provide the developer with the opportunity to load data definitions dynamically across a media connection provided by an MOMP stack or from a local file system. The data definition may be considered a "configuration" file that is available at run time instead of being needed at compile time.

Figure 7A:
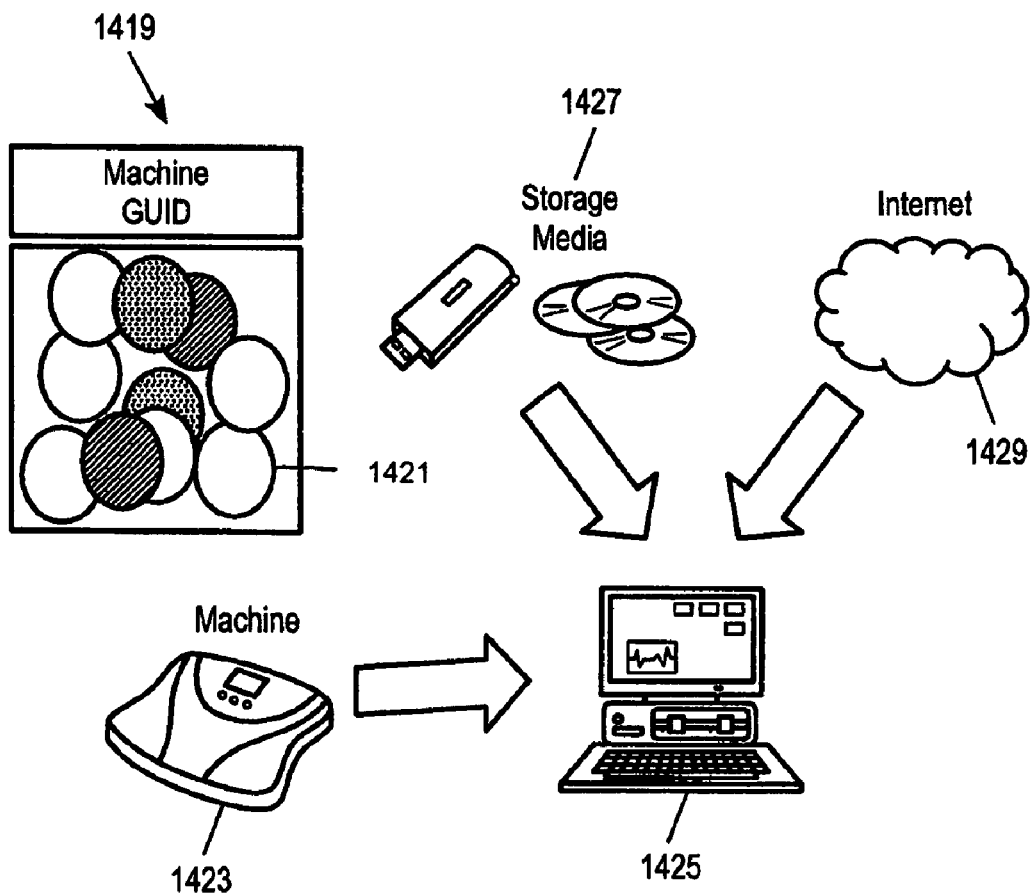
FIGS. 7A-7H show various aspects of dynamic family taxonomy and dictionaries.

The machine dictionary 1419 may be an electronic representation of the taxonomic model of a machine. A diagrammatic example is shown in FIG. 7A. Each sphere 1421 in the dictionary may be an atomic representation of a taxonomic family. FIG. 7A shows three possible methods for a computer platform or other consuming machine to be trained for a new machine model. The machine 1423 may contain the dictionary and transfer it another machine 1425 hosting it. If the machine is unable to store and transfer the dictionary, a CD or other storage media 1427 type may be used to describe the information model. The definition may also come from an internet website 1429 maintained by the manufacturer of the machine. The machine dictionary or DDS may contain what is called a Globally Unique Identifier (GUID) used to associate a dictionary to a machine when it is provided from a source other than the device.

The data dictionary provided may be flexible and support multiple languages via the use of a linking mechanism. The way primitive information is carried in communications may be defined before a discussion of a linking mechanism. Primitive data may be variables transferred in communications and are defined by an agreed upon encoded form. The MOIB framework may provide a set of primitive electronic types used to encode and carry information in electronic form Table I defines some of these encoding types and how they are identified in the dictionary.

TABLE I

| Identifier | TYPE-SPECIFIED |
| --- | --- |
| 0x01H | Uint8 |
| 0x02H | Uint16 |
| 0x03H | Uint32 |
| 0x04H | Uint64 |
| 0x05H | ansichar (String) |
| ... | |

Figure 7B:
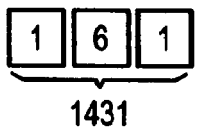
Figure 7C:
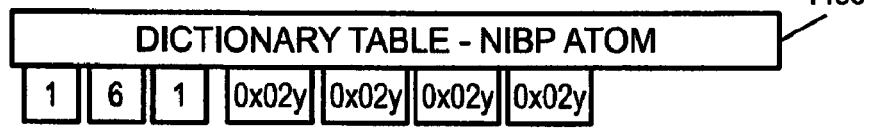

In Table 1, the identifier on the left may be a value or number in the dictionary used to identify a piece of information. For example, if a systolic value is defined in the dictionary it may be carried as a 16 bit integer (numeric value). Likewise the diastolic, heart rate, and MAP values may also be carried as a 16 bit values. Using the taxonomy defined earlier, recall the ID for an aggregated blood pressure reading may be the combination 1431 shown in FIG. 7B. An abbreviated dictionary table 1433 is shown in FIG. 7C.

This reference may exist in the dictionary as an atomic reference and may be followed by the encoding IDs of the members it carries. In the dictionary the set {1,6,1} 1435 may be followed by 0x02y, 0x02y, 0x02y, 0x02y 1437. This denotes a map of the structure of the encoded data needed for a machine receiving the atom represented by the set {1,6,1}. The data values within this structure may include a sequence of 16 bit numeric values. When an ID {1,6,1} is received the values may be extracted. In plain terms the dictionary table may describe how to extract information received.

Figure 7D:
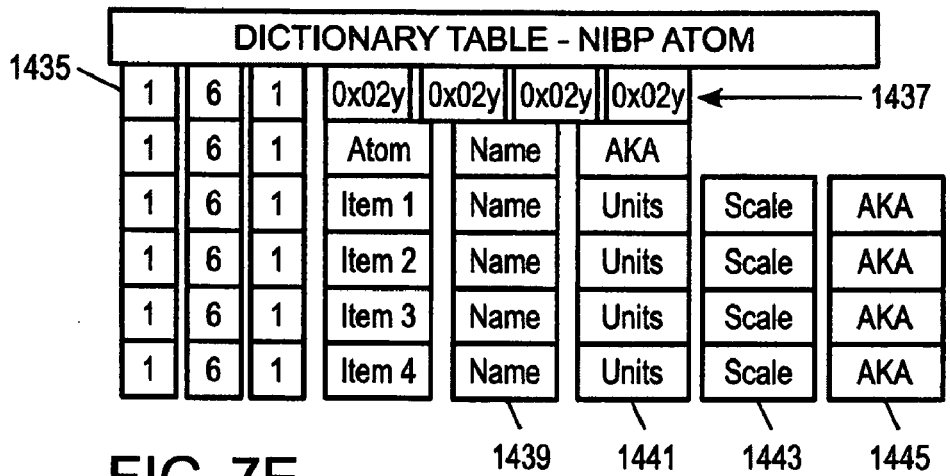

Once extracted the data can be further processed for display by using other dictionary attributes. FIG. 7D illustrates default display text 1439, units of measure 1441, scaling 1443, and AKA 1445 for the atom and each individual member (Items 1-n) in the context of a dictionary entry for an NIBP result with four numeric values. The items in the dictionary may represent the Systolic, Diastolic, Heart Rate, and MAP values. Notice that the units may be defined individually for each item and not at the atomic level. However, if this atom contained a set of item values with the same unit the data dictionary structure could carry units and scale for all items in the atomic family. Differentiating units may be used so each member item carries its own definition. The data dictionary may contain information for the atom as a whole as well as information for each item in the atomic family.

Figure 7E:
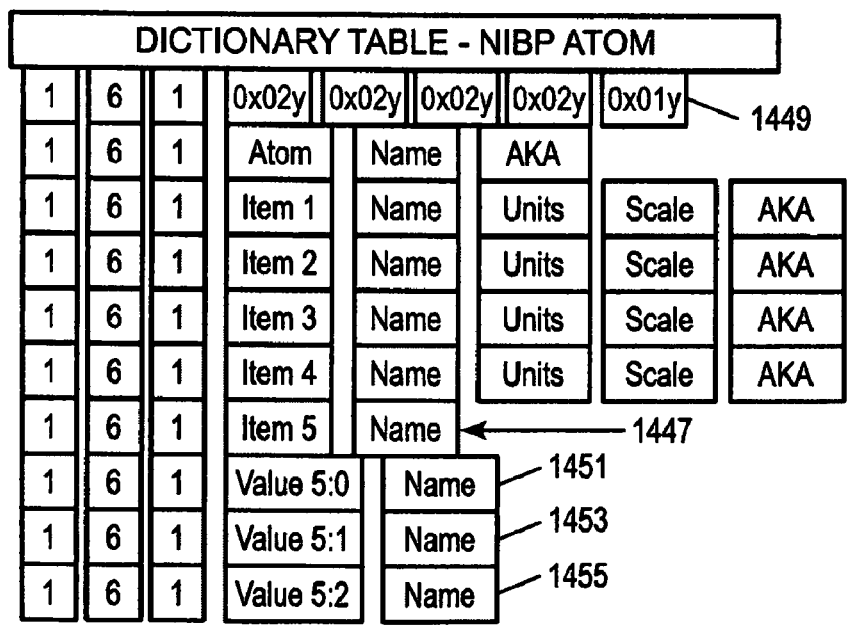

The data dictionary may also support enumerated string types. For example, adding a "reading quality" item to the NIBP entry, may define three states (Green, Yellow, and Red, for example). The three levels may be an indication of quality determined by factors like signal strength at the sensor. This can be defined in the machine dictionary. The item may be added to the original base software component identifiers. An 8 bit integer may be used for representing the value (see, for example, Item 5 1447 in FIG. 7E). FIG. 7E shows a dictionary entry for an NIBP atom with an item for reading quality. The encoded value for item 5 may be added to the map with a 0x01y value 1449. This may be followed by the addition of an actual line item with name and the enumerated string members represented by Item 5:0 1451, item 5:1 1553, and item 5:2 1455.

The value carried in the "reading quality" item may be a number from 0-2. The data dictionary may provide the human readable value for the numeric representation. In this way a human readable value can be displayed. If the last of the five values carried by the NIBP atom is the value 2, the human readable representation may be taken from the dictionary at the value for Item 5:2 1455. In this case it may be "Red". This value can be displayed to the user signifying the confidence level of the reading as determined by the hardware capturing the reading, for example.

The foregoing description covers the basic software component providing the ability to extract machine data and display it using the default language provided in the "Name" attribute. The software component is not limited to this. The software component may be capable of being localized for any language via a linked list mechanism. The linking map or table may be used to correlate the "names" in the dictionary to any language. Looking at the dictionary there may be human readable "name" entries for each item in the dictionary. The Item reference may be used to link to string maps for any language.

Figure 7F:
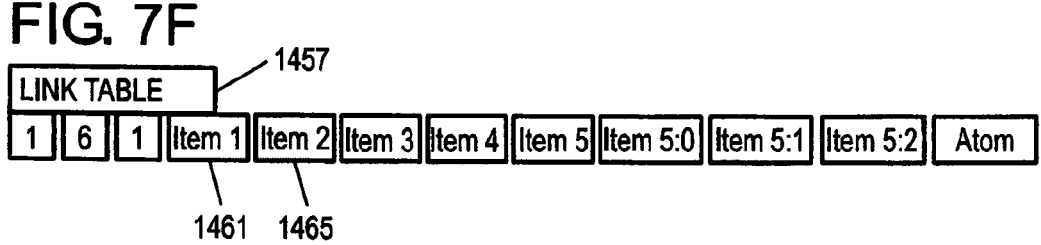
Figure 7G:
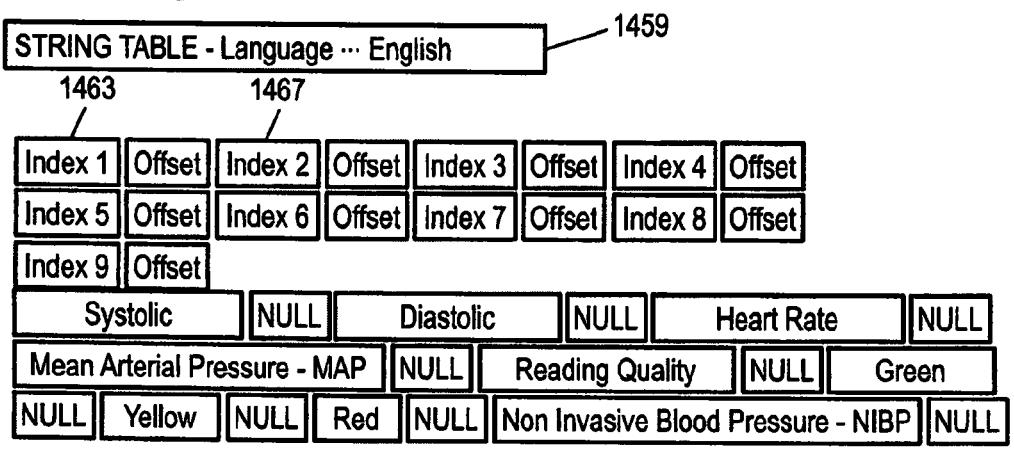

FIG. 7F represents a link table 1457. The data dictionary may rely on the link table of FIG. 7F to define the location of localized strings in any string table. The string table 1459 may be constructed as shown in FIG. 7G. The link table in FIG. 7F may be ordered and related to indexed items in the string table of FIG. 7G. For example, item 1 1461 in the link table of FIG. 7F may correlate to Index1 1463 of FIG. 7G, Item 2 1465 to Index2 1467, etc. The index may contain the offset into the attached string table for the localized string.

The string table may be defined separately and then linked for a specific reason. One of the challenges self described technology faces is duplication of string display text in the machine. The device user interface, e.g. a screen, on a machine may require its own string representation for all of the languages it supports. The DMOIB framework may also require localized strings in order for the device to self describe itself to applications in any language. The string table of FIG. 7G may be designed as accessible to both the embedded device and the DMOIB framework. The string table can be transferred by the device during the self description phase. This may eliminate duplication of string table definition in the device. It may also provide a consistent string/display definition as defined by the machine. The device defined strings passed during self description may be the same employed by the device user interface, thus saving space, providing consistency, and a higher likelihood the device employs self description due to the strings being independently available.

Figure 7H:
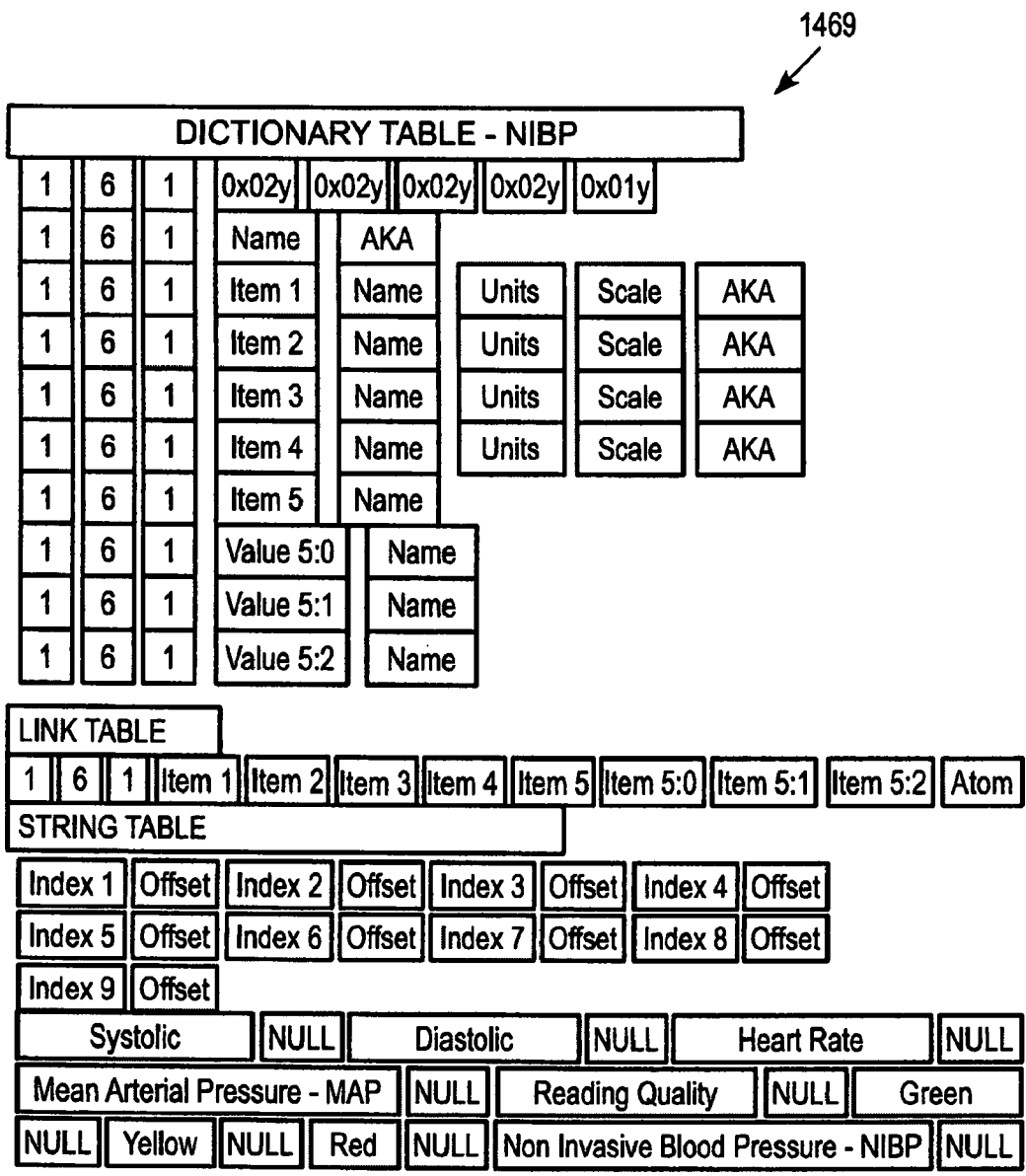

The full data dictionary 1469 for the NIBP atomic family is shown in FIG. 7H. The full dictionary for the NIBP atom may include the main dictionary, the link table, and one or more language string tables.

The present invention preferably includes a version of the DMOIB framework that is preferably compatible with non-dynamic MOIB systems. While there are many possible advantages, the DMOIB framework may create a number of important advantages that can be summarized as follows. DMOIB may allow for an entirely dynamic system using a discovery/negotiation process for determining full features of a device as well as generating a dynamic interface to handle data from devices.

DMOIB may support systems that are required to interpret and display data from devices following standards from MOIB. For example, in situations in which a software system does not have any prior knowledge of a device, DMOIB may allow the system to understand the format of MOIB data structures without knowing the specifics of anyone device.

DMOIB may create a stronger compatibility for systems using MOIB objects. DMOIB may support backwards compatibility, and may update data definitions at run time. Therefore, a system may recognize newer versions of MOIB objects that were previously unknown to the system, providing a sense of forward compatibility.

DMOIB may also reduce code maintenance of projects, because only a single family may be needed to handle evolving and adapting data definitions. In other embodiments of MOIB, separate classes were defined for each atom of data used by a device. Common interfaces to determine classification identifiers (Class IDs) and version information were shared between these classes, but individual accessors were used for each data member of each class. This implementation may lead to large class definitions and repetitious code in classes with similar data members. DMOIB may reduce repetitious code by providing a single interface to access data members of an object, and all data members of similar types use the same methods for access. Also, a DMOIB base class is a static code set that may not need to be updated when data definitions change. Preferably, the only element that requires updating is the definition table (data dictionary used by the device).

Serialization of Messages Using Communication Protocol Taxonomy

Serialization to XML may be advantageous because XML has industry wide accepted tools for transforming the data into other formats.

Figure 8B:
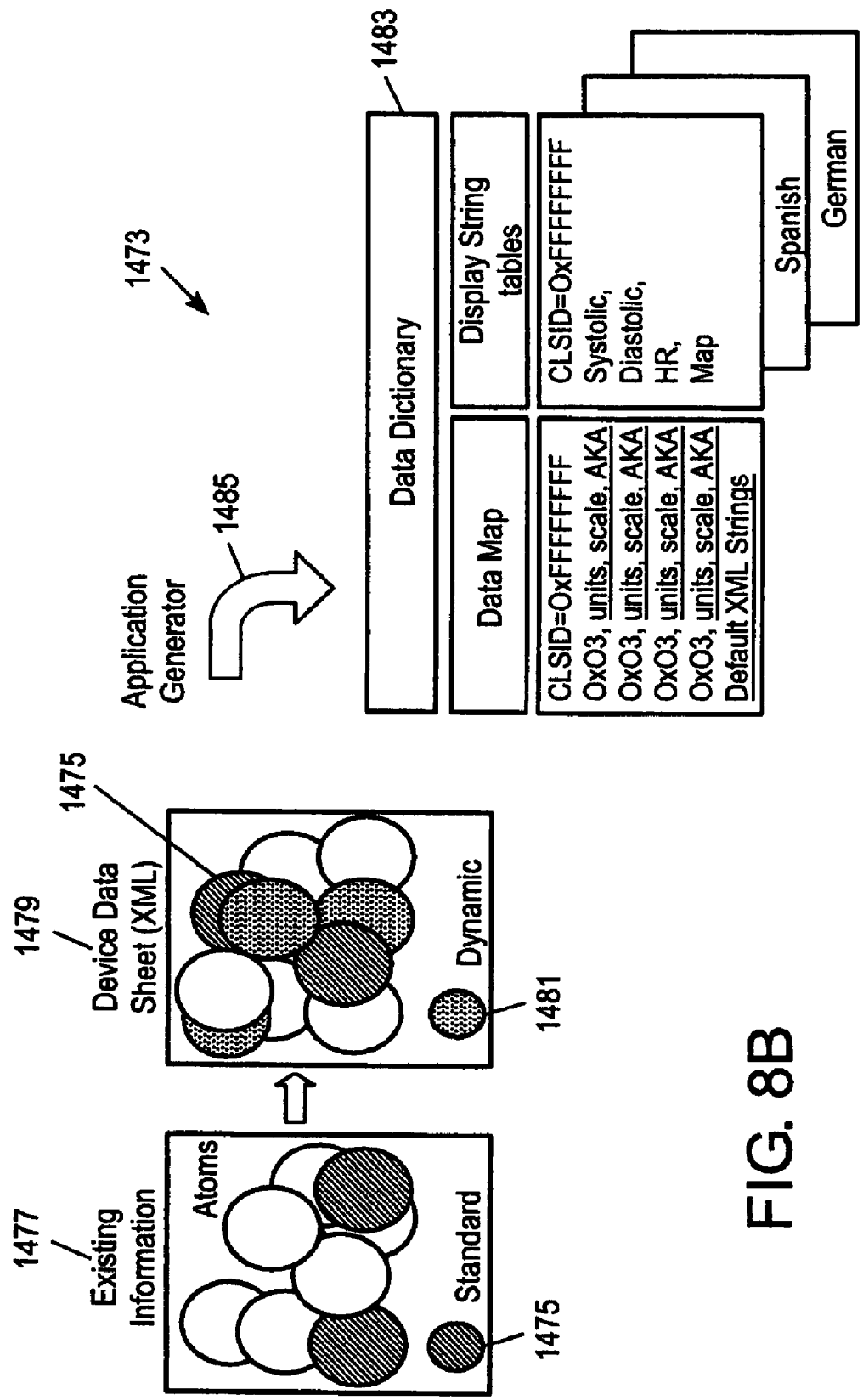
Figure 8D:
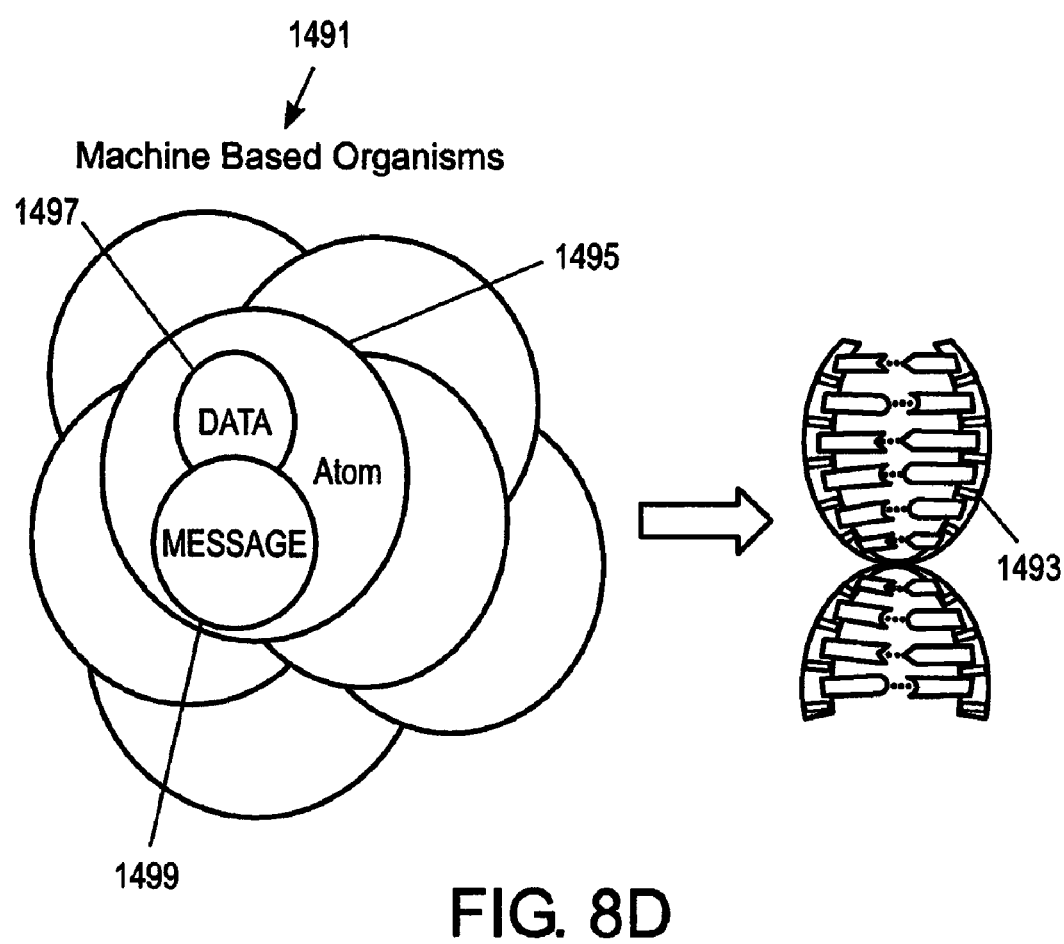
Figure 8E:
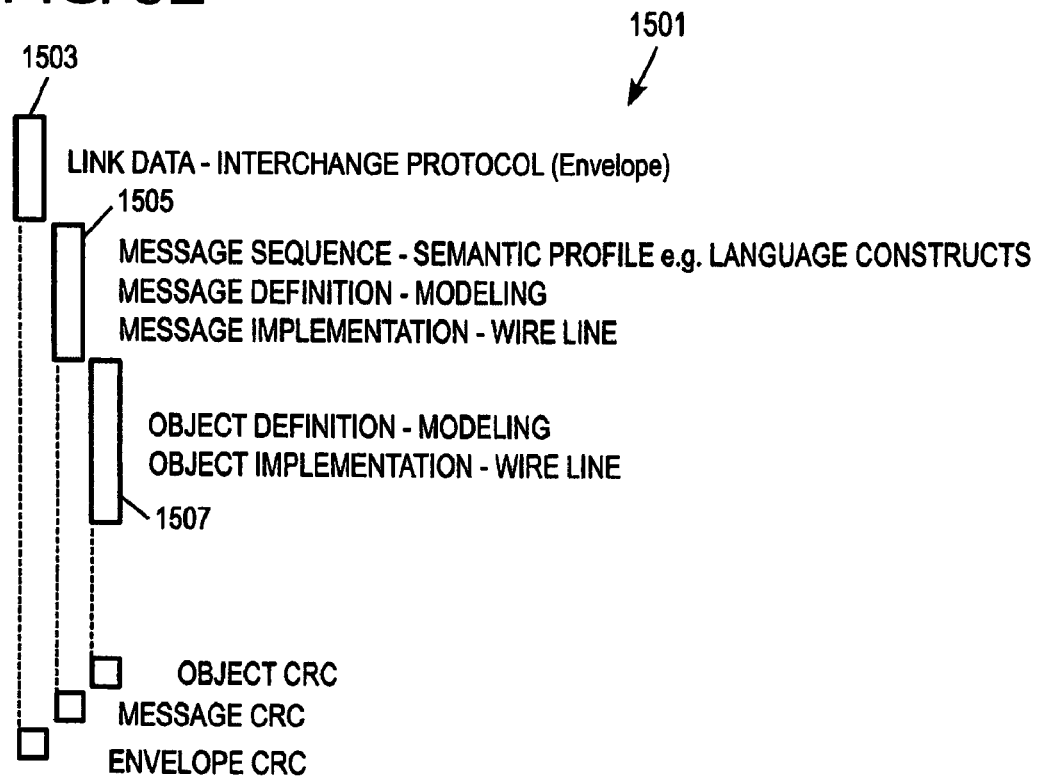
Figure 8F:
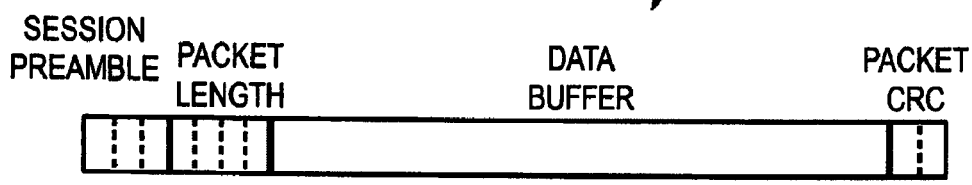

FIG. 8E represents the base protocol structure 1501 as it exists in wire line implementation (byte streams of information). Each was previously defined in relation to the models. To recap, the link data 1503 may be within the envelope carrying payload. The message 1505 may be the predicate or verb and the object 1507 may be the subject. Combined message and object may represent the information modeled after language using the MOMP and MOIB/DMOIB framework FIG. 8F illustrates an electronic form of the communications transport 1509 and is a form all communication protocol-based dialogue takes when communicated via wire line transport.

A wire line specification may be an envelope protocol used to carry conversation. The communication protocol of the present invention may use a simple preamble envelope CTL'W', CTL'A', CTL'L' with a size and a 16 bit CRC for data payload integrity.

Figure 8G:
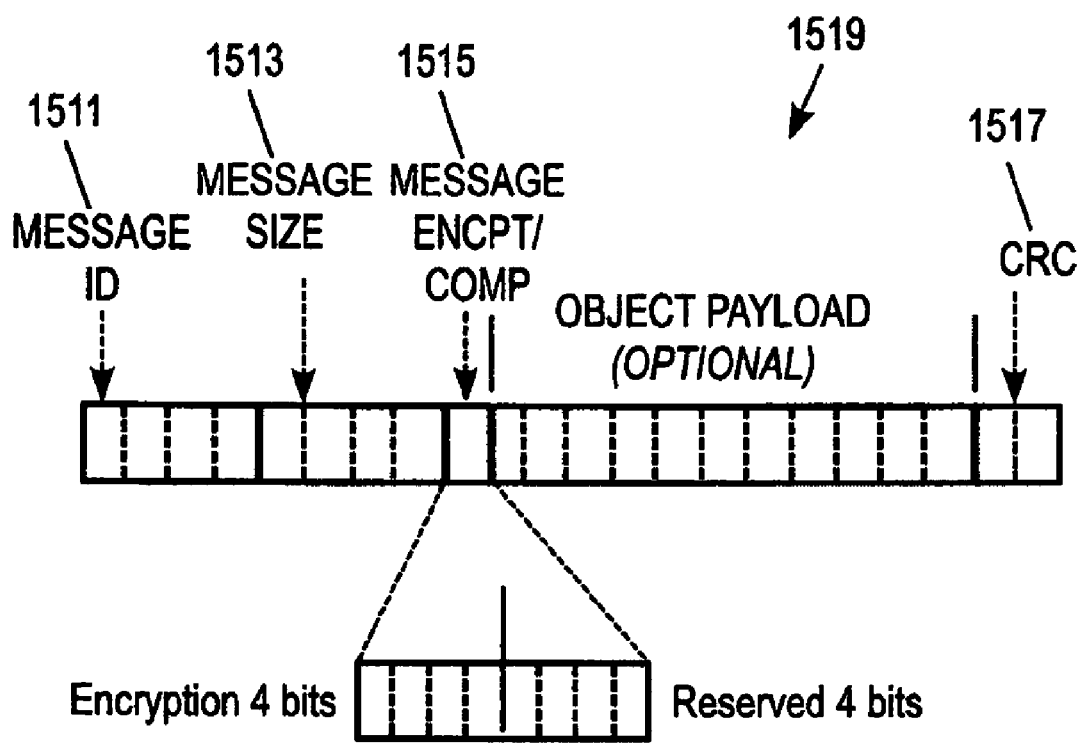

With the information may be a wire line specification for the message. The Family, Genus, and Species methodology employed by the communication protocol may use a genus parameter for the definition of message type along in a specified data structure such as a single 32 bit number allocated to a physiologic family. As shown in FIG. 8G, the wire line 1519 may require at a minimum: (1) Message Op-code 1511: identifying the message context; (2) Message Size 1513: the amount of data potentially found in the message; and (3) Message encryption bit field 1515: a bit field identifier for identification of multiple forms of encryption (4) Message Integrity 1517: a 16 CRC or similar method of message integrity insurance.

Figure 8I:
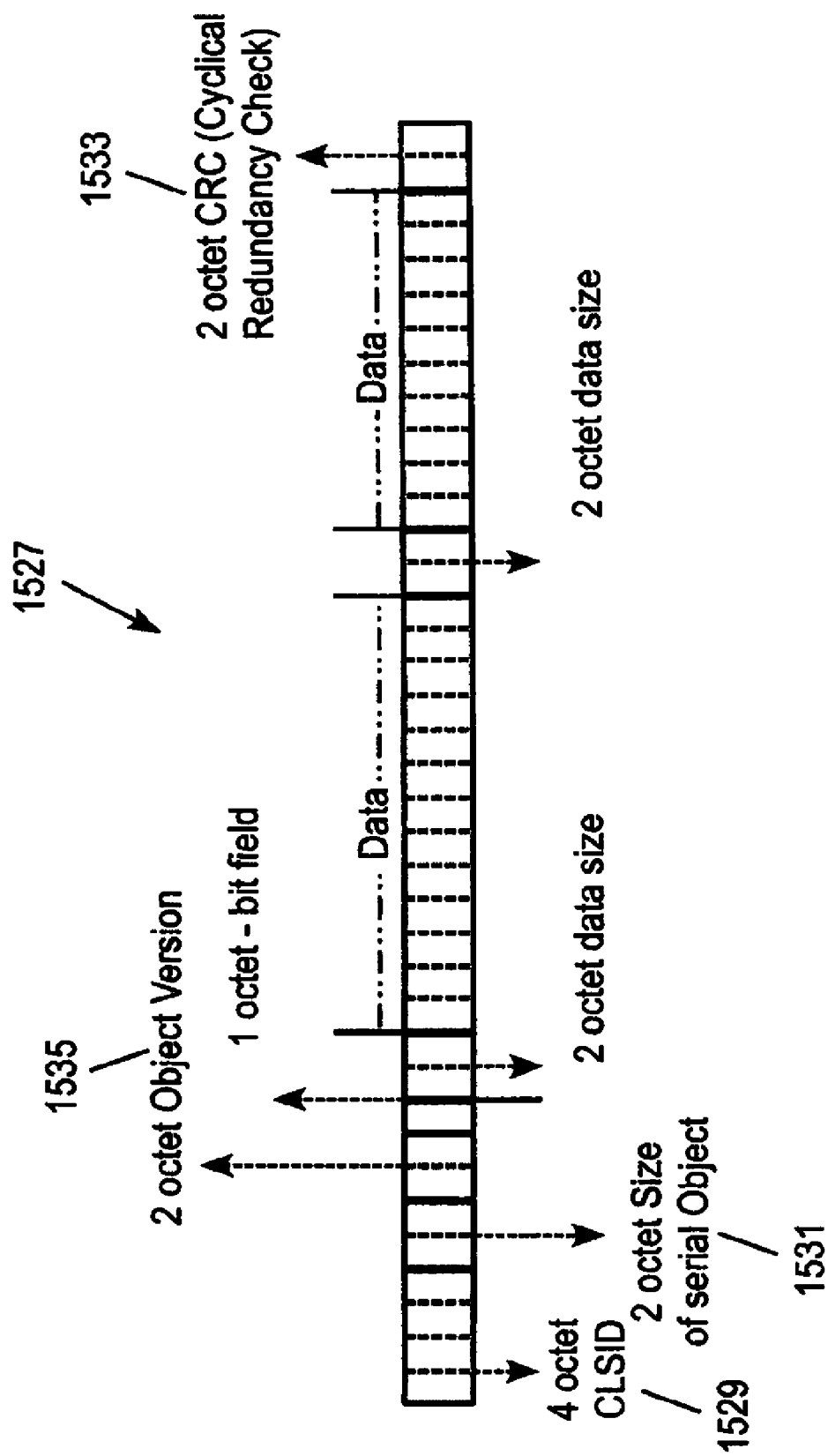

With the object may be a wire line specification. The Family, Genus, and Species mechanism employed by the communication protocol may have genus provisions for the definition of the data with in the context of a single 32 bit number allocated to a physiologic family as shown in FIG. 8I. The wire line 1527 may require at a minimum: (1) Data Op-code 1529: identifying the data carried; (1) Data Size 1531: the amount of payload found in the data container; (3) Data Integrity 1533: a 16 CRC for data integrity assurance; (4) Version 1535: and (5) Compression type.

The data definitions may be formatted, and all definitions may be understood by DMOIB objects. The ability to create and process the data definitions may be provided entirely as part of the DMOIB implementation.

Data definitions may all be stored generically as byte-arrays on a system using the data definitions. For example, explicit structures may be defined or used to store the definitions, since disparate systems may organize or pad structure members differently. All values may be tightly packed, in Big-Endian fashion. The following describes major elements in a definition.

A data definition may include a single definition header (Header) section, with specific information applying to an object as a whole. The Header may include the number of Species available in the definition, the Family, Genus, base Species, and the Version. In some cases, multiple Species may be identified for a single definition. If multiple Species are available, all Species applying to that definition may be listed in order, after the Genus and preceding the Version. Following the Version may be the Definition Size, which is the total size, in bytes, of the definition itself. Since all definitions may be variable length and there may be no specific terminating sequence, this value may be available at the beginning of the definition so the end can be calculated while parsing it. Following the Definition Size may be the XML Base size. This is the size, in bytes, of the minimum string length that the serialized form of this definition would occupy. The Definition Size may also be used as a flag to represent the presence of the optional XML text information at the end of the definition. If this value is 0, then it can imply that no XML text is available. Any other value can be interpreted as the minimum byte size for XML serialization. The next element may be the Member Count, which is the total number of items in the atomic family that are present in the definition. The Member Count may be used in the parsing process when determining what items are available for the currently instantiated object's version. Since each item in a DMOIB object may or may not be available in the current version of the object, this value identifies the maximum possible number of members available.

After the Header, each item of the atomic family may be described in order of availability, proceeding to the end of the definition. The first items of the family may be the min and max versions for that item. Each item may have an associated minimum and maximum version value, which expresses the version span in which this item is available. For example, if an item has a minimum version of 100 and a maximum version of 150, then a DMOIB object of version 200 instantiated from this definition may omit the item from its internal data structure. The versions allow developers to add and remove items from an existing definition without breaking compatibility with previous versions. The versions may also provide a full history set for each definition, as all items that were ever available as members of the family are fully described, along with the versions in which they were available.

In a preferred embodiment, only one min and one max version can be specified for a single item, meaning the item can only be given a single version span for availability. If an item has been removed in a prior version of an object, it cannot be reinstated in a later version. This also means that developers must check each data item of a family for availability before attempting to access it. Since it is possible that items from a previous version of a definition are no longer available, any algorithms that rely on the data provided by an object's members must take appropriate measures to safeguard against processing errors from attempting to access a non-existent member.

Following the min and max versions may be the type information for the member. The type information preferably aligns with one of the base types defined for MOIB. The type information is preferably a single byte (8-bit) value that encodes all type information for the member in a binary form and allows the type to be determined at run-time.

Figure 8J:
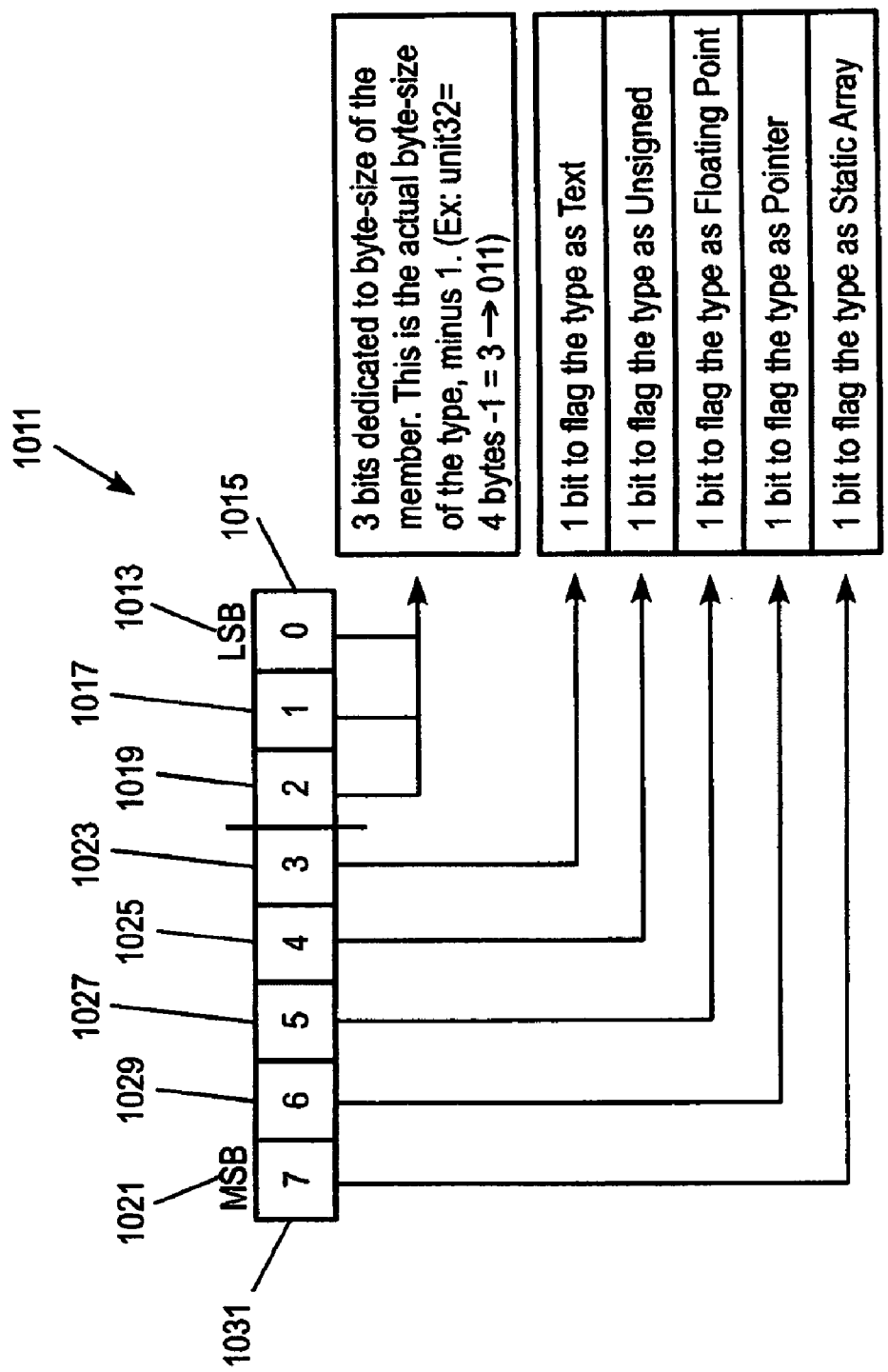
Figure 8K:
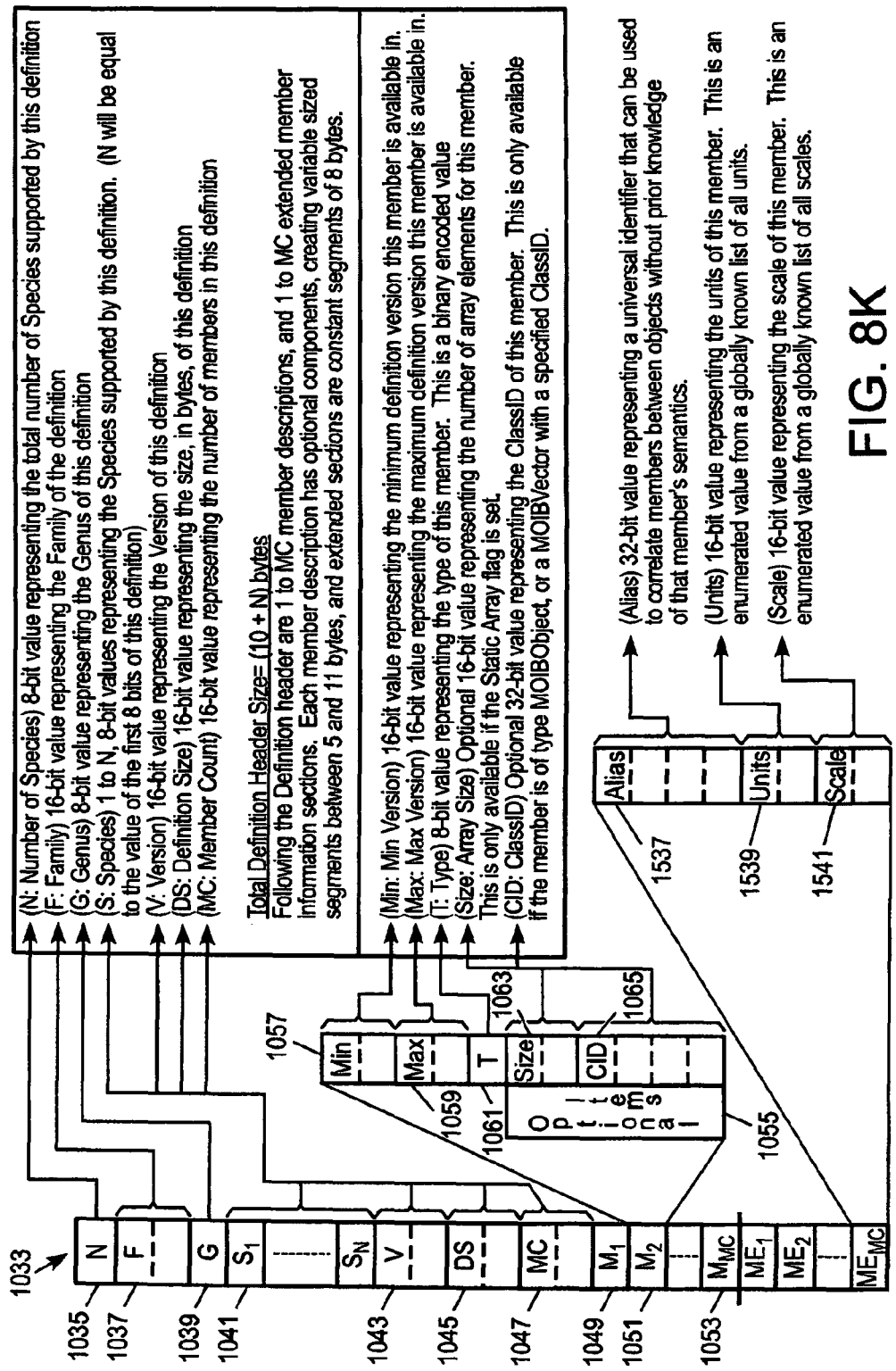

FIG. 8K shows an explicit layout 1033 for a data dictionary definition. Each box in the column along the left side represents a single byte (8-bit) value or data segment, where boxes with dashed lines represent multi-byte values or data segments. This internal structure is preferably not directly accessed by a developer. All interaction with a definition should be made through a DMOIB implementation class. In the following description, N-bit values refer to data segments in the structure of the data dictionary.

A total definition header 1033 may include several variable sized segments. A top box N (Number of Species) 1035 may be an 8-bit value representing a total number of species supported by the data definition. A next box F (Family) 1037 may be a 16-bit value representing the family of the data definition. A next box G (Genus) 1039 may be an 8-bit value representing the genus of the data definition. The next series of boxes $S_1$-$S_N$ (Species) 1041 may be 1 through N 8-bit values representing the species supported by the data definition. N may be equal to the value of the first 8 bits of the data definition. The next box V (Version) 1043 may be a 16-bit value representing the version of the data definition. The next box DS (Definition Size) 1045 may be a 16 bit value representing the size, in bytes, of the data definition. The next box MC (Member Count) 1047 may be a 16-bit value representing the number of member items in the data definition. Preferably, the total definition header size is equal to (10+N) bytes.

Following the initial information may be blocks representing each member from $M_1$ 1049, $M_2$ 1051, . . . , $M_{MC}$ 1053. Each member item contains information that may be optional 1055. For example, $M_2$ may contain boxes for Min (Min Version) 1057, Max (Max Version) 1059, and T (Type) 1061. Min 1057 may be a 16-bit value representing the minimum definition version in which member $M_2$ 1051 is available. Max 1059 may be a 16-bit value representing the maximum definition version in which member $M_2$ 1051 is available. T 1061 may be an 8-bit value representing the type of member $M_2$ 1051.

FIG. 8J shows a detailed view 1011 of the data structure sequence represented by T 1061 in FIG. 8K. For selected data types, the three least significant bits (LSB) 1013 of the data structure may be used to represent the byte-size of that item, i.e. positions zero 1015, one 1017 and two 1019 in FIG. 8J. For normal data types, the five most significant bits (MSB) 1021 of the data structure may be used to flag the type, i.e. text at position four 1023, unsigned at position five 1025, floating point at position six 1027, pointer at position seven 1029, and static array at position eight 1031. For example, the byte-size of an unsigned long integer is 4 bytes (32-bits), so the 3-bit segment in the data structure would contain the value 4. However, the maximum value that can be represented with 3 bits is an integer value of 7, and some data types have a byte-size of 8. To accommodate this, the 3 bits of the data structure may actually represent the byte-size of the item, minus 1.

Therefore:
  0: 1-byte types resolve to a value of 1−1=0 (char, Boolean, etc.).
  1: 2-byte types resolve to a value of 2−1=1 (short).
  3: 4-byte types resolve to a value of 4−1=3 (long, float).
  7: 8-byte types resolve to a value of 8−1=7 (double).

The unused values from this list can then be assigned to special data types, such as the DMOIB object type. The following values are reserved for special data types:
  2: DMOIB time structure
  4: RESERVED
  5: RESERVED
  6: DMOIB sub-objects and DMOIB vectors Certain optional data segments may be used to define static/standard elements (MOIB), while other optional data segments are used to define dynamic elements (DMOIB). The first of these optional data segments may be a Size specifier, which is only available for standard member items that have the Static Array flag (bit 7) enabled. The Size specifier value may represent the size (in number of bit values) for the related Static Array type. The other optional data segment is a ClassID specifier, which is only available for members items that have a byte-size (bits 0-3) identifying it as a DMOIB object type or DMOIB vector. The ClassID may correlate to a definition used to create the sub-object, or elements of the vector. These optional parameters are not mutually exclusive, and a member may have one or the other, or both of these values present. However, if both are present, the Size specifier preferably always precedes the ClassID.

Following the format of member data segments may be a section of extended information. This section may follow a structure similar to the member item format, with a list of 8-byte segments, one after the next, each associated with the member corresponding to the segment's position. Each segment may be divided into three fields of information as follows:

Alias or AKA (32-bits) 1537: An alias or AKA may be a value assigned to a member that can be used to associate this member with members from other objects without prior knowledge. This may allow members to be substituted in algorithms or displays based on alias, as long as the alias matches the expected alias that is applied to that algorithm or display element.

Units (16-bits) 1539: The Units field may be a numerical representation of the units associated with a member. This numerical value may align with a globally known enumeration that details all known units for all supported data sets.

Scale (16-bits) 1541: The Scale field may be a numerical representation of the scale associated with a member. This numerical value may align with a globally known enumeration that details all known scales for all supported data sets.

The global values used to define Alias 1537, Units 1539, and Scale 1541 information may be available as constants in a project header file, which may be generated by the AppGen tool during the DDS processing phase.

In addition to the data structure stored within a definition, an optional XML text section may appear at the end. The optional XML text section may include all XML text required for serializing to, or deserializing from an XML formatted text stream (the XML names for all members, enumerations, enumerators, Species, and Classname of the definition).

The XML text section may follow similar constructs as those present in a string table and link table binary formats. The XML text section may contain a header segment that provides lookup information for all elements of the definition, and a string block which is a contiguous section of null-terminated XML strings. The lookup table in the header provides translation information to resolves elements of the definition to offsets into the string block.

The XML text section may be an optional portion of the binary definition, and its presence is deterministic at run-time through the XML base size value from the definition header. The XML text section may be optional because of the possible constraints of embedded systems. Basic MOIB already provides developers the ability to enable or disable XML serialization and deserialization at their discretion, based on the requirements and constraints of the project. The XML text section follows that same concept, and leaves the option of including XML text in definitions up to the end developer.

To ensure cross-platform compatibility with the data definitions, all values in the definitions may be stored in Big-Endian form. The storage preferably remains consistent with the Endianess of serialized DMOIB objects. The storage also preferably allows a definition to be directly transmitted from one system to another without worrying about reformatting before sending. When a value is retrieved from a definition, the DMOIB software takes the appropriate measures to convert the value from Big-Endian form to the local system's form.

Figure 8L:
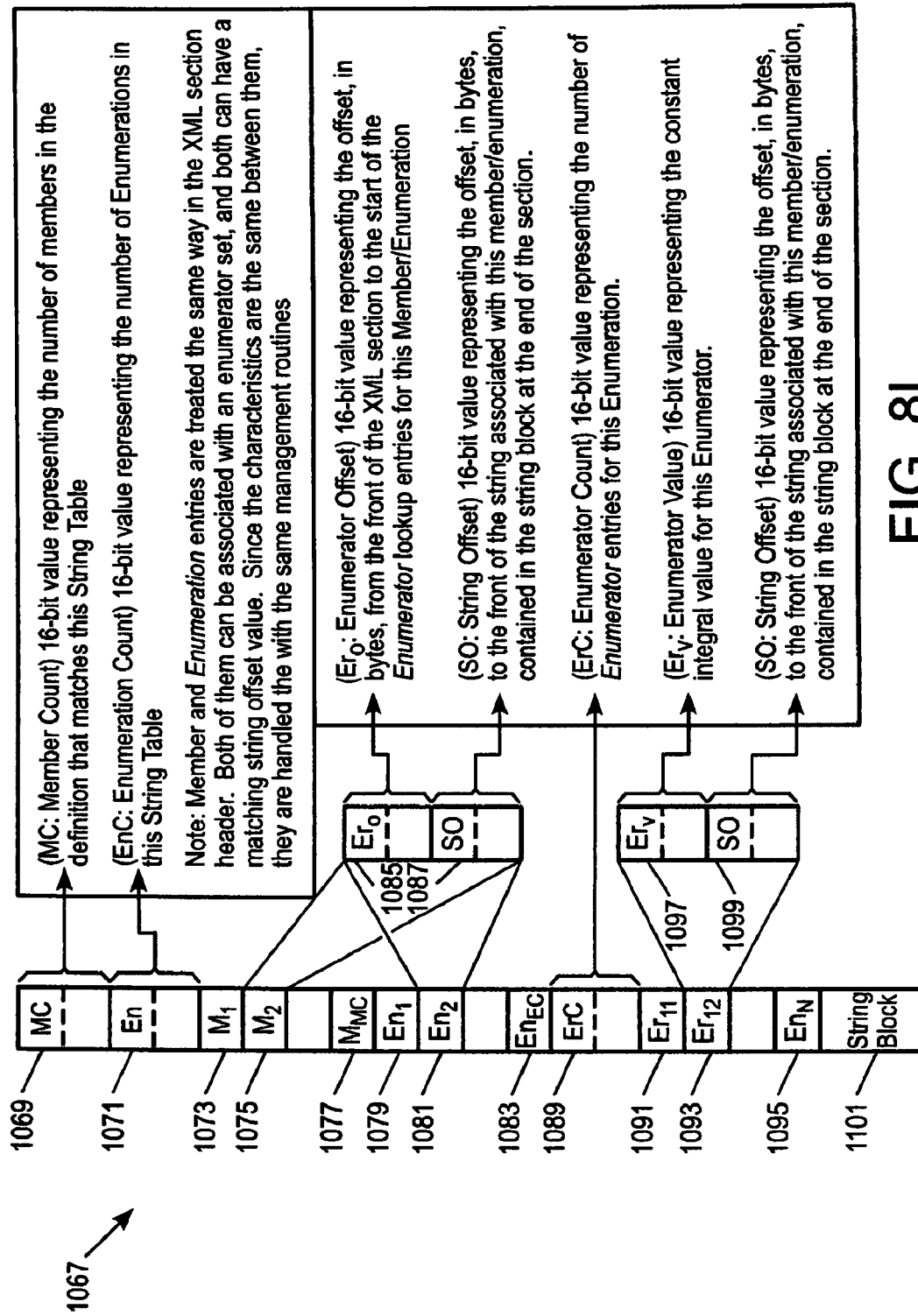

FIG. 8L shows an optional XML section 1067. Immediately following the normal data definition structure 1033, shown in FIG. 8K, may be an optional XML section 1067. If the XML section 1067 exists, it is part of the contiguous memory block storing the data dictionary 1033. A top box MC (Member Count) 1069 may be a 16-bit value representing the number of member items in the data definition that matches the string table. The next box En (Enumeration Count) 1071 may be a 16-bit value representing the number of enumerations in the string table. Member and enumeration entries are treated the same way in the XML header section. Both of these entries can be associated with an enumerator set, and both can have a matching string offset value. Since the characteristics are the same between them, they are handled with the same management routines.

Following the initial information on MC 1069 and En 1071, are members $M_1$ 1073, $M_2$ 1075, ..., $M_{MC}$ 1077, and enumeration $En_1$ 1079, $En_2$ 1081, ..., $En_{EC}$ 1083. Each member and/or enumeration may have $Er_O$ (Enumerator Offset) 1085 and SO (String Offset) 1087. $Er_O$ 1085 may be a 16-bit value representing the offset, in bytes, from the front of the XML section to the start of the enumerator lookup entries for this member/enumeration. SO may be a 16-bit value representing the offset, in bytes, to the front of the string associated with this member/enumeration contained in the string block at the end of the section.

Following the member and enumeration section may be an ErC (Enumeration Count) 1089. The ErC 1089 may be a 16-bit value representing the number of enumerator entries for the enumeration.

Following the ErC 1089 may be enumerators $Er_1$ 1091, $Er_2$ 1093, ..., $Er_N$ 1095. Each enumerator may contain an $Er_V$ (Enumerator Value) 1097 and an SO (String Offset) 1099. The $Er_V$ 1097 may be a 16-bit value representing the constant integral value of the enumerator. The SO 1099 may be a 16-bit value representing the offset, in bytes, to the front of the string associated with the enumerator contained in the string block at the end of the section. A string block 1101 follows the enumerators.

Processing of Serialized Communication Protocol Messages by Communication Protocol Architectural Structures Referring back to the dictionary in FIG. 7H may enable description of the process that DMOIB uses to extract and provide data for display or processing. Assume the compute platform has received the dictionary in FIG. 7H. When the compute platform receives a message containing the ID {1,6,1}, the compute platform may use the dictionary to prepare/process the data in the following two steps.

Step 1 may include extracting the data. The dictionary table may be used to recognize what to extract by specifying the data segments that encompass the structure of any wire line message received by the computer platform. As defined earlier, primitives or data segments may be electronic representations of variables carried by an atom in MOIB. A value of 0x02y may be the ID for a 16 bit numeric. DMOIB may use this information to extract 16 bits of information from a buffer of data identified as {1,6,1}. DMOIB may then extract the four other primitives or data segments from the wire line message. DMOIB may then have five separated variables representing member items of the NIBP atomic family.

Step 2 may include the display of the data. DMOIB may provide an interface to gather information from the dictionary to properly display information based on how the dictionary defines the information. Application software may employ DMOIB software components to access the base dictionary and linked string tables. The link table can be used to gather the localized (language) representation of the member from the proper string table.

Applications may display the DMOIB information based upon attributes for each value found in the dictionary may then be applied to each value.

For systolic information 1545 the scale might be 0.01. The scale value may be multiplied with the encoded data to produce properly formatted data. For example, the value in the systolic item may be encoded in a 16 bit numeric as 12,000, for example, with no precision (decimal). When multiplied by the scale factor 0.01, a value of 120.00 may result. Due to floating point encoding sizes and arithmetic differences between processors, precision data may normally be sent as integer values requiring a scale conversion.

For diastolic information 1547 the value might be 8,000. When multiplied by the scale factor of 0.01, a value of 80.00 may result. Heart rate information 1549 may or may not have a scale. For MAP information 1551 the value may be 9,000. When multiplied by the scale factor of 0.01, the resultant value may be 90.00.

The "Reading Quality" 1553 may be displayed by extracting the value of the final 8 bit encoded data. The name of attribute may be displayed followed by the name corresponding to the number encoded in the 8 bits of data. E.g. a value of 0 may mean the quality is good or "green" 1555, a value of 1 may be marginal or "yellow" 1557, and a value of 2 may be poor or "red" 1559. Combining units may provide the final display built from the information in the dictionary.

Figure 9A:
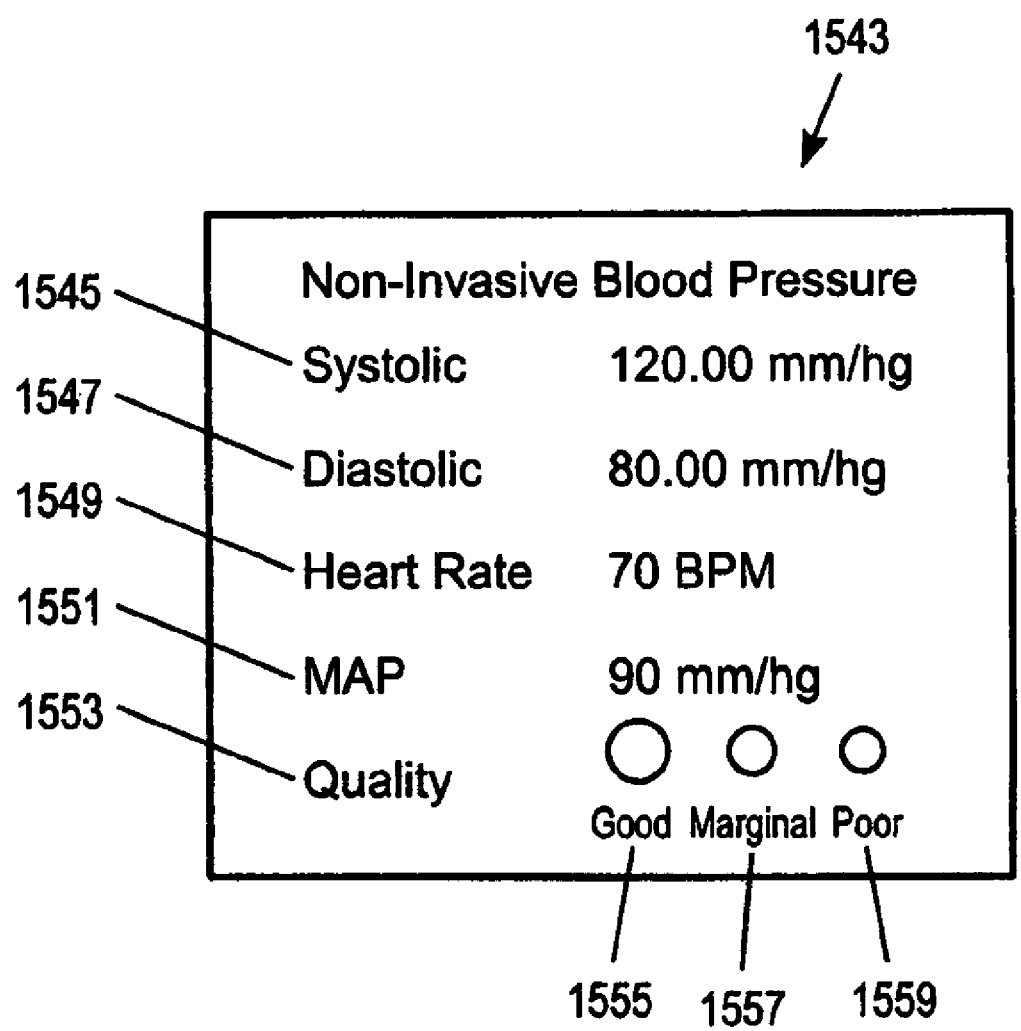

The dictionary may allow the display 1543 shown in FIG. 9A to be built by an application supporting the dictionary relying on the dictionary to produce the interface. The same process can be applied to any newly discovered information allowing for machine perception and information plug and play.

DMOIB is a useful technology for creating intelligent applications that may meet the needs of adapting systems. There may be machines unable to leverage self description due to processing and memory constraints. For these machines, structure analogous to a traditional standards-based structure may be required. Traditional communications systems reserve identification numbers representing well known structures of information passed in communications. They are not expected to change. As an example a standard between network constituents might be the set {1,6,1}, representing an NIBP with four parameters, each encoded in 16 bits in order of systolic, diastolic, heart rate, and MAP. The units may be mm/hg and the scale 0.01. The data structure or framework may be predefined and all machines in the network may be programmed to utilize the agreed-upon standard data structure.

In our exemplary framework taxonomy for blood pressure, the set {1,6,1} represents a numeric ID from the blood pressure family. More precisely it may be a definition of the data structure for a diagnostic Non-Invasive Blood Pressure ("NIBP") reading. Using the dictionary the receiver may have a flexible mechanism for extracting information as defined by the machine dictionary. If the dictionary does not exist the information must instead be standardized and controlled in the traditional sense. For physiology components (hardware sensors) serving one function like temperature or blood pressure capture, the DMOIB approach may not be employable due to performance constraints. In simple devices like these there are provisions supporting traditional reserved numbers in the taxonomy. This is done in each family by reserving numbers at the species level. The range may be used to define fixed structures. Information types in this range may be contractual. If they change there may be rules for how as defined in MOIB.

The following example embodiment of the present invention is a simple text based portion of a data dictionary (a data map) supporting adaptive self described technology for simply extracting data from a binary stream and accessing the display strings and attributes associated with each member item. The string data that follows may be optional string data generated at the time of creation. The string data can be used in place of language based string tables described later.

Sample Data Map

```
<DATAMAP>
65824|0:0x02h|1:0x02h;
---Optional---
65824:"CardioVascularPulseRateDynPleth"
65824|0:"PulseRatePleth",U:"Beats Per Minute",S:"0.01",A:Pulse
65824|2:"Quality"
65824|2-0:"Green"
65824|2-1:"Yellow"
65824|2-2:"Red"
</PHDDATAMAP>
```

Using the data map above a received ClassID may be broken down into its constituent parts for processing. Notice that Pulse Rate with class value 65824 has two preceding type specifiers (0x02h=uint16) because it has extra variables for the reading and quality of the reading. Additionally, the data map may have optional additional primitive strings that can be used if needed.

The data dictionary described earlier may support a string. However, another approach may be to define strings via a link so strings can be shared in a device between the dynamic self description and the display needs of the device. This may eliminate unnecessary repetition of strings used in self description and on the device. An English string map 1585 is shown in FIG. 9G along with a link table used to determine the string for each member.

In the link table the members 1587 are separated by the '|' symbol. For example, "0:0" is the link for the first item. The value following the "0:0" in the link entry "0:0" is zero. This may represent an array location 1589 in the actual string table header that houses the offset into the string table that represents the item's text representation 1591.

A full adaptive solution may require the use of both the data map and the string map as shown below.

Combining Maps:

```
<DATAMAP>
65824|0:0x02h|1:0x02h|2:0x02h;
---Optional---
65824:"CardioVascularPulseRateDynPleth"
65824|0:"PulseRatePleth"
65824|1:"Units"
65824|1-0:"BeatsPerMinute"
65824|2:"Quality"
65824|2-0:"Green"
65824|2-1:"Yellow"
65824|2-2:"Red"
</PHDDATAMAP>
<LNKMAP>
65824|0:0|1:1,1-0:2|2:3,2-0:4,2-1:5,2-2:6|0xFFFF-0:7
</PHDLNKMAP>
<STRMAP language="English">
0:0;
1:25;
2:31;
3:48;
4:56;
5:62;
6:69;
7:73;
Dynamic Pleth Pulse Rate(NULL)
Units(NULL)
```

-continued

Combining Maps:

```
Beats Per Minute(NULL)
Quality(NULL)
Green(NULL)
Yellow(NULL)
Red(NULL)
Dynamic Pleth Pulse Rate Package(NULL)
</PHDSTRMAP>
```

Using the string table it may be easy to find the hooks that allow for XML output or drive intelligent display UI as defined earlier. Using self description may provide the string map and, therefore, a bridge to XML. XML may fall out of the combination of both maps. An example of the pulse rate output from the map in FIG. 9G. can be seen below.

```
<Dynamic Pleth Pulse Rate Package >
   <members>
      <member name="Pulse Rate" value="60" type="unit16"/>
      <member name="Units" value="Beats Per Minute" type="unit16/>
      <member name="Signal Quality" value="Green" Type="unit16/>
   </members>
</ Dynamic Pleth Pulse Rate Package >
```

This added benefit may allow for easier integration of information from the binary network to the informatics network. Once in XML transforms can be used to turn HL7 or any other formats.

DMOIB implementation may be split into two information processors. The first may be a pure discovery model in which the machine defines the information model. This may be the pure dynamic model. In this model, since the machine may communicate the model each time, the communicating application may be nothing more than an interpreter of the machine model. This does not exclude a managing application from cache a machine data dictionary for a specific machine instance using version spanning to keep the data dictionary up to date. In the second manifestation, built on static types, the communicating application may maintain a memory of standard types and may be constantly learning or replacing old version of MOIB definitions with newer updated models.

In cases where DMOIB is not used the MOIB/MOMP specification may still employ intelligent rule based dialogue but not self description from the device. This does not limit changes to standard MOIB types. An MOIB object of lesser version may be unable to receive an MOIB object of greater version. However, an MOIB object of greater version may contain the evolution history of the object, and can adjust in processing based on what the atomic family defines. MOIB is backwards compatible.

Figure 9B:
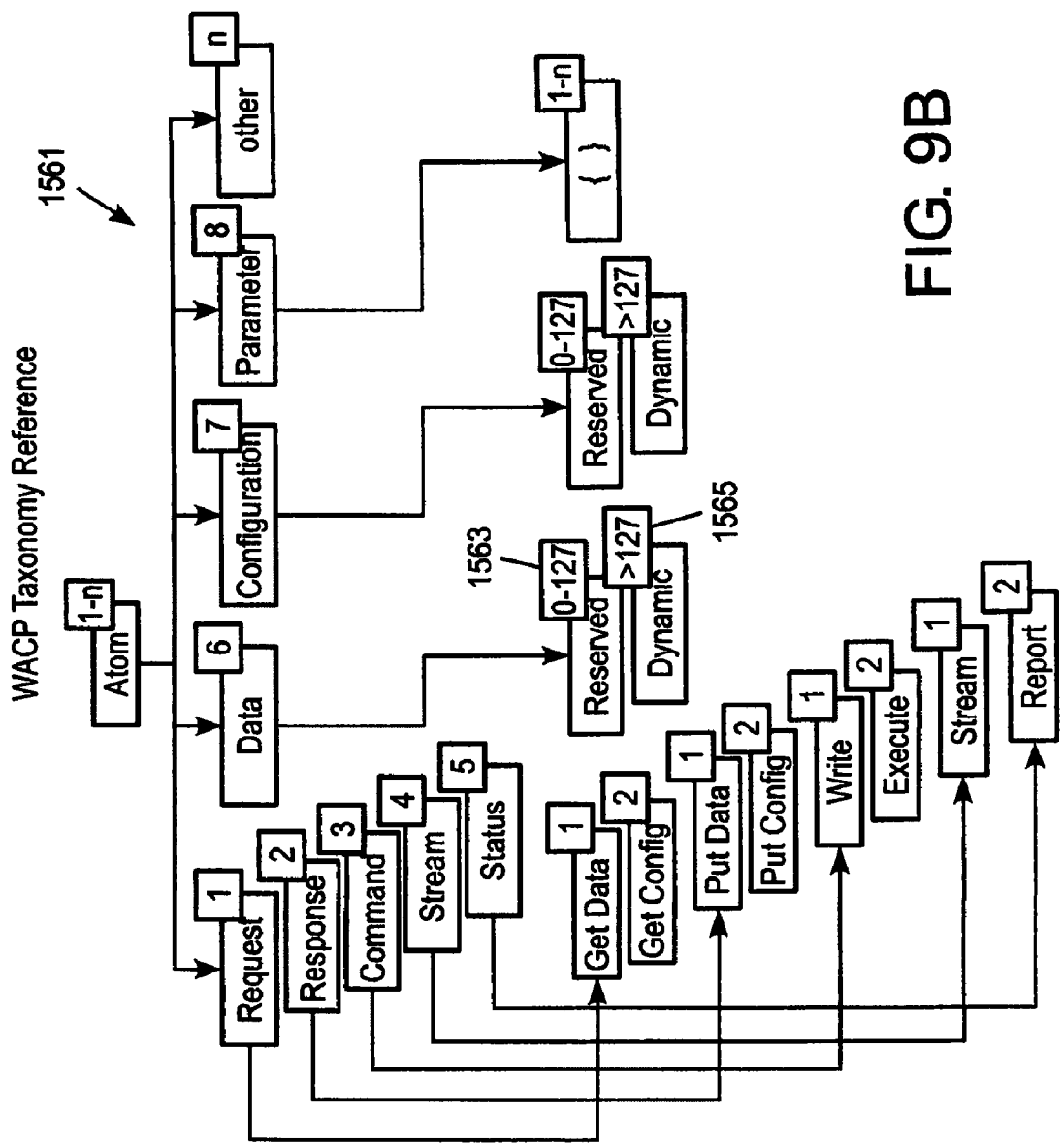

FIG. 9B is the taxonomic framework reference 1561 for the communication protocol expanded to include the reservation of standard types. The data species may be split into two reservation sections. The first 1563 may be standard based information governed by traditional paper contracts for information models. The other half 1565 may be reserved for DMOIB. Machines developing taxonomies intending to deploy self description may use the species values in the set reserved for DMOIB, i.e., greater than 127 or another suitable number. In other embodiments the genus could also be used to differentiate standard data and dynamic data.

In the taxonomy of FIG. 9B, configuration may employ the same model as data. Standardizing on configuration may be difficult at best due to varying hardware platforms and algorithm options used in various machines. Dynamic machine dictionaries may be beneficial in that a single configuration application can configure any communication protocol compliant machine by utilizing the data dictionary.

Standard definitions may be managed in a list of defined information like paper based standards. Modifications may be carefully managed. MOIB may provide a mechanism for working with evolution of standardized information. Individual member items in an atomic family may carry a version-spanning mechanism for recognizing varying versions of those members. In the NIBP example, a version-spanning attribute may be added to the dictionary for each member. This attribute may define each item's history 1567 as shown in FIG. 9C.

If the NIBP atom is defined with the four original attributes and released for use, the NIBP atom may have a version reported as 1.0 for the version attribute of the NIBP atom. All encoded MOIB atoms may carry a version identifier. The version span attribute seen in each item (1-4) may define when the item existed in the atom. For the first release each version span attribute may be "Version 1.0 to Current" or "1.0-Cur". If a new item following the 1.0 release of the item is added and the atomic version span is increased, the version span for the new item may be "Version 2.0 to Current" or "2.0-Cur".

FIG. 9D shows a new entry 1569 in the table. Item 5 has been added and the atomic version increased to 2.0. Item 5 may be introduced in version 2.0 and, therefore, reports a history 1571 as 2.0-Cur. NIBP atoms may use the received information reported version to determine what to process and what to ignore.

In processing standard or dynamic types, DMOIB and static MOIB may first look at the version attribute of a received wire line message at the atomic family level. DMOIB may check the received version against the current/working version for the MOIB atom. The version of the working atom must be equal to or greater than the version of the message received to process the data embedded in the message. If the version of the working atom is not equal to or greater than the version of the message, then the device may be missing important history about the items in the received message and be unable to extract the information properly. If the working MOIB atom is greater than or equal, the device may compare the received version of the atom against the version spans for each item to determine if the item is available. Receiving a message of version 2.0, the working MOIB extractor may use an electronic form of a table to intelligently extract the data from what has been received. If a version 1.0 MOIB message is received the dictionary table reports Item 5 as not existing until version 2.0, and the message can be processed by skipping Item 5.

In FIG. 9E Item 4 1573 may be removed and the version may be bumped to 3.0 1575. Notice that the dictionary cannot remove the item reference. The dictionary must maintain the full historical evolution of the atom and, therefore, the ability to receive and process any version of the atom. In processing a received version 3.0 of this atom, item 4 may be skipped because the version span reports the existence of item 4 only from version 1.0 through removal in version 3.0. In this example of an evolving standard data type, a single dictionary may manage an atom through three evolutions.

Full self-describing machines using the DMOIB framework may or may not require version spanning technology. Full self-describing machines may report the machine model in the data dictionary each time, thus eliminating the need for version spanning technology. Alternatively, a compute platform may cache the dictionary maintaining a running history of discovered devices, thus requiring version spanning technology. Full self-describing machines may use version spanning technology to maintain a running definition of the device as the device is updated. A compute platform may cache the dictionary and update the dictionary as the machines evolve maintaining a running history of one particular device.

DMOIB compute applications preferably must manage full described machine dictionaries as well as global dictionaries of standard types. There are benefits and drawbacks to both. Fully dynamic machines may be free to define information modes complimentary to the device. It is likely the model may be unique to the machine. This may require a DMOIB compute platform to manage many full dictionaries from one machine to the next. The standard MOIB approach may be universal across machines and easier to manage in an application that understands common information models across many machines.

DMOIB applications preferably must manage and store both standard and dynamic types like memory in the human mind. The standard types may be consistent across all devices. A DMOIB application "brain" may be a conglomeration of newly discovered atoms specific to each device and potentially evolving with the device along with universal atoms of information also potentially evolving over time. The intelligence mechanism may check the atomic versions for a standard type like our NIBP atom. If it encounters a version of greater value for this standard type it may commit it to memory, thereby learning as machines it encounters evolve both standard and dynamic data.

Figure 9F:
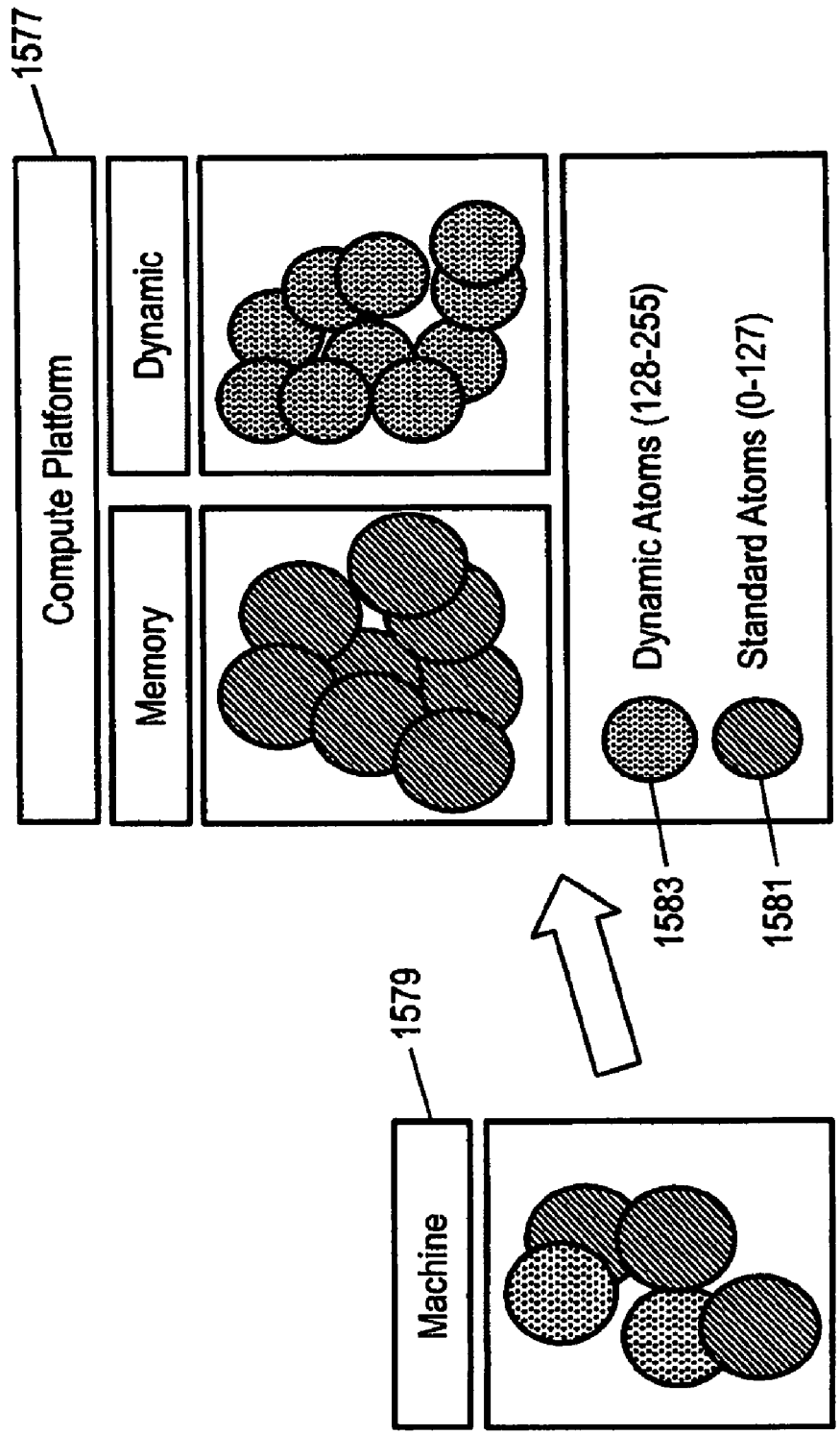
Figure 9G:
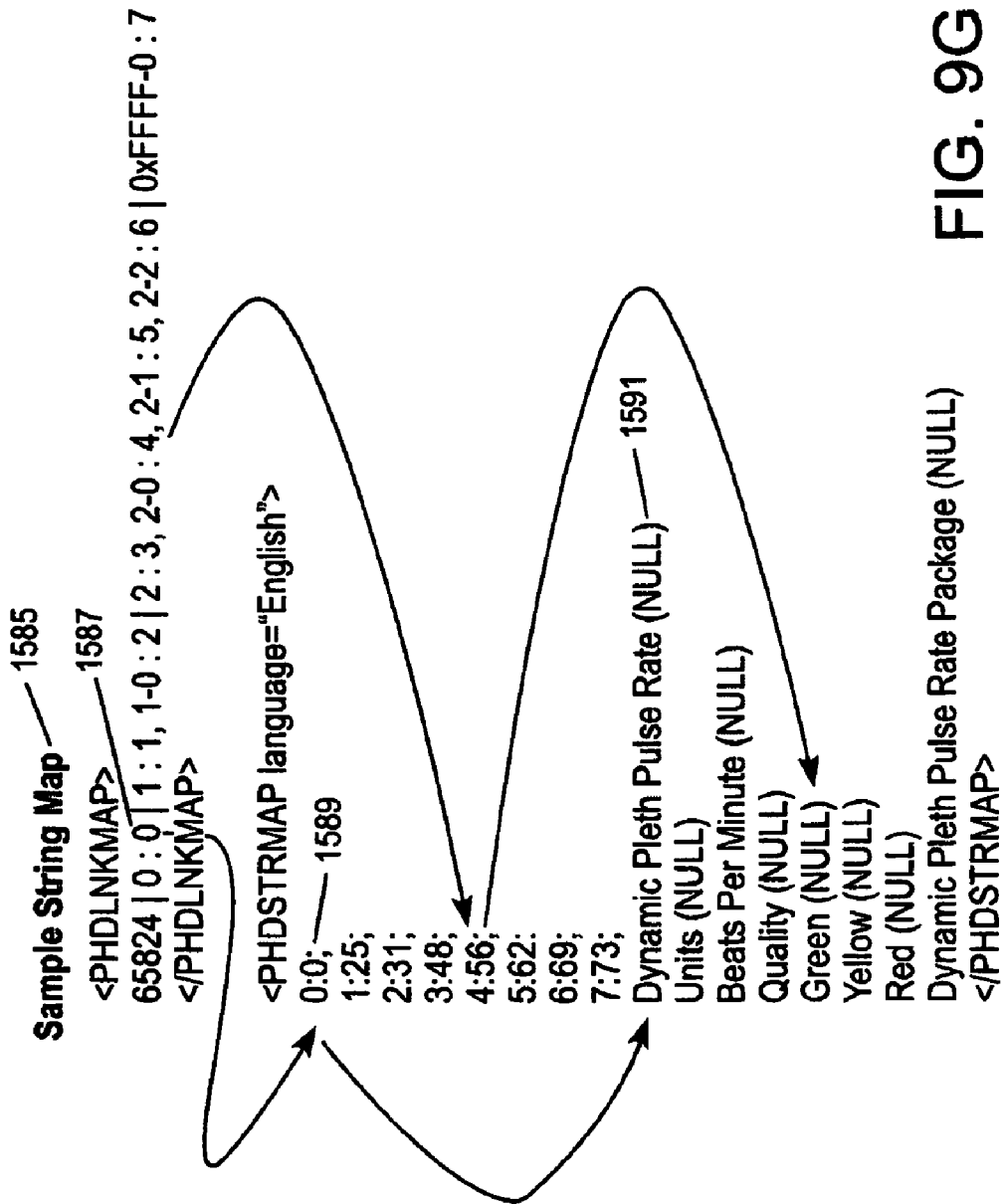

FIG. 9F is a representation of a compute platform 1577 exhibiting use of standard MOIB atomic families and dynamic DMOIB atomic families. Standard MOIB atomic families may be considered and/or defined as applied memory while dynamic may be considered cached disposable memory. FIG. 9F shows a scenario for a machine 1579 interacting with a compute platform 1577. The machine in this example may have both standard 1581 and dynamic 1583 atomic families in a machine dictionary. The compute platform may exhibit a dual role as defined earlier. The compute platform 1577 may contain an evolving memory base of static families as defined earlier that may define the foundation or building blocks for decision making. This does not completely rule out dynamic atoms in a decision making process. Dynamic atoms may contain an AKA (also-known-as) in the dictionary. AKAs may be taken from a global list representing a widely recognized nomenclature. For example a machine may define a heart rate as "HR" or spell it out as "Heart Rate". Attempting to process dynamic data in a disease based trending/clinical engine may be problematic in that the text ID of heart rate is defined differently across machines. The AKA may be an agreed upon number representing a clinically recognized information part. The AKA identifier may allow an intelligent process to search the data store to find all of a particular set of information and process the data for disease trends in a medical application, for example.

Use of App Gen to Create Communication Protocol Programs

The communication protocol may preferably be a binary protocol. The communication protocol may work with the taxonomic approach, which may be easily represented in XML. XML may be added as an option for serialization and as a modeling tool for creating and maintaining a list of atoms leveraged as new machines models are constructed. A single atom of NIBP is represented in XML 1471 in FIG. 8A. The XML may represent the taxonomic structure defined above.

Project teams building a new machine may use XML and MOIB rules to define the semantic model of a device. The project teams may take from a list of MOIB atoms, which contains the currently defined universe of standard atoms. FIG. 8B defines this process 1473. The definition process may start with the MOIB list 1477. Standard atoms 1475 may be extracted from the software component starting the construction of the Device Data Sheet ADS) 1479. At the second stage the device may define dynamic atoms 1481. Once this is complete the XML may be converted to software 1483 via an application generator compiler 1485.

Once the process of FIG. 8B is complete the software components can be integrated to the device.

The components created by the process above may provide the facilities for information implementation (MOIB of DMOIB) and communications (MOMP). Serialization may be thought of as a process for taking an instance of software structure or class and turning the attributes/members of the class into transferable data encoding. DMOIB and MOIB objects and MOMP message objects may support serializing information to binary and XML for transfer or use by applications.

Serialization to XML may be advantageous because XML has industry wide accepted tools for transforming the data into other formats. DMOIB and MOIB implementation can act as a protocol bridge. DMOIB or MOIB implementation can communicate with binary systems as well as bridge the data to information systems dealing with text based or higher level protocols like HL7. Serializing to XML and applying it to transform engines may allow the DMOIB or MOIB based binary networks to bridge to other protocols like HL7 and other forms of XML specification. Each atomic family in a machine may be capable of serialization to a either XML or binary. This may be inherent to all DMOIB and MOIB components produced by AppGen.

DMOIB implementation 1487 defined in FIG. 8C may define binary and XML serialization and deserialization. DMOIB implementation may receive (deserialized) XML or binary as well as serialize it to both formats for transfer. MOIB implementation as produced by AppGen 1485 may utilize a data dictionary 1489 for information extraction and display as previously described. AppGen 1485 may produce an implementation not reliant on the dictionary. In this form the MOIB components may have the structures of information built in and, therefore, may not utilize the dictionary, which is required for a DMOIB implementation.

XML may be used to represent the full taxonomic framework model for MOMP and DMOIB and may be used as input to the AppGen compiler creating the complete software implementation of the communication stack and the implementation of the either the static MOIB objects or the dynamic DMOIB data dictionary. The data dictionary may be a binary form of the XML and may be used as the mechanism to decode and encode data for a specific atomic family. The data dictionary may be used to decipher the makeup of an atomic family member from a raw binary stream or create one for populating. As defined earlier an atomic family may be a configuration set, an information or data set, or a parameter set.

XML may be used as the modeling tool for device information and messaging models as seen in the NIBP example. XML entities like the NIBP sample may be combined with others to form device data sheets. Device data sheets may form the atomic family representation of the device. These device data sheets (DDS) can be applied to the toolset to generate the binary form of XML encompassing the data dictionary. The dictionary may be linked to as many language specific string tables as needed. The link and string tables can be documented in XML and applied to the AppGen tool to provide implementation in platform independent string software.

AppGen may provide a machine or system development effort with a documentation mechanism for creating very complex models of information along with the messages for moving the information. Message constructs are determined by the MOMP and DMOIB frameworks for all machines and they must be adhered to so intelligent dialogue based on machine grammatical rules can provide an open dialogue for all machines. The communication protocol technology defines each machine 1491 as having its own fingerprint 1493 made up of multiple atomic families 1495 of information made up of data 1497 and messages 1499 as shown in FIG. 8D. Some of those items may be base standard items required in all machines while others may be unique to the device. If the structure is defined as decipherable by constituents of a system, a true plug and play capability may exist. This may allow devices to define information in models that could be learned as they are introduced on a network.

The process of creating a binary data dictionary from a DDS file may be transparent for the developer with the support of the AppGen tool. The output of this process may be a specifically formatted header that uses various macros defined in the DMOIB software component to describe objects and their members. These macros may allow the data definition to be presented in an easily recognizable format within the software project, and to automatically handle the creation of byte-array representations. While the header file produced by AppGen is intended to be used as-is, without modification.

Figure 10A:
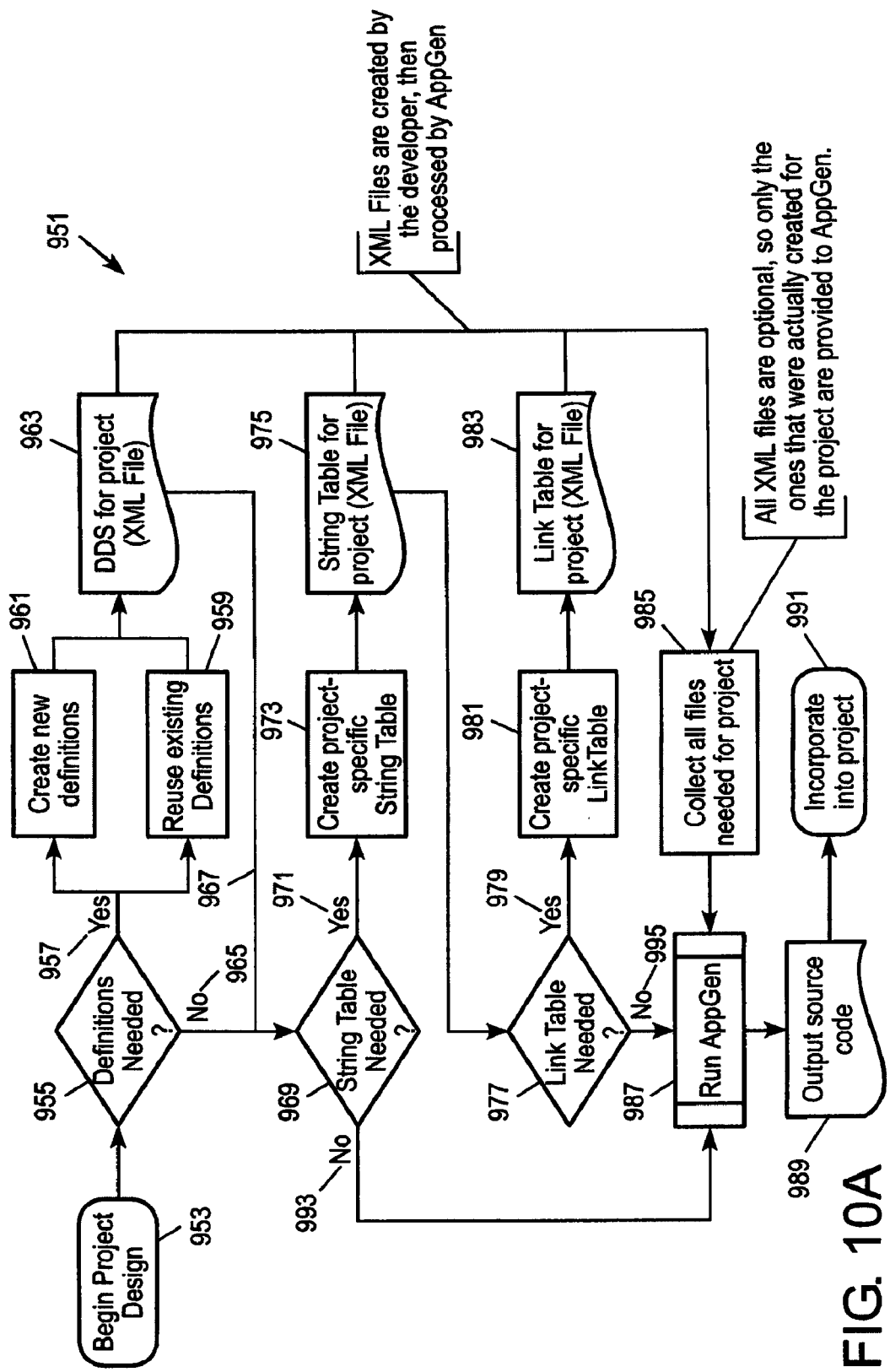
FIGS. 10A-10E show various aspects of an application generator creating programs.

FIG. 10A is a schematic diagram of a process 951 that may be used to generate software that implements the DMOIB/MOMP framework. Preferably, DMOIB is provided as a component that a developer incorporates into a larger software project. Initially, a user begins a design project 953.

A first step in the DMOIB generation process 951 after beginning the design project 953 may be determining whether definitions are needed 955. A DMOIB design project may generally require the creation of a data description sheet (DDS). A DDS may be an XML file used to describe data structures of atomic families used with DMOIB. The DDS may contain definitions for the member items required for the target software project. Alternatively, definitions for member items may be stored in a library of data definitions and/or data dictionaries.

Finalized definitions may be collected into a single DDS file that is associated with the target software project. If definitions are needed 957, then existing definitions may be used 959 or new definitions may be created 961, depending on needs of individual situations. The new and/or existing definitions may then be used to create an XML file of the DDS for the project 963. The DDS may then be compiled into a data dictionary.

If no definitions are needed 965, or a DDS has been created 967, the next step may be to determine whether optional string tables are needed 969 for the target software project. The string tables are not necessary to use DMOIB object functionality, but may provide the developer with a way to define portable string tables that can be managed implicitly by DMOIB component software. The string tables may also be declared using specific XML formats, and support may be provided for internationalization using string tables. If string tables are needed 971, project specific string tables may be created 973. The string tables may then exist as an XML file 975.

In addition to the string tables, the developer may also create optional link tables for the DMOIB data dictionary to link to the string tables. Link tables are primarily useful when both data definitions and string tables have been declared within the scope of the same project. Link tables may act as a way to associate specific members and enumerations from the data definition to descriptive text in the string table. The link tables may be declared using specific XML formats. If a string table is created for a project 975, a determination may be made as to whether a link table is needed 977. If a link table is needed 979, project specific link tables may be created 981. The link tables may then exist as an XML file 983.

The DDS 963, string table 975, and/or link table 983 are preferably XML files created by the developer. A collection of one or more of the XML files needed for a project are collected 985. All XML files are preferably optional, so only the XML files that are actually created for the project may be provided to an application generator (AppGen) 987. Preferably, once all of the desired elements are created in specified XML formats, the elements are then processed as a batch by the AppGen 987. The AppGen 987 may be a pre-compiler tool for converting XML formatted DDSs and the other XML files described above into useable source code. The AppGen 987 can parse the input XML files (i.e., definitions, string tables, and link tables) and generate source code implementing the MOMP/DMOIB frameworks as output 989 that is incorporated into a project 991. When processing the XML files, AppGen preferably determines which elements are present in the XML files and executes steps to link definitions to strings where applicable in the output source code.

Each of the inputs to AppGen described above (data definitions, string tables, and link tables) may be optional to a software project and may be separately utilized. Data definitions can be used by themselves for data management, string tables can be used by themselves to provide portable strings, and link tables are primarily applicable when both data definitions and string tables are available. For example, if a determination is made that string tables are not needed 993, then only the DDS 963 may be input to the AppGen 987. Additionally, if a determination is made that link tables are not needed 995, then only the DDS 963 and the string table 975 may be input to the AppGen 987.

Most of the code produced by AppGen 987 may be binary encoded tables of information that can be used with DMOIB atomic families. DMOIB may provide a generic way to describe string tables for usage in software projects. The string tables may originate as XML definitions (similar to data definitions), which allow the developer to create a list of symbolic links, and associate strings to those links. The symbolic links may act as unique identifiers that directly correlate to textual descriptions stored in the string table.

After a string table has been characterized in an XML definition, it can be processed by AppGen to create source code for use with DMOIB. The source code may contain binary tables that are guaranteed to include all the strings present in the XML definition, but organizes them more optimally for portability.

Data Classes

The organization of the DMOIB data classes is preferably split into three main sections: (1) the member items themselves, (2) the data dictionaries that manage definitions, and (3) the string tables that manage descriptions for elements of the definitions.

The dictionaries may be independent components that collect and manage many definitions from different sources. Some definitions may be created statically, at compile time, while others are loaded dynamically at run time. The dictionary can provide interfaces to access all types of definitions abstractly and anonymously, to provide the developer with a generic mechanism to handle definitions that might come from connected devices or be loaded from a cache.

The DMOIB member items may be dependent upon the dictionaries to provide the DMOIB member items with definitions that can be used during instantiation. While the dictionary manages the definitions, the DMOIB member items put them to use. A single dictionary can be shared among many DMOIB member items, but each DMOIB member item must retain a reference to an existing dictionary at all times, in case they need access to definition information.

String tables may be a completely independent component used without any other element of DMOIB. While dictionaries are technically independent as well, they are intended to work with DMOIB member items. However, DMOIB string tables can provide a generic interface that may be used by any software project to manage and access strings based on symbolic links. In addition to this general usage, DMOIB string tables can also be "linked" to DMOIB member items to provide implicit descriptions for all DMOIB member items and enumerations. By doing this, a developer can query a DMOIB object directly for descriptive strings, and the DMOIB member items then uses the linked string table to resolve those queries to a literal string.

The data dictionary used with DMOIB and string table classes may act as interfaces for managing, extracting, and displaying information from binary information streams.

For each unique language or category of presentation in the definition, there may be a single language table created. Each language table may include all strings from the definition that are associated with that specific language or application (e.g. large screen display and small screen display strings). Also, each language table can be disparate in the strings contained therein, and does not need to be symmetrical with any other language tables created from the same definition. The only constraint may be that symbolic link associations must be maintained across all language tables.

The binary string tables may then be managed by DMOIB to provide standard interfaces for accessing strings. The DMOIB atomic families may allow conversion of symbolic links to actual strings without requiring the developer to know anything about the structure of the tables.

A string table may have a very simple format, consisting of only 2 main sections: the symbolic link translation table and the string block. The symbolic link translation table can be an array of numeric offsets into the string block where certain strings can be found, and the string block can be a large piece of memory where all the strings from a definition for a single language are stored.

The symbolic link translation table used to identify strings may be numeric values generated cooperatively by the AppGen and DMOIB. The link values can eventually resolve to sequential integral values, based on the symbolic link position in the original definition. For example, the first 10 entries of a string table definition may be given the values [0, 1, 2, . . . , 8, 9]. The value can then be used directly as an offset into the translation table section, and the value found at that position is an offset itself. The resultant offset can be used to traverse the larger string block and point directly at the head of a null-terminated string corresponding to the original symbolic link.

The string block can be a single contiguous block of strings, tightly packed, where each one is null-terminated. The values contained in the string block can be read-only, and preferably cannot be modified externally by the developer. Each string in the block can also be null-terminated, allowing the developer to access those constant string values and use them directly.

Figure 10B:
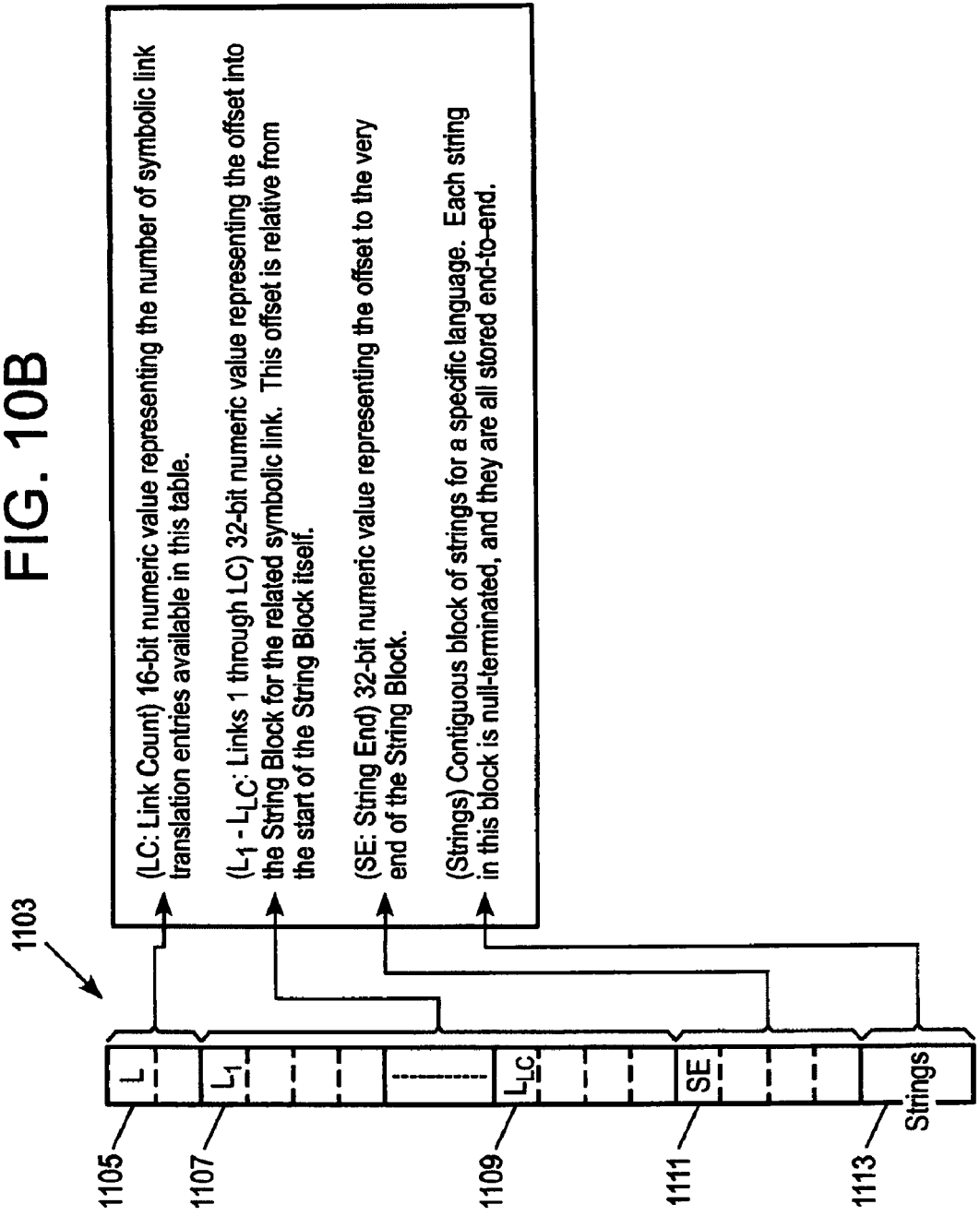

FIG. 10B shows an explicit layout 1103 for a string table. Each box in the column along the left side represents a single byte (8-bit) value, where boxes with dashed lines represent multi-byte values. The internal structure preferably is not directly accessed by a developer. All interaction with the string table should be made through a string table class. A first box LC (Link Count) 1105 may be a 16-bit numeric value representing the number of symbolic link translation entries available in the table. A next series of boxes $L_1$ (Link 1) 1107 through $L_{LC}$ (Link LC) 1109 may be 32-bit numeric values representing the offset into the string block for the related symbolic link. The offset may be relative from the start of the string block itself. The next box SE (String End) 1111 may be a 32-bit numeric value representing the offset to the very end of the string block. Strings 1113 may follow SE 1111. Strings 1113 may be contiguous blocks of strings for a specific language. Each string 1113 in the block is null-terminated, and stored end-to-end.

Link Tables

If a developer has defined both data definitions and string tables for a software project using the DMOIB software component, then they have the option to also define a link table for the project. Link tables can be another type of XML file, formatted much like the string table file. The purpose of a link table may be to provide an explicit linkage between the data members/enumerations from a data definition to the symbolic links available in a string table.

After the DDS, string table file, and link table file have all been created for a target software project, they can be processed by AppGen in a batch to generate source code for use with DMOIB. The source code may be very similar to what is generated when no link table is available, but includes an extra binary table that links ClassID and MemberID combinations to symbolic links at runtime. ClassID and MemberID may generally identify the items to DMOIB. As described above, a link table may associate elements to symbolic links instead of directly to strings. Therefore, a single link table corresponds to any relevant string tables.

The structure of the link table may allow data definitions and string tables to be updated independent of one another, while maintaining functionality. The link table can remove any dependencies data definitions might have on string tables, and vice versa, by enforcing the dependencies in the external link table file.

The binary link tables can be managed by the same string table class used for string tables. This may allow a single component to be the authority for strings, and makes the implicit linking of members to strings more centralized.

Each link table may contain one lookup entry for a single definition, where the format is similar to that of its related data definition (containing a header section at the front of the table with general options, followed by a variable number of lookup sub-entries).

The header section of a link table may be a simple structure containing only three elements. The first element can be a ClassID designator that matches a data definition related to the table. The ClassID can provide a method for searching through a list of link tables and correlating a specific link table to a data definition. Following the ClassID is preferably a member count, which denotes how many members are supported in this particular link table. It is possible that an old link table could be used for a more recent definition that contains new members. In this case, the link table would still be applicable because it would state explicitly the members for which it can provide translations. The third element of the header can be an enumeration count, which follows the same premise as the member count. If new enumerations are added to a definition, an old link table can still support it.

Following the header segment can be a variable number of member, enumeration, and enumerator entries, each with their own sub-format. The lookup entries for all three elements can match those provided in the original data definition on a 1-to-1 basis. Preferably, there is always a single entry in the link table for every member, enumeration, and enumerator in the data definition.

For each entry available in the link table XML file, there may be a matching entry in the binary link table with the appropriate lookup data. If however there is no entry information for an element in the original XML file, then the related entry in the binary link table may be initialized to a default value, to denote that it does not have lookup data associated with the element.

For member and enumeration entries, the formats may be identical. Both members and enumerations may have the same characteristics pertaining to how sets of enumerator values are assigned to them, as well as their linkage to textual descriptions. Because of this, both may be treated in the same manner within the link table structure. Each entry preferably contains a pair of numeric values that link it to other elements. The first value of the numerical pair may be an offset position from the head of the link table where an associated enumerator list can be found. For enumeration types, this may always be a valid offset to a list of additional values. But for members, this value could be an invalid offset, as members may or may not be linked to a set of enumerated values. If the offset associated with a member is invalid, then the member is not linked to an enumerated set. The second value of the numerical pair may be the value of the symbolic link assigned to the entry. This value can be used with the normal string table structure to retrieve a textual description for the entry.

Enumerators use a structure that is similar to the previous elements, except the data may have a different meaning. At the head of each enumerator set can be a single numeric value representing the number of values within the set. This may be needed to determine the boundaries of the set when it is being searched. After the single value, there may be a variable number of numeric pairs representing the enumerator's value and related symbolic link. The first value of the numeric pair may be the value of the enumerator, as assigned in the original data definition. The first value should be unique within the enumerator list, and may be used to identify the correct value when searching the list. The second value of the numeric pair may be the value of the symbolic link assigned to the entry. The second value may be used with the normal string table structure to retrieve a textual description for the entry.

Figure 10C:
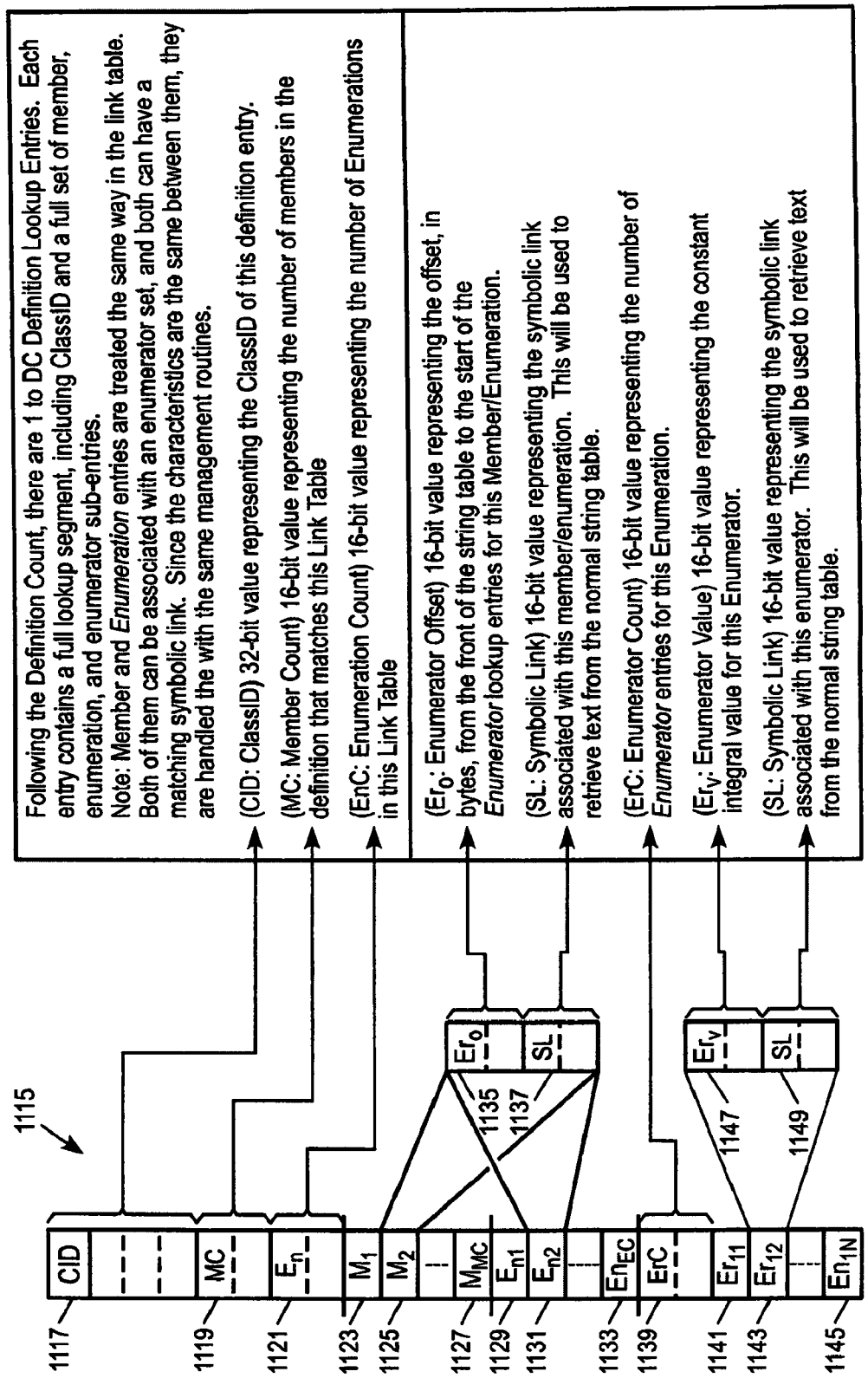

FIG. 10C shows an explicit layout 1115 for a link table. Each box in the column along the left side represents a single byte (8-bit) value, where boxes with dashed lines represent multi-byte values. The internal structure preferably is not directly accessed by a developer. All interaction with the link table should be made through a string table class.

From the definition count, there may be 1 to DC definition lookup entries. Each entry contains a full lookup segment, including ClassID and a full set of member enumeration, and enumerator sub-entries. Member and enumeration entries are treated the same way in the link table. Both can be associated with an enumerator set, and both can have a matching symbolic link. Since the characteristics are the same between member and enumeration entries, they are both handled by the same management routines.

A first box CID (ClassID) 1117 may be a 32-bit value representing the ClassID of the definition entry. A next box MC (Member Count) 1119 may be a 16-bit value representing the number of members in the definition that matches the link table. A next box EnC (Enumeration Count) 1121 may be a 16-bit value representing the number of enumerations in the link table.

Following the initial information on CID 1117, MC 1119 and En 1121, are members $M_1$ 1123, $M_2$ 1125, ..., $M_{MC}$ 1127, and enumeration $En_1$ 1129, $En_2$ 1131, ..., $En_{EC}$ 1133. Each member and/or enumeration may have $Er_O$ (Enumerator Offset) 1135 and SL (Symbolic Link) 1137. $Er_O$ 1085 may be a 16-bit value representing the offset, in bytes, from the front of the string table to the start of the enumerator lookup entries for the member/enumeration. SL 1137 may be a 16-bit value representing the symbolic link associated with the member/enumeration and used to retrieve text from the normal string table.

Following the member and enumeration section may be an ErC (Enumeration Count) 1139. The ErC 1139 may be a 16-bit value representing the number of enumerator entries for the enumeration.

Following the ErC 1139 may be enumerators $Er_1$ 1141, $Er_2$ 1143, ..., $Er_N$ 1145. Each enumerator may contain an $Er_V$ (Enumerator Value) 1147 and an SL (Symbolic Link) 1149. The $Er_V$ 1147 may be a 16-bit value representing the constant integral value of the enumerator. SL 1149 may be a 16-bit value representing the symbolic link associated with the member/enumeration and used to retrieve text from the normal string table.

Figure 10D:
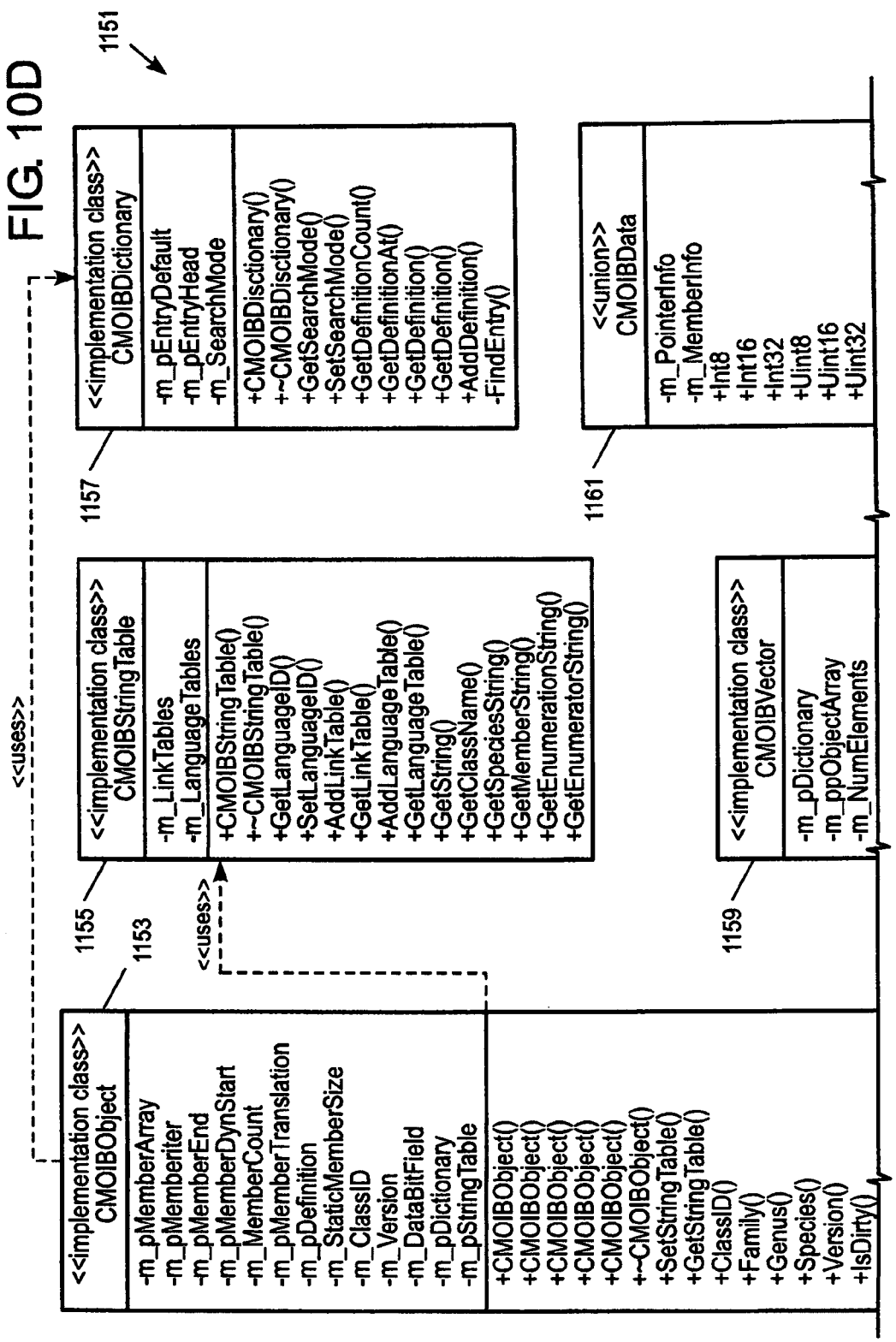
Figure 10E:
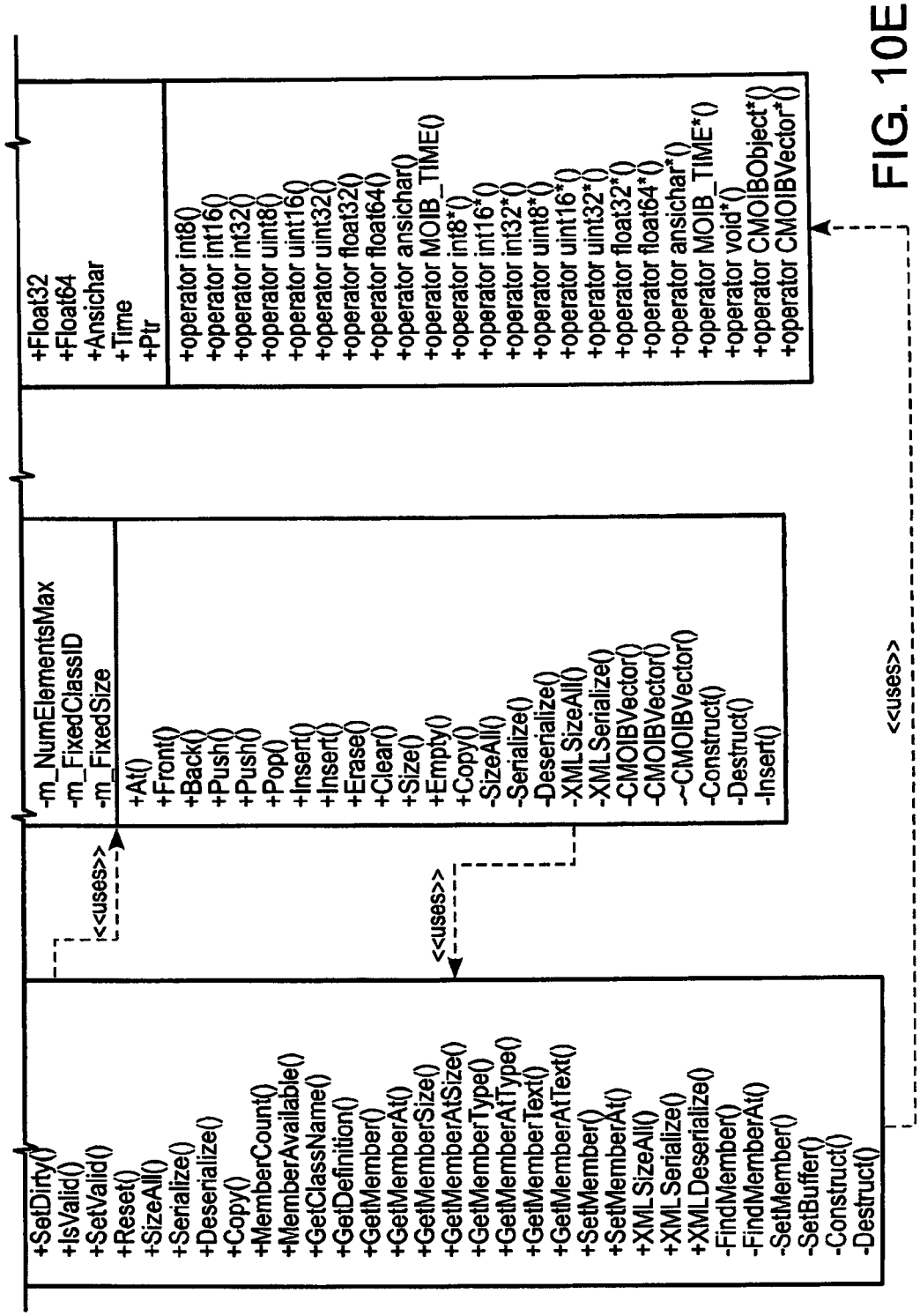

FIG. 10D and FIG. 10E, which is a continuation of FIG. 10D, show dependencies/usage of all classes in a DMOIB software component 1151. In a preferred embodiment, implementation classes may include CMOIBObject 1153, CMOIBString Table 1155, DMOIBDictionary 1157, DMOIBVector 1159, and CMOIBData 1161.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

What is claimed is:

1. A non-transitory computer-readable medium carrying one or more sequences of instructions for controlling communications between one or more network devices, which instructions, when executed by one or more processors, cause the one or more processors to carry out the steps of:

receiving, over a network, a data dictionary corresponding to a network device in a received form, wherein the data dictionary is derived from a device data sheet, wherein the device data sheet is a model of the network device, and wherein the data dictionary comprises one or more data definitions specific to the network device and a global unique identifier for the network device;

caching the data dictionary, the data dictionary including a hierarchal classification scheme for physiological data, wherein the hierarchal classification scheme comprises a first level, a second level, and a third level, wherein the first level defines a type of physiological data, the type of physiological data being one of two or more families of physiologic information supported by a network device, wherein the second level defines a type of action related to the type of physiological data from the first level, and wherein the third level defines an object of the action from the second level;

receiving physiological data from the network device, the physiological data including a heart rate, a respiration rate and a blood pressure;

accessing the one or more data definitions from the data dictionary;

extracting information from the received physiological data;

using an interpreter, the interpreter using the one or more data definitions from the cached data dictionary to decipher the extracted information from the received physiological data; and processing the information, wherein the device data sheet is used to derive the data dictionary by creating one or more data definitions for a specific project, collecting the one or more data definitions in an XML formatted device data sheet, compiling the one or more data definitions in the XML formatted device data sheet with an application generator and outputting source code, creating a string table and compiling the string table with the device data sheet, and creating a link table and compiling the link table with the string table and the device data sheet.

2. The computer-readable medium of claim 1, further comprising applying attributes from the data dictionary to the extracted information.

3. The computer-readable medium of claim 1, wherein one or more data definitions are standard definitions.

4. The computer-readable medium of claim 3, wherein the standard definitions are reserved for information regulated by a standard setting organization.

5. The computer-readable medium of claim 4, further comprising accessing the standard definitions stored in a collection of definitions.

6. The computer-readable medium of claim 1, wherein the device data sheet is XML.

7. The computer-readable medium of claim 6, wherein the XML is compiled to source by an application generator.

8. The computer-readable medium of claim 6, further comprising serializing and deserializing byte streams of information.

9. The computer-readable medium of claim 8, wherein the serialization provides a built-in protocol bridge between binary and XML network devices.

10. The computer-readable medium of claim 6, further comprising serializing and deserializing XML.

11. The computer-readable medium of claim 10, wherein the serialization provides a built-in protocol bridge between binary and XML network devices.

12. The computer-readable medium of claim 1, wherein the data dictionary is created from a device data sheet converted to binary form.

13. The computer-readable medium of claim 1, wherein the global unique identifier is unique to the data received from the network device and is based upon the device data sheet.

14. The computer-readable medium of claim 1, further comprising receiving the data dictionary over the network using a learning process, wherein the learning process comprises interpreting information in the data dictionary, extracting information from the data dictionary and acting on the extracted information.

15. The computer-readable medium of claim 1, wherein the learning process evolves so that newer versions of the data dictionary are committed to memory when encountered.

16. A method of communicating between network devices embedded within a tangible medium and executed by one or more processors comprising:

receiving one or more data dictionaries over a network;

caching the one or more data dictionaries, the one or more data dictionaries including a hierarchal classification scheme for physiological data, wherein the hierarchal classification scheme comprises a first level, a second level, and a third level, wherein the first level defines a type of physiological data, the type of physiological data being one of two or more families of physiologic information supported by a network device, wherein the second level defines a type of action related to the type of physiological data from the first level, and wherein the third level defines an object of the action from the second level, sending a communication request to a network device, receiving a response from the network device comprising physiological data, and using an interpreter to process the response according to the one or more cached data dictionaries, the interpreter using one or more data definitions from the one or more cached data dictionaries to decipher the physiological data in the response, wherein the device data sheet is used to derive the data dictionary by creating one or more data definitions for a specific project, collecting the one or more data definitions in an XML formatted device data sheet, compiling the one or more data definitions in the XML formatted device data sheet with an application generator and outputting source code, creating a string table and compiling the string table with the device data sheet, and creating a link table and compiling the link table with the string table and the device data sheet.

17. The method of claim 16, further comprising sending a request for one or more additional data dictionaries to the network device and receiving the one or more additional data dictionaries.

18. The method of claim 17, further comprising adding information from the one or more additional data dictionaries into the one or more cached data dictionaries.

19. The method of claim 18, further comprising receiving data from the network device and processing the data via the hierarchal classification scheme.

20. The method of claim 16, further comprising accessing standard data definitions based upon the identification information if the network device does not support self-description and the hierarchal classification scheme.

21. The method of claim 16, wherein the type of action defines a semantic identity for a message.

22. The method of claim 16, wherein the object of the action is the specific information represented.

23. The method of claim 16, wherein the hierarchal classification scheme is expanded to represent new information.

* * * * *